US008592364B2

(12) United States Patent
Swartz et al.

(10) Patent No.: US 8,592,364 B2
(45) Date of Patent: Nov. 26, 2013

(54) CCR7 LIGAND DELIVERY AND CO-DELIVERY IN IMMUNOTHERAPY

(75) Inventors: Melody A. Swartz, Préverenges (CH); Jeffrey A. Hubbell, Préverenges (CH); Alice A. Tomei, Lausanne (CH); Jacqueline D. Shields, Cumbria (GB); Iraklis Kourtis, Larissa (GR)

(73) Assignee: Ecole Polytechnique Federale de Lausanne ("EPFL"), Lausanne (CH)

( * ) Notice: Subject to any disclaimer, the term of this patent is extended or adjusted under 35 U.S.C. 154(b) by 0 days.

(21) Appl. No.: 13/025,009

(22) Filed: Feb. 10, 2011

(65) Prior Publication Data

US 2011/0206759 A1 Aug. 25, 2011

Related U.S. Application Data

(60) Provisional application No. 61/303,442, filed on Feb. 11, 2010.

(51) Int. Cl.
*A61K 38/00* (2006.01)
*A61K 38/16* (2006.01)
*A61K 38/17* (2006.01)
*A61K 38/18* (2006.01)
*A61K 38/19* (2006.01)
*A61K 38/20* (2006.01)

(52) U.S. Cl.
USPC ........... 514/1.1; 435/69.7; 424/422; 424/423; 424/450; 424/457; 424/458; 424/469; 424/484; 424/489; 424/85.2; 514/8.9

(58) Field of Classification Search
None
See application file for complete search history.

(56) References Cited

U.S. PATENT DOCUMENTS

| | | | |
|---|---|---|---|
| 4,687,481 A | 8/1987 | Nuwayser | |
| 5,142,047 A | 8/1992 | Summerton et al. | |
| 5,185,444 A | 2/1993 | Summerton et al. | |
| 5,227,293 A | 7/1993 | Stengelin et al. | |
| 5,279,544 A | 1/1994 | Gross et al. | |
| 5,330,768 A | 7/1994 | Park et al. | |
| 5,358,857 A | 10/1994 | Stengelin et al. | |
| 5,410,016 A | 4/1995 | Hubbell et al. | |
| 5,468,505 A | 11/1995 | Hubbell et al. | |
| 5,558,642 A | 9/1996 | Schweich, Jr. et al. | |
| 5,593,673 A * | 1/1997 | Dinsmore | 424/93.7 |
| 5,648,506 A | 7/1997 | Desai et al. | |
| 5,874,500 A | 2/1999 | Rhee et al. | |
| 5,885,808 A | 3/1999 | Spooner et al. | |
| 5,948,639 A | 9/1999 | Gimeno et al. | |
| 5,994,104 A | 11/1999 | Anderson et al. | |
| 6,322,804 B1 | 11/2001 | Dionne et al. | |
| 6,331,422 B1 | 12/2001 | Hubbell et al. | |
| 6,512,103 B1 | 1/2003 | Dairaghi et al. | |
| 6,562,347 B1 | 5/2003 | Kwak et al. | |
| 6,607,740 B1 | 8/2003 | Hubbell et al. | |
| 6,629,949 B1 | 10/2003 | Douglas | |
| 6,828,401 B2 | 12/2004 | Nho et al. | |
| 6,905,688 B2 | 6/2005 | Rosen et al. | |
| 6,960,452 B2 | 11/2005 | Hubbell et al. | |
| 7,175,988 B2 | 2/2007 | Roschke et al. | |
| 7,186,413 B2 | 3/2007 | Bouhadir et al. | |
| 7,241,730 B2 | 7/2007 | Hubbell et al. | |
| 7,247,609 B2 | 7/2007 | Lutolf et al. | |
| 7,250,037 B2 | 7/2007 | Shermer et al. | |
| 7,291,673 B2 | 11/2007 | Hubbell et al. | |
| 7,332,586 B2 | 2/2008 | Franzen et al. | |
| 7,432,239 B2 | 10/2008 | Mohanty et al. | |
| 7,704,943 B2 | 4/2010 | Griffin et al. | |
| 7,803,748 B2 | 9/2010 | Sung et al. | |
| 2002/0004037 A1 | 1/2002 | Koteliansky et al. | |
| 2004/0138422 A1 | 7/2004 | Demotz et al. | |
| 2005/0053579 A1 | 3/2005 | Galipeau et al. | |
| 2005/0203010 A1 | 9/2005 | Kim | |
| 2005/0203022 A1 | 9/2005 | Gotwals et al. | |
| 2005/0250936 A1 | 11/2005 | Oppermann et al. | |
| 2006/0193787 A1 | 8/2006 | Feng | |
| 2006/0257359 A1 | 11/2006 | Francois et al. | |
| 2006/0292164 A1 * | 12/2006 | Horwitz | 424/185.1 |
| 2007/0020230 A1 * | 1/2007 | Kaps et al. | 424/85.1 |
| 2009/0202640 A1 | 8/2009 | Paoletti et al. | |
| 2009/0232899 A1 | 9/2009 | David et al. | |
| 2009/0297613 A1 | 12/2009 | Ringe et al. | |
| 2009/0324538 A1 | 12/2009 | Wong et al. | |

OTHER PUBLICATIONS

Ziegler et al. (2006, J. Am. Soc. Nephrol. 17:2521-2532).*
Schmoekel et al. (2005, Biotechnology and Bioengineering 89(3):253-262).*
Brewitt, "Vaccines, adjuvants and potential toxicity—Letter to the Editor", Townsend Letter for Doctor and Patients, Nov. 2003. http://findarticles.com/p/articles/mi_m0ISW/is_244/ai_111271897 (3 pages).
Jung et al., "Origins and Functions in the Mononuclear Phagocyte System", Life Science Open Day, pp. 200-201 (2006).
Lu et al., "Design of novel bioconjugates for targeted drug delivery," Journal of Controlled Release, 78 (2002) 165-173.
Lutolf et al ., "Syntheses and Physicochemical Characterization of End-Linked Poly(ethylene glycol)-co-peptide Hydrogels Formed by Michael-Type addition," Biomacromolecules, 2003, 4, 713-722.
Lutolf et al., "Repair of bone defects using synthetic mimetics of collagenous extracellular matrices," 2003 Nature Publishing Group http://www.nature.com/naturebiotechnology. Published online Apr. 2003;doi:1038/nbt818.
Song et al., "CCR7-CCL19/CCL21-Regulated Dendritic Cells are Responsible for Effectiveness of Sublingual Vaccination," The Journal of Immunology Sep. 25, 2011.
Stein et al, "CCR7-mediated phusiological lymphocyte homing involves activation of a tyrosine kinase pathway." http://www.bloodjournal.hematology.org at Korea Intellectual Property Office, Sep. 25, 2011.

(Continued)

Primary Examiner — Elizabeth C Kemmerer
(74) Attorney, Agent, or Firm — Dardi & Herbert, PLLC.; Curtis B. Herbert

(57) ABSTRACT

Chemokines may be administered to a patient for immunotolerization. Chemokines include CCL19 and CCL21. Materials and methods for accomplishing tolerization and described.

26 Claims, 20 Drawing Sheets

(56) References Cited

OTHER PUBLICATIONS

Trentin et al., "Peptide-matrix-mediated gene transfer of an oxygen-insensitive hypoxia-inducible factor-1a varient for local induction of angiogenesis." PNAS Feb. 21, 2006, vol. 103 No. 8.

Ziegler et al "CCR7 Signaling Inhibits T Cell Proliferation." The Journal of Immunology. J Immunol 2007;179;6485-6493.

Gao et al., "Anti-tumor responses induced by chemokine CCL19 transfected into an ovarian carcinoma model via fiber-mutant adenovirus vector" Biol. Pharm. Bulletin 28(6), 2005, 1066-1070.

Krautwald et al., "Ectopic expression of CCL19 impairs alloimmune response in mice" Immunology, 2004, vol. 112, 301-309.

Pilkington et al., "Inhibition of generation of cytoxic t lymphocyte activity by a CCL19/marcophage inflamatory protein (MIP)-beta-antangonist" The Journal of Biological Chemistry, 2004, vol. 279, 40276-40282.

Song et al., "CC47-CCL19/CCL21-regulated dendritic cells are responsible for effectiveness of sublingual vaccination" The Journal of Immunology, 2009, vol. 182, 6851-6860.

Stein et al., "CCR7-mediated physiological lymphosyte homing involves activation of a tyrosine kinase pathway" Blood Journal, 2003, vol. 101, 38-44.

Ziegler et al., CCR7 signaling inhibits t cell proliferation The Jounral of Immunology, 2007, vol. 179, 6845-6493.

* cited by examiner

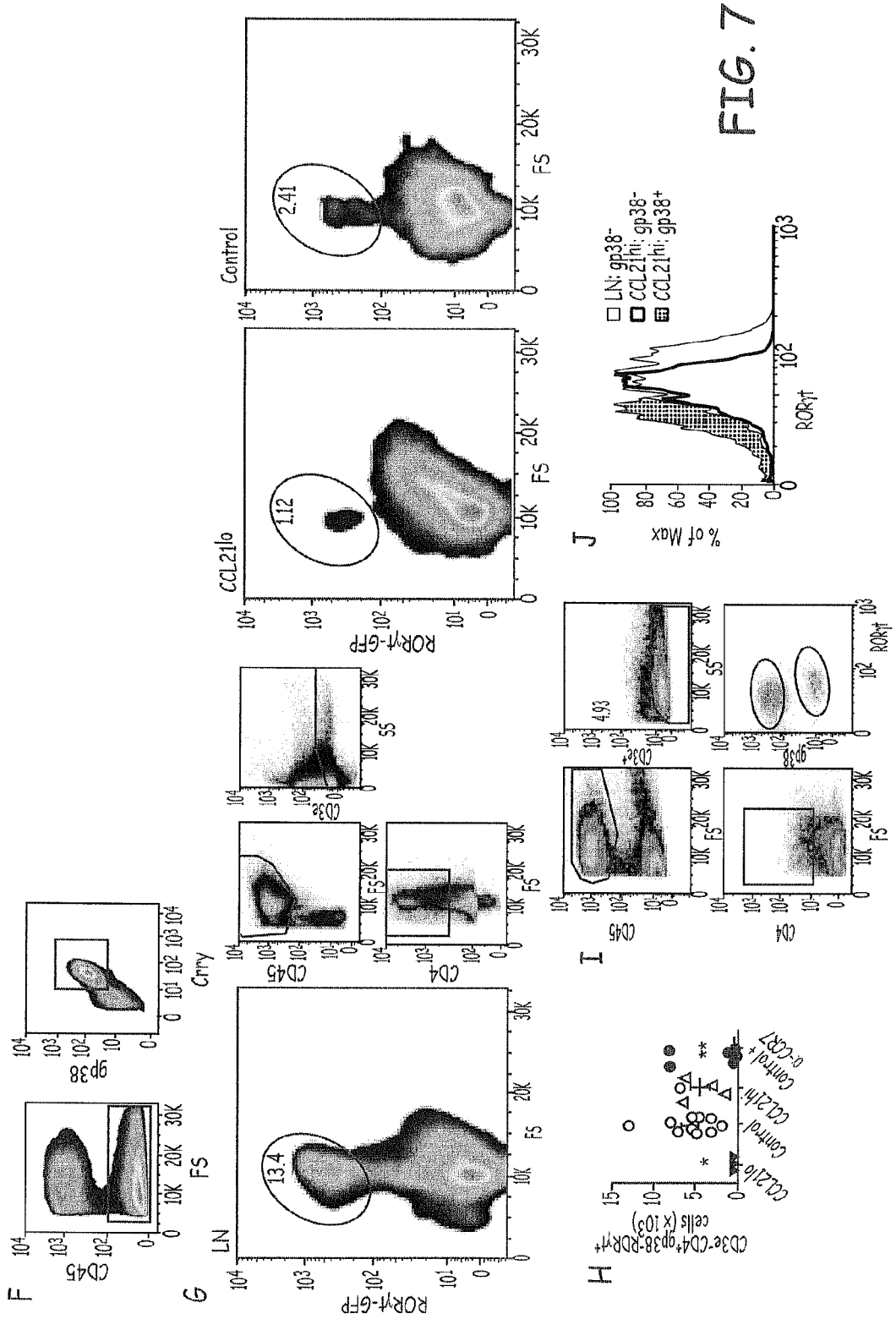

Murine CCL21 leucine (mCCL21leu) / CCL21b
*NCBI Reference Sequence: NC_000070.5*
*Mus musculus chromosome 4, reference assembly (C57BL/6J)*

CACACACACAGACCCCAACTTGCAGCTGTCCATCTCACCTACAGCTCTGGTCT
CATCCTCAACTCAACCACAATCATGGCTCAGATGATGACTCTGAGCCTCCTTA
GCCTGGTCCTGGCTCTCTGCATCCCCTGGACCCAAGGTACCAAGGAGGGAGA
GGCTTTGGCTGGGGAAGGGGGCCATAGAGACACCTTATAAGCCGCAGCTGGG
TCTGTGCACCTACCTTGCAGGCAGTGATGGAGGGGACAGGACTGCTGCCTT
AAGTACAGCCAGAAGAAAATTCCCTACAGTATTGTCCGAGGCTATAGGAAGC
AAGAACCAAGTTTAGGCTGTCCCATCCCGGCAATCCTGTGAGTGCGCTGATC
GGGTGGGTACAGGCTGGTGGTTGGGTTGGGGAGGTGTGATGGGCCAGACTAA
GA
AAGCTTGCTGCCCTCCAACCCTCAGGTTCTTACCCCGGAAGCACTCTAAGCCT
GAGCTATGTGCAAACCCTGAGGAAGGCTGGGTGCAGAACCTGATGCGCCGCC
TGGACCAGCCTCCAGCCCCAGGGAAACAAAGCCCCGGCTGCAGGAAGAACC
GGGGAACCTCTAAGTCTGGAAAGAAAGGAAAGGGCTCCAAGGGCTGCAAGA
GGTGAGGCTGCTGAAGGGATGGAAGGGGAACAAAGAGGAGCCTCCCTCCAC
CTGCCTCTCACACTTCTTTTCTGCCCTGCCAGAACTGAACAGACACAGCCCTC
AAGAGGATAGCCCAGTAGCCCGCCTGGAGCCCAGGAGATCCCCCACGAACTT
CAAGCTGGGTGGTTCACGGTCCAACTCACAGGCAAAGAGGGAGCTAGAAAA
CAGACTCAGGAGCCCAAAGCAGCCACCTCATGCTGGCCTCCGTCCACACCCT
TGCCCTGCTTCAACCATTACATCTGCACGGCCATCCCTTTCTTACCTGGCGGA
GCTGCCTTCCCTGGGGTAGACCTAGAGAGTCAGAAGAAAGAGTGTCTCCCAG
GGAATGAGGAAGGAGACAGCAGGACTGTCCCCTCTAGGAGGTCACTCAGGTC
CCAAGACCTGAACCTGCTCTCCATGGCGCCCTCCCCTTGTCCTTGCACCTATG
ATTTATACCTAACTGAATAAAAAGTGATCCAGCCTCA

FIG. 15A

Murine CCL21 leucine (mCCL21leu) / CCL21b
*NCBI Reference Sequence: NC_000070.5*
*Mus musculus chromosome 4, reference assembly (C57BL/6J)*

*Coding region*
Atggctcagatgatgactctgagcctccttagcctggtcctggctctctgcatcccctggacccaaggcagtgatggaggggga
caggactgctgccttaagtacagccagaagaaaattccctacagtattgtccgaggctataggaagcaagaaccaagtttaggct
gtcccatcccggcaatcctgttcttaccccggaagcactctaagcctgagctatgtgcaaaccctgaggaaggctgggtgcaga
acctgatgcgccgcctggaccagcctccagccccagggaaacaaagccccggctgcaggaagaaccggggaacctctaagt
ctggaaagaaaggaaagggctccaagggctgcaagagaactgaacagacacagccctcaagaggatag

FIG. 15B

*UniProtKB/Swiss-Prot P84443 (CC21A_MOUSE)*

MAQMMTLSLLLSLVLALCIPWTQGSDGGGQDCCLKYSQKKIPYSIVRGYRKQEPS
LGCPIPAILFLPRKHSKPELCANPEEGWVQNLMRRLDQPPAPGKQSPGCRKNRGT
SKSGKKGKGSKGCKRTEQTQPSRG

FIG. 15C mCCL21ser-TG

The STOP codon (TAG) is taken out from the murine CCL21 serine sequence
(mCCL21ser) and is added at the end of the transglutaminase substrate sequence (TG):
mCCL21ser – TG – stop

*cDNA*

ATGGCTCAGATGATGACTCTGAGCCTCCTTAGCCTGGTCCTGGCTCTCTGCAT
CCCCTGGACCCAAGGCAGTGATGGAGGGGGTCAGGACTGCTGCCTTAAGTAC
AGCCAGAAGAAAATTCCCTACAGTATTGTCCGAGGCTATAGGAAGCAAGAAC
CAAGTTTAGGCTGTCCCATCCCGGCAATCCTGTTCTCACCCCGGAAGCACTCT
AAGCCTGAGCTATGTGCAAACCCTGAGGAAGGCTGGGTGCAGAACCTGATGC
GCCGCCTGGACCAGCCTCCAGCCCCAGGGAAACAAAGCCCCGGCTGCAGGA
AGAACCGGGGAACCTCTAAGTCTGGAAAGAAAGGAAAGGGCTCCAAGGGCT
GCAAGAGAACTGAACAGACACAGCCCTCAAGAGGAAACCAGGAGCAGGTGA
GCCCCCTGTAG

FIG. 16A mCCL21ser-TG

*Protein translation*

MAQMMTLSLLSLVLALCIPWTQGSDGGGQDCCLKYSQKKIPYSIVRGYRKQEPS
LGCPIP
AILFSPRKHSKPELCANPEEGWVQNLMRRLDQPPAPGKQSPGCRKNRGTSKSGK
KGKGSKGCKRTEQTQPSRGNQEQVSPL*

FIG. 16B mCCL21ser-PlCl-TG

The STOP codon (TAG) is taken out from the murine CCL21 serine sequence (mCCL21ser) and is added at the end of the transglutaminase substrate sequence (TG) while the plasmin degradable linker sequence (PlCl) is added between the mCCL21ser and the TG sequence: mCCL21ser – PlCl - TG - stop

*cDNA*

ATGGCTCAGATGATGACTCTGAGCCTCCTTAGCCTGGTCCTGGCTCTCTGCAT
CCCCTGGACCCAAGGCAGTGATGGAGGGGGTCAGGACTGCTGCCTTAAGTAC
AGCCAGAAGAAAATTCCCTACAGTATTGTCCGAGGCTATAGGAAGCAAGAAC
CAAGTTTAGGCTGTCCCATCCCGGCAATCCTGTTCTCACCCCGGAAGCACTCT
AAGCCTGAGCTATGTGCAAACCCTGAGGAAGGCTGGGTGCAGAACCTGATGC
GCCGCCTGGACCAGCCTCCAGCCCCAGGGAAACAAAGCCCCGGCTGCAGGA
AGAACCGGGGAACCTCTAAGTCTGGAAAGAAAGGAAAGGGCTCCAAGGGCT
GCAAGAGAACTGAACAGACACAGCCCTCAAGAGGACCCGTGGAGCTGCCCC
TGATCAAGATGAAGCCCAACCAGGAGCAGGTGAGCCCCCTGTAG

FIG. 17A

*Protein translation*

MAQMMTLSLLSLVLALCIPWTQGSDGGGQDCCLKYSQKKIPYSIVRGYRKQEPS
LGCPIPAILFSPRKHSKPELCANPEEGWVQNLMRRLDQPPAPGKQSPGCRKNRGT
SKSGKKGKGSKGCKRTEQTQPSRGPVELPLIKMKPNQEQVSPL*

FIG. 17B hCCL21-TG

The STOP codon (TAG) is taken out from the human CCL21 sequence (hCCL21) and is added at the end of the transglutaminase substrate sequence (TG) :hCCL21 – TG - stop

*cDNA*

ATGGCTCAGTCACTGGCTCTGAGCCTCCTTATCCTGGTTCTGGCCTTTGGCAT
CCCCAGGACCCAAGGCAGTGATGGAGGGGCTCAGGACTGTTGCCTCAAGTAC
AGCCAAAGGAAGATTCCCGCCAAGGTTGTCCGCAGCTACCGGAAGCAGGAA
CCAAGCTTAGGCTGCTCCATCCCAGCTATCCTGTTCTTGCCCCGCAAGCGCTC
TCAGGCAGAGCTATGTGCAGACCCAAAGGAGCTCTGGGTGCAGCAGCTGATG
CAGCATCTGGACAAGACACCATCCCCACAGAAACCAGCCCAGGGCTGCAGG
AAGGACAGGGGGGCCTCCAAGACTGGCAAGAAAGGAAAGGGCTCCAAAGGC
TGCAAGAGGACTGAGCGGTCACAGACCCCTAAAGGGCCAAACCAGGAGCAG
GTGAGCCCCCTGTAG

FIG. 18A

*Protein translation*

MAQSLALSLLILVLAFGIPRTQGSDGGAQDCCLKYSQRKIPAKVVRSYRKQEPSL
GCSIP
AILFLPRKRSQAELCADPKELWVQQLMQHLDKTPSPQKPAQGCRKDRGASKTG
KKGKGSKGCKRTERSQTPKGPNQEQVSPL*

FIG. 18B hCCL21- PlCl - TG

The STOP codon (TAG) is taken out from the human CCL21 sequence (hCCL21) and is added at the end of the transglutaminase substrate sequence (TG) while the plasmin degradable linker sequence (PlCl) is added between the hCCL21 and the TG sequence:
hCCL21 – PlCl - TG - stop

*cDNA*

ATGGCTCAGTCACTGGCTCTGAGCCTCCTTATCCTGGTTCTGGCCTTTGGCAT
CCCCAGGACCCAAGGCAGTGATGGAGGGGCTCAGGACTGTTGCCTCAAGTAC
AGCCAAAGGAAGATTCCCGCCAAGGTTGTCCGCAGCTACCGGAAGCAGGAA
CCAAGCTTAGGCTGCTCCATCCCAGCTATCCTGTTCTTGCCCCGCAAGCGCTC
TCAGGCAGAGCTATGTGCAGACCCAAAGGAGCTCTGGGTGCAGCAGCTGATG
CAGCATCTGGACAAGACACCATCCCCACAGAAACCAGCCCAGGGCTGCAGG
AAGGACAGGGGGGCCTCCAAGACTGGCAAGAAAGGAAAGGGCTCCAAAGGC
TGCAAGAGGACTGAGCGGTCACAGACCCCTAAAGGGCCACCCGTGGAGCTG
CCCCTGATCAAGATGAAGCCCAACCAGGAGCAGGTGAGCCCCCTGTAG

FIG. 19A

*Protein translation*

MAQSLALSLLILVLAFGIPRTQGSDGGAQDCCLKYSQRKIPAKVVRSYRKQEPSL
GCSIPAILFLPRKRSQAELCADPKELWVQQLMQHLDKTPSPQKPAQGCRKDRGA
SKTGKKGKGSKGCKRTERSQTPKGPPVELPLIKMKPNQEQVSPL*

FIG. 19B

Human CCL21

*Recommended name:*
   C-C motif chemokine 21
*Alternative name(s):*
   Small-inducible cytokine A21
   Beta chemokine exodus-2
   6Ckine
   Secondary lymphoid-tissue chemokine
     Short name=SLC

*NCBI Reference Sequence: NC_000009.11*
*Homo sapiens chromosome 9, GRCh37 primary reference assembly*

ATCCCAGCCCACGCACAGACCCCCAACTTGCAGCTGCCCACCTCACCCTCAG
CTCTGGCCTCTTACTCACCCTCTACCACAGACATGGCTCAGTCACTGGCTCTG
AGCCTCCTTATCCTGGTTCTGGCCTTTGGCATCCCCAGGACCCAAGGTACCAA
GGCAGGGAGGGGCCTTGCATGGGGCTAAGGGGATCAAGAGGCCTGGATAGG
AGCTTGCCAGCAGCCCTGGCTCCCTGTGAATCCCACCCTGCAGGCAGTGAT
GGAGGGGCTCAGGACTGTTGCCTCAAGTACAGCCAAAGGAAGATTCCCGCCA
AGGTTGTCCGCAGCTACCGGAAGCAGGAACCAAGCTTAGGCTGCTCCATCCC
AGCTATCCTGTGAGTGGACACAAAGGGGTGGGTACTGGCTGGTGACGGGGTG
GGGAGGGCATGGTGGGCAAGACTAAGAAGGCTTACTAGCCCCCACCCGCAG
GTTCTTGCCCCGCAAGCGCTCTCAGGCAGAGCTATGTGCAGACCCAAAGGAG
CTCTGGGTGCAGCAGCTGATGCAGCATCTGGACAAGACACCATCCCCACAGA
AACCAGCCCAGGGCTGCAGGAAGGACAGGGGGGCCTCCAAGACTGGCAAGA
AAGGAAAGGGCTCCAAAGGCTGCAAGAGGTGAGGAATCTGAGGGATGTGGG
TAAAGGGGAGCCTCAGTCAGCCCCTCACACCCCTCTTCTGCCCTCACAGGACT
GAGCGGTCACAGACCCCTAAAGGGCCATAGCCCAGTGAGCAGCCTGGAGCC
CTGGAGACCCCACCAGCCTCACCAGCGCTTGAAGCCTGAACCCAAGATGCAA
GAAGGAGGCTATGCTCAGGGGCCCTGGAGCAGCCACCCCATGCTGGCCTTGC
CACACTCTTTCTCCTGCTTTAACCACCCCATCTGCATTCCCAGCTCTACCCTGC
ATGGCTGAGCTGCCCACAGCAGGCCAGGTCCAGAGAGACCGAGGAGGGAGA
GTCTCCCAGGGAGCATGAGAGGAGGCAGCAGGACTGTCCCCTTGAAGGAGA
ATCATCAGGACCCTGGACCTGATACGGCTCCCCAGTACACCCCACCTCTTCCT
TGTAAATATGATTTATACCTAACTGAATAAAAAGCTGTTCTGTCTTCCCACCC
AA

FIG. 20A

Human CCL21

*Coding region:*

ATGGCTCAGTCACTGGCTCTGAGCCTCCTTATCCTGGTTCTGGCCTTTGGCAT
CCCCAGGACCCAAGGCAGTGATGGAGGGGCTCAGGACTGTTGCCTCAAGTAC
AGCCAAAGGAAGATTCCCGCCAAGGTTGTCCGCAGCTACCGGAAGCAGGAA
CCAAGCTTAGGCTGCTCCATCCCAGCTATCCTGTTCTTGCCCCGCAAGCGCTC
TCAGGCAGAGCTATGTGCAGACCCAAAGGAGCTCTGGGTGCAGCAGCTGATG
CAGCATCTGGACAAGACACCATCCCCACAGAAACCAGCCCAGGGCTGCAGG
AAGGACAGGGGGGCCTCCAAGACTGGCAAGAAAGGAAAGGGCTCCAAAGGC
TGCAAGAGGACTGAGCGGTCACAGACCCCTAAAGGGCCATAG

*UniProtKB/Swiss-Prot O00585 (CCL21_HUMAN)*

FIG. 20B

Human CCL21

MAQSLALSLLILVLAFGIPRTQGSDGGAQDCCLKYSQRKIPAKVVRSYRKQEPSL
GCSIPAILFLPRKRSQAELCADPKELWVQQLMQHLDKTPSPQKPAQGCRKDRGA
SKTGKKGKGSKGCKRTERSQTPKGP

FIG. 20C

CCR7 LIGAND DELIVERY AND CO-DELIVERY IN IMMUNOTHERAPY

CROSS REFERENCE TO RELATED APPLICATIONS

This application claims priority to U.S. provisional patent application U.S. Ser. No. 61/303,442 filed Feb. 11, 2010, which is hereby incorporated by reference herein.

FIELD OF THE INVENTION

The Field of the invention relates to the field of immunology, and how to induce immune tolerance to allografts and xenografts. In some aspects, the creation of tolerance also relates to manufacture and use of medicaments containing biotherapeutics such as proteins, and the use of nucleic acid sequences.

BACKGROUND

The receptor CC-chemokine receptor 7 (CCR7) is known to play an important role in balancing immunity and tolerance, in particular self-tolerance (Förster, Davalos-Misslitz et al. 2008). Its two ligands, CC-chemokine ligand-19 (CCL19) and -21 (CCL21) play an important role in immunity and inflammation. In particular, CCR7 and its ligands seem to play an important role in homing of subpopulations of T cells and antigen-presenting cells like dendritic cells (DCs) to the lymph nodes (LNs). The lymph nodes are implicated as locations for development of both protective immunity to exogenous antigens and tolerance to self-antigens, and in guiding the interactions between such cell types that lead to T cell education.

In the scientific literature, CCL19 and CCL21, along with their receptor CCR7, have been shown to be generally necessary in the establishment of self-tolerance, both in physiological and pathophysiology situations. For example, mice that are deficient in CCR7 are prone to develop generalized multi-organ autoimmunity, characterized by lymphocyte infiltrates in peripheral organs, circulating autoantibodies, and IgG deposition on renal glomeruli (Davalos-Misslitz, Rieckenberg et al. 2007). Furthermore, mice that lack CCR7 ligands, plt mice, show defective migration of naïve T cells and activated dendritic cells to the lymph nodes, show delayed but ultimately enhanced T cell activation as measured by antigen-specific T cell proliferation and cytokine production. These T cell responses were shifted from the lymph node to the spleen (Mori, Nakano et al. 2001). A later study showed prolong expansion of antigen-specific CD4+ T cells in the draining lymph nodes of plt mice compared to wild-type mice after immunization due to activation-induced cell death by CCR7 ligands (Yasuda, Kuwabara et al. 2007), while another study showed that CCR7 signaling inhibits T cell proliferation (Ziegler, Oberbarnscheidt et al. 2007). Together, these data from the literature show CCR7-dependent migration of cells to be required for maintaining tolerance to self-antigens, but redundant for mounting cytotoxic T cell responses.

SUMMARY OF THE INVENTION

The literature on the roles of CCR7 ligands in tumor immunity vs. tolerance, and in autoimmune diseases, is contradictory. CCL19 and CCL21, along with their receptor CCR7, seem to be associated with the development of self-tolerance. And, on the one hand, CCR7 ligands are important for the development of secondary and tertiary lymphoid organs (Ohl, Mohaupt et al. 2004), which play a role in autoimmune diseases and promote lymphocytic infiltration. For example, CCL21 is increased in autoimmune thyroid disease, and transgenic mice expressing CCL21 constitutively in the thyroid develop lymphocyte recruitment, germinal centers, and autoimmunity (Martin, Coronel et al. 2004). Consistent with this, some murine tumors expressing CCL21 showed delayed progression, increased numbers of CD4+ and CD8+ T cells, and local anti-tumor immunity (Nomura, Hasegawa et al. 2001). Other reports have similarly demonstrated enhanced anti-tumor immune responses after CCL21 or CCL19 injection directly into the tumor or by induced tumor cell expression of these cytokines (Braun, Chen et al. 2000; Sharma, Stolina et al. 2000; Vicari, Ait-Yahia et al. 2000; Kirk, Hartigan-O'Connor et al. 2001; Ashour, Lin et al. 2007; Turnquist, Lin et al. 2007).

On the other hand, other studies have shown immunosuppressive effects of CCL19. In one study, an systemic delivery of IgG-CCL19 fusion protein induced immunosuppressive effects in delayed-type hypersensitivity and reduced rejection of transplanted solid organs (Ziegler, Gueler et al. 2006); it was hypothesized that this rejection was due to disrupted trafficking of dendritic cells and T cells as well as a general inhibition of T cell proliferation (Ziegler, Gueler et al. 2006). In another study by the same group, plasmocytoma tumor cells that were engineered to over-express CCL19-IgG fusion protein showed prolonged tumor survival as allografted tumors, i.e., in MHC-mismatched recipients (Krautwald, Ziegler et al. 2004). These publications teach that the tumor recruited dendritic cells into the tumor and prevented them from trafficking to the lymph node to activate T cells there, thereby preventing an anti-tumor adaptive immune response to be mounted.

It is demonstrated herein, by contrast, that local administration of CCR7 ligand CCL21 can induce tolerance to allografts, and also xenografts, rather than merely impair the allo- or xenoimmune response. Herein, certain embodiments utilize CCL19 and CCL21 to induce immune tolerance to HLA mismatched allografts and even to xenografts. In animal models, this corresponds to induction of immune tolerance to non-syngeneic allografts, i.e. across strains of the same species, and to xenografts, i.e. across species boundaries. This invention has a number of applications, related to cell and tissue transplantation, as described herein.

Embodiments include administration of or expression of an effective amount of CCL19 and/or CCL21. In the mouse, CCL21 exists in two isoforms, CCL21ser and CCL21leu, which differ in one amino acid residue. CCL21ser is most abundant in the lymph nodes and is secreted by lymph node stromal cells, while CCL21leu is expressed by lymphatic endothelial cells on peripheral lymphatic vessels. Both forms are CCR7 ligands and are expected to behave similarly in the context of this invention. In the human, only one isoform exists. The human isoform and variations thereof may be used. For instance, conservative substitutions may be employed.

Embodiments include the use of ligands for CCR7 as tolerogenic agents for development of allotolerance and even xenotolerance. Conventional wisdom (e.g., the Krautwald/Ziegler references, teaching immunosuppression without adaptive immunity responses or tolerization) teaches that trapping dendritic cells in the area is the goal. But, in fact and as described herein, CCL19 and/or CCL21 may be used to induce actual tolerization. Moreover, these ligands may be introduced and/or maintained locally (as opposed to systemically).

BRIEF DESCRIPTION OF THE FIGURES

FIG. 15A: Murine CCL21 leucine (mCCL21leu)/CCL21b. SEQ ID NO:15. Three genes code for CCL21 in mouse. Ccl21a and Ccl21c produce identical proteins while the protein produced by Ccl21b differs at only one position. Ccl21a and Ccl21c have Leu-65 (6Ckine-Leu) while Ccl21b has Ser-65 (6Ckine-Ser), FIG. 15B: Murine CCL21 leucine (mCCL21leu)/CCL21b coding region. SEQ ID NO:16.

FIG. 15C: Murine CCL21 protein. SEQ ID NO:17.

FIG. 16A: mCCL21ser-TG. The STOP codon (TAG) is taken out from the murine CCL21 serine sequence (mCCL21ser) and is added at the end of the transglutaminase substrate sequence (TG): mCCL21ser-TG-stop. SEQ ID NO:18.

FIG. 16B: Protein translation of FIG. 16A. SEQ ID NO:19

FIG. 17A: mCCL21ser-P1C1-TG. The STOP codon (TAG) is taken out from the murine CCL21 serine sequence (mCCL21ser) and is added at the end of the transglutaminase substrate sequence (TG) while the plasmin degradable linker sequence (P1C1) is added between the mCCL21ser and the TG sequence: mCCL21ser-P1C1-TG-stop. SEQ ID NO:20.

FIG. 17B: Protein translation of FIG. 17A. SEQ ID NO:21.

FIG. 18A: hCCL21-TG. The STOP codon (TAG) is taken out from the human CCL21 sequence (hCCL21) and is added at the end of the transglutaminase substrate sequence (TG) :hCCL21-TG-stop. SEQ ID NO:22.

FIG. 18B: Protein translation of FIG. 18A. SEQ ID NO:23.

FIG. 19A: hCCL21-P1C1-TG. The STOP codon (TAG) is taken out from the human CCL21 sequence (hCCL21) and is added at the end of the transglutaminase substrate sequence (TG) while the plasmin degradable linker sequence (P1C1) is added between the hCCL21 and the TG sequence: hCCL21-P1C1-TG-stop. SEQ ID NO:24.

FIG. 19B: Protein translation of FIG. 18A. SEQ ID NO:25.

FIG. 20A: Human CCL21, NCBI Reference Sequence: NC_000009.11; SEQ ID NO:26.

FIG. 20B: Coding region for FIG. 20A; SEQ ID NO:27

FIG. 20C: Protein sequence for CCL21; SEQ ID NO:28

DETAILED DESCRIPTION OF PREFERRED EMBODIMENTS OF THE INVENTION

Figure 1:
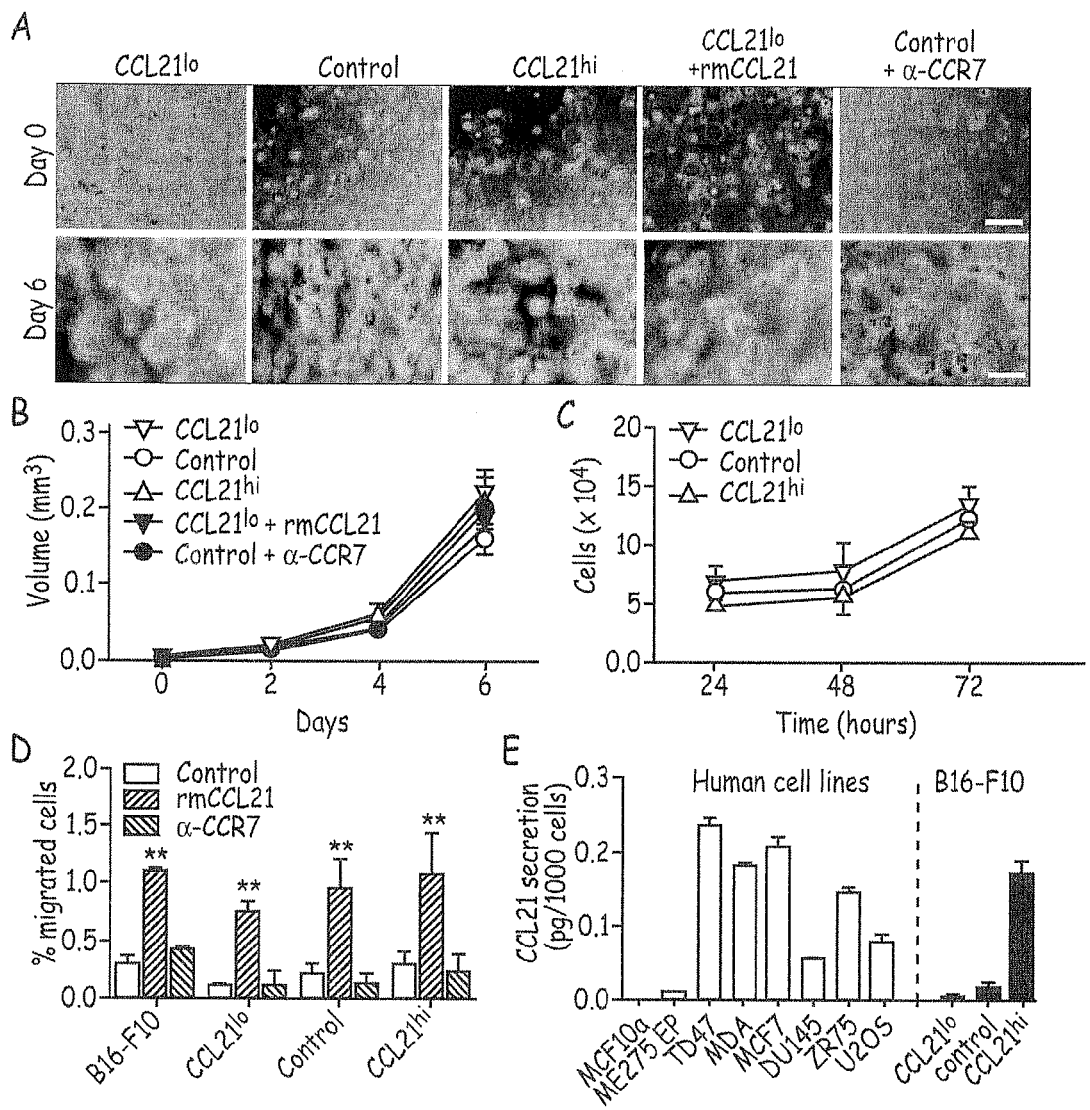
FIG. 1: Engineered tumor cells have similar growth and CCR7 response in vitro. (A-B) Images and quantification of spheroid formation of tumors cultured in 3D collagen matrices after 6 days. Bar, 100 μm. (C) Tumor cell proliferation after indicated time in 3D culture. (D) All engineered cell lines had functional CCR7 and exhibited chemotaxis towards exogenous CCL21 (500 ng/ml in a Boyden chamber assay). Responses were not different between cell lines but were CCR7-dependent since CCR7 neutralization reduced migration to basal levels. (E) CCL21 secretion by normal and tumor human cell lines and B16-F10 melanomas in vitro. **$P<0.01$.

The ligands CCL19 and CCL21 may be used to develop tolerance. A series of experiments are described herein to demonstrate such use. This use is surprising for a variety of reasons, including a body of literature that teaches away from this use. Theories are set forth to provide a theoretical basis for understanding why these ligands are effective. These theories, however, are not limiting in terms of the scope of the invention and how the ligands may be made and used.

One theory of operation revolves around the role of CCL19 and CCL21 in cancer tolerization. In overview, the theory is that CCR7 ligands such as CCL21 drive a "lymph node mimicry" by tumors that induces immunological tolerance. Tumor manipulation of host immunity is important for tumor survival and invasion. A mechanism of immune escape was introduced wherein tumors can mimic the structural features of the T cell zone of the lymph node to modulate the immune response. B16 melanomas, along with other invasive tumors, secrete CCL21, a lymphoid chemoattractant for naïve T cells and RORgt$^+$ lymphoid tissue inducer (LTi) cells. These tumors, and CCL21-overexpressing but not knockdown (CCL21$^{lo}$) variants, developed a reticular stromal network and high endothelial venule-like vessels; their T cell populations became polarized towards regulatory phenotypes while CCL21$^{lo}$ tumors induced antigen-specific immunity. The CCL21-mediated immune tolerization was host CCR7-dependent, and could protect co-implanted CCL21$^{lo}$ tumors and even nonsyngenic tumor allografts from rejection. In contrast to conventional wisdom, it is suggested herein that: by guiding T cell education in their immunosuppressive microenvironment, CCL21-secreting tumors shift the host immune response from immunogenic to tolerogenic, facilitating growth and invasion. This theory is elaborated in more detail as follows.

The lymphoid chemokines CCL21 and CCL19 play essential roles in leukocyte trafficking into lymphatics and to lymph nodes (LNs)(Ebert et al., Förster et al., Johnson et al.).

Within the lymph node paracortex, CCL21 and CCL19 expression by specialized stromal cells called fibroblastic reticular cells (FRCs) attracts CCR7+ leukocytes, including mature DCs, macrophages, and naïve T cells, and guides the interactions needed for T cell education and priming (Davalos-Misslitz et al). These CCR7-dependent interactions are not only important for the initiation of an effective immune response, but are also key to the induction of peripheral tolerance (Johnson, Davalos-Misslitz et al, Menning et al.), and loss of CCR7 signaling is associated with spontaneous autoimmunity (Förster et al., Menning et al.). Tumor expression of CCR7 is strongly correlated with lymph node metastasis and poor prognosis in many human cancers (Cabioglu et al., Ding et al., Wiley, et al.), which may help to explain lymph node-specific homing of these cancers. However, immunological tolerance is required for tumor cell survival and growth in lymphoid tissues, and merely expressing CCR7 does not account for immune evasion or escape. It was recently shown that invasive tumor cells expressing CCR7 also secrete its ligands when cultured in three-dimensional cultures (Shields et al.).

Formation of Cell Line Models

B16-F10 melanomas (also referred to as F10 herein) maintain similar levels of CCL21 in vivo as do lymph nodes. Three stable cell sublines were engineered from murine B16-F10 melanomas to either knockdown the secretion of CCL21 by lentiviral transduction of shRNA ($CCL21^{lo}$), express endogenous levels of the chemokines (scrambled shRNA control), or over-express CCL21 ($CCL21^{hi}$). In vitro, lentiviral transduction and CCL21 expression did not affect proliferation, three-dimensional (3D) spheroid formation, CCR7 expression, or migration up a gradient of exogenous CCL21; furthermore, the addition of exogenous CCL21 to $CCL21^{lo}$ tumor cells or CCR7 neutralization to control tumor cells had no effect on these in vitro behaviors (FIG. 1A-D). When implanted into C57BL/6 mice, control and $CCL21^{hi}$ tumors after 9 days contained similar CCL21 protein levels as those found in the LN (FIG. 2A). CCL21 protein was also found in a number of invasive human tumor cell lines when cultured in 3D conditions (FIG. 1 Panel E). Thus, because of their similar behavior in vitro, these three engineered cell lines could be used as tools specifically to study the role of tumor CCL21 expression on host response to the tumors.

Knockdown of CCL21 Leads to CCR7-Dependent Suppressed Tumor Growth In Vivo

Figure 2:
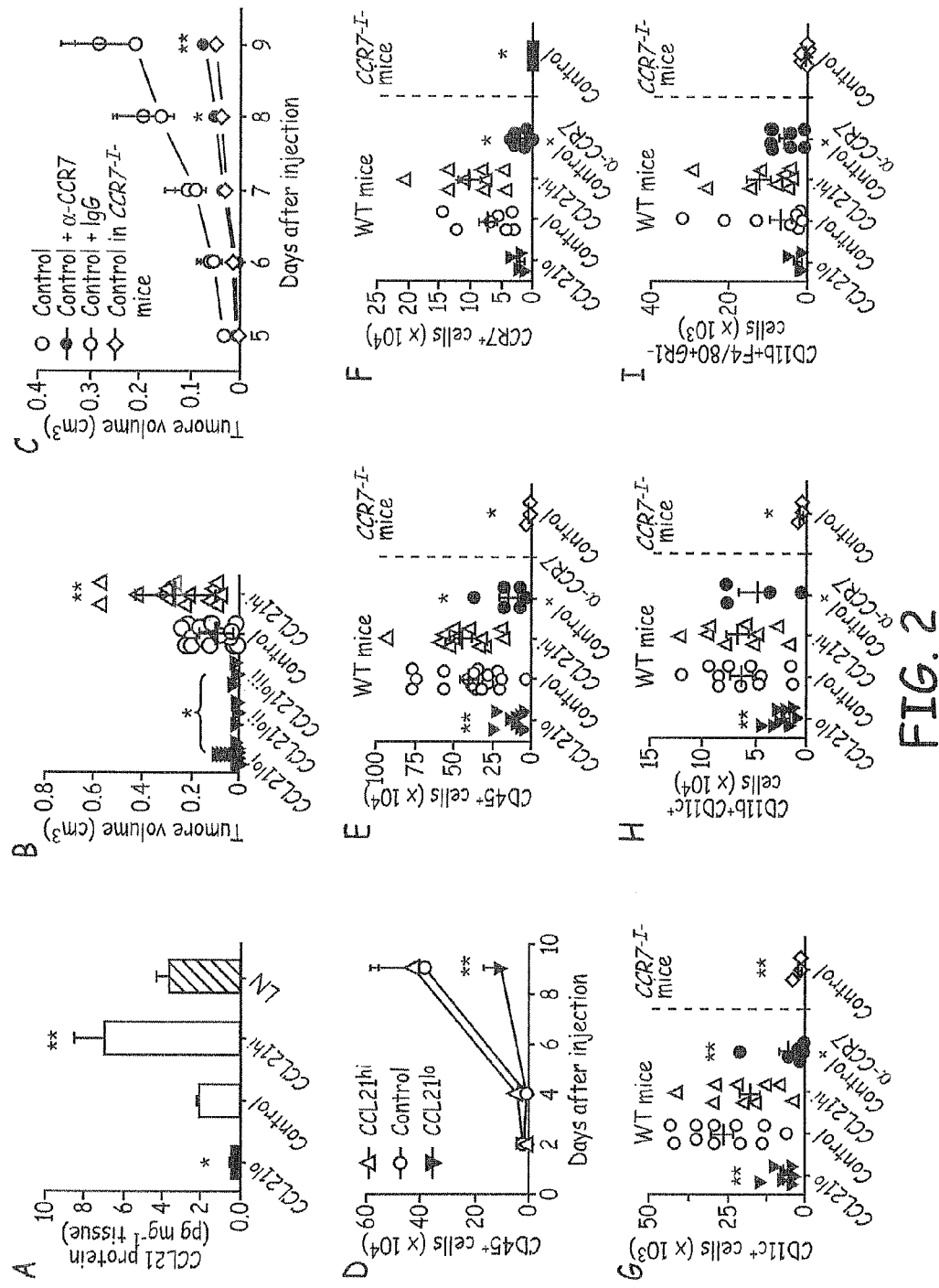
FIG. 2: CCL21 expression promotes tumor growth that is host CCR7-dependent. (A) CCL21 protein from day 9 tumor and lymph node lysates. (B) Volume of tumors explanted at day 9 (n=3, bar shows median). Multiple CCL21 lone clones were implanted (CCL21$^{lo}$ i, clone 21/217; clone CCL21$^{lo}$ ii, clone 21/217 D8; Clone CCL21$^{lo}$ iii, clone 21/401 H5). (C) Day 9 control tumor volumes in wildtype mice treatment with CCR7 neutralizing antibody or control IgG, or in CCR7$^{-/-}$ mice. (D) Timecourse of CD45$^+$ leukocyte infiltration into tumors. (E-I) Intratumor infiltration of CD45$^+$ leukocyte subpopulations at day 9 in wildtype or CCR7$^{-/-}$ mice as indicated (bar shows median). In all cases, *$P<0.05$, **$P<0.01$ relative to controls using one-way ANOVA and Bonferroni post-test.
Figure 3:
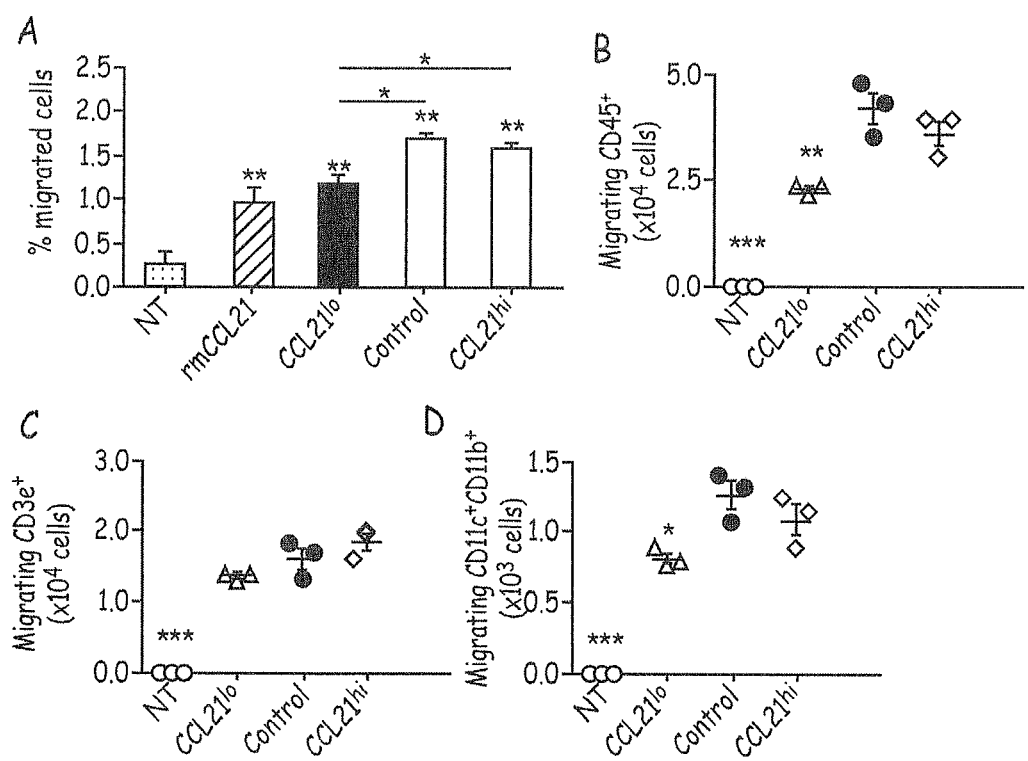
FIG. 3: CCL21-secreting tumors recruit CCR7$^+$ immune cells in vitro. (A) Comparison of peritoneal macrophage migration towards rmCCL21, CCL21$^{lo}$, control, and CCL21$^{hi}$ tumor cells in vitro. (B-D) Control and CCL21$^{hi}$ tumor cells stimulated (B) leukocyte, (C) T cell, and (D) dendritic cell migration in vitro. *$P<0.05$, **$P<0.01$ compared with control.

When implanted into immune competent syngeneic C57BL/6 mice, CCL21-secreting orthotopic tumors grew significantly larger than various $CCL21^{lo}$ tumor clones (FIG. 2 Panel B). Systemic neutralization of CCR7 with blocking antibodies or inoculation of control tumor cells into C57BL/6 $CCR7^{-/-}$ mice resulted in significantly impaired tumor growth (FIG. 2 Panel C), indicating that the host CCR7 was critical for the higher growth rates of CCL21-secreting tumors. Control and $CCL21^{hi}$ tumors attracted more CD45+ leukocytes than $CCL21^{lo}$ tumors (FIG. 2 Panel D) as well as control tumors grown in $CCR7^{-/-}$ mice (FIG. 2 Panel E). Similarly, antigen presenting cells (APCs) and CD11b+F4/80+GR1− macrophages were preferentially attracted to control and $CCL21^{hi}$ tumors (FIG. 2 Panels F-I); this was confirmed in vitro comparing the migration of splenocytes from naïve mice towards the different tumor types (FIG. 3). These responses were host CCR7-dependent (FIG. 2 Panels F-I). It was hypothesized that CCL21 modulation of the immunological compartment within the tumor microenvironment was playing a significant role in the differential tumor propagation observed.

Figure 4:
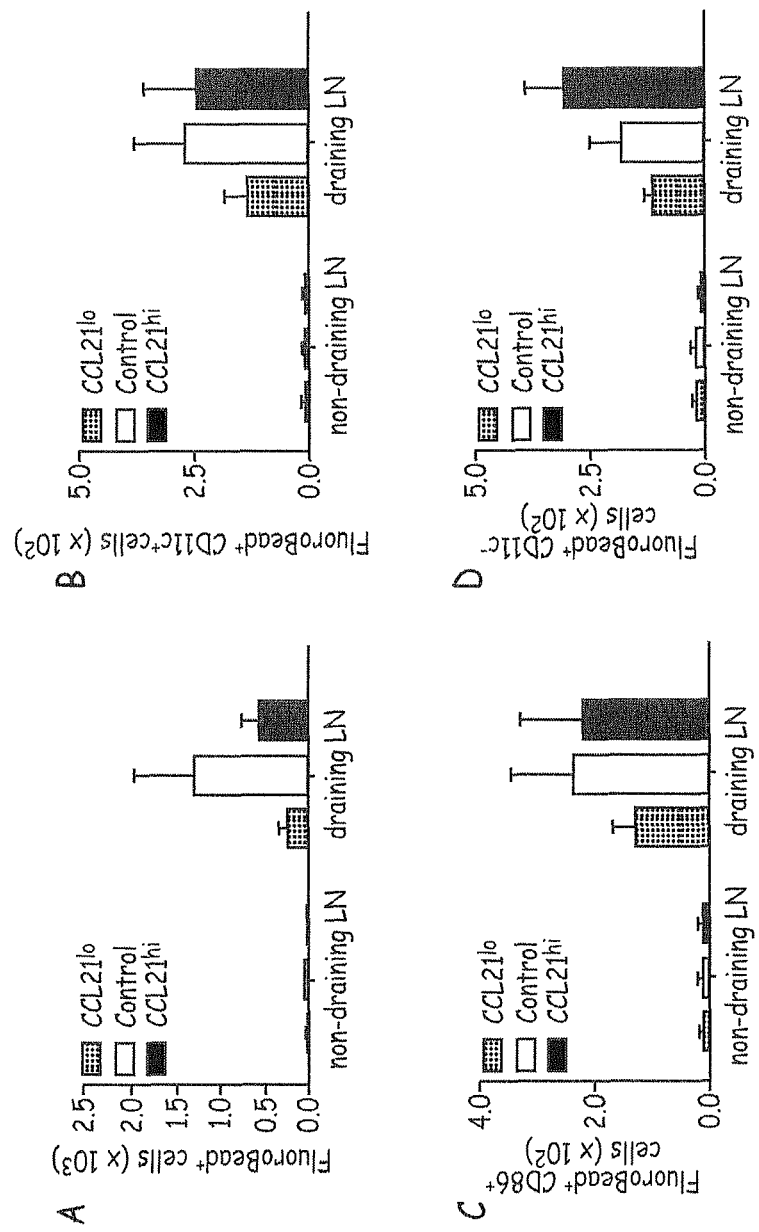
FIG. 4: Dendritic cells traffic from tumors to draining lymph nodes. FITC$^+$ immune cells were quantified following intratumoral injection with FITC-labeled microspheres. (A) FITC$^+$CD45$^+$ leukocytes, (B) subset of CD11c$^+$ dendritic cells, (C) subset of CD11c$^+$CD86$^+$ mature dendritic cells, and (D) subset of CD11c$^-$ cells within naïve lymph nodes vs. tumor-draining brachial lymph nodes.

To test whether DCs were accumulating in the tumor tissue, unable to escape and mount an immune response (Ziegler et al., 2006), FITC-conjugated microspheres were injected into the tumor and examined FITC+ DCs in the draining lymph node after 24 h. More FITC+ macrophages and DCs in lymph nodes draining control and $CCL21^{hi}$ tumors were actually found than those draining $CCL21^{lo}$ tumors, although these differences were not statistically significant (FIG. 4); therefore there was no apparent impairment in DC trafficking from CCL21-expressing tumors.

This result was surprising because it was an apparent paradox—increased tumor growth (indicating immunoprivilege) that was nonetheless associated with increased leukocyte attraction with normal trafficking (indicating immunoattack).

Figure 5:
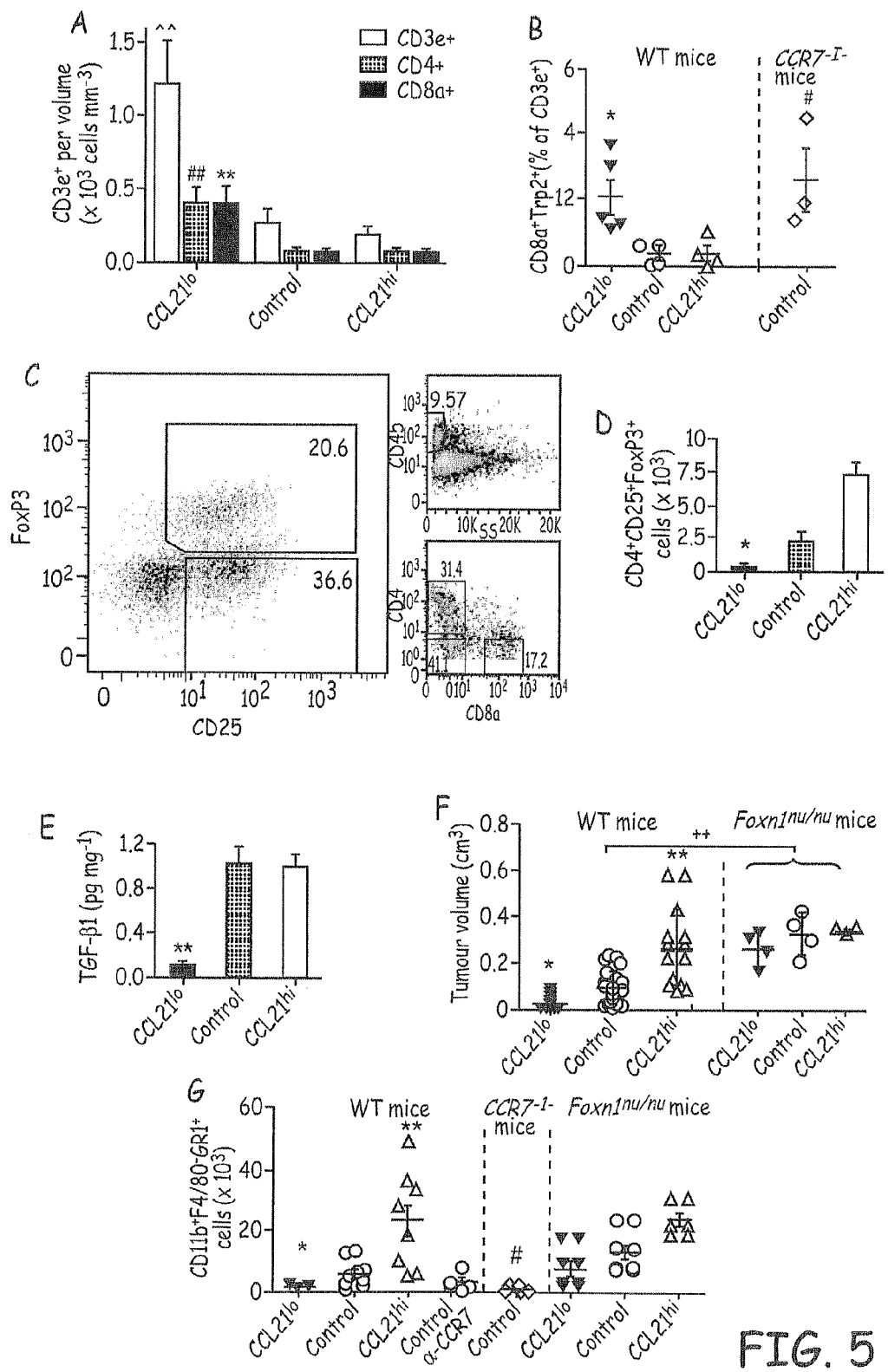
FIG. 5: CCL21 expression leads to a regulatory environment. (A) Intratumoral CD3e$^+$ T cell populations. (B) Tetramer staining for the tumor-associated antigenic sequence of the tyrosinase related protein 2, SVYDFFVWL (SEQ ID NO: 29) (Trp2$_{180-188}$), by CD19$^-$CD3e$^+$CD8a$^+$Trp2$^+$ T cells in wildtype and CCR7$^-$ mice. (C) Representative flow cytometry plot and (D) quantification of intratumoral Treg infiltrates. (E) Total TGF-β$_1$ protein levels within tumors. (F) Comparison of tumor volumes in wildtype vs. athymic mice that lack adaptive immunity. (G) CD11b$^+$F4/80$^-$GR-1$^+$ infiltrates in wildtype vs. athymic mice. All data were taken at day 9. *,#$P<0.05$; **,^^,++$P<0.01$ compared with respective controls.
Figure 6:
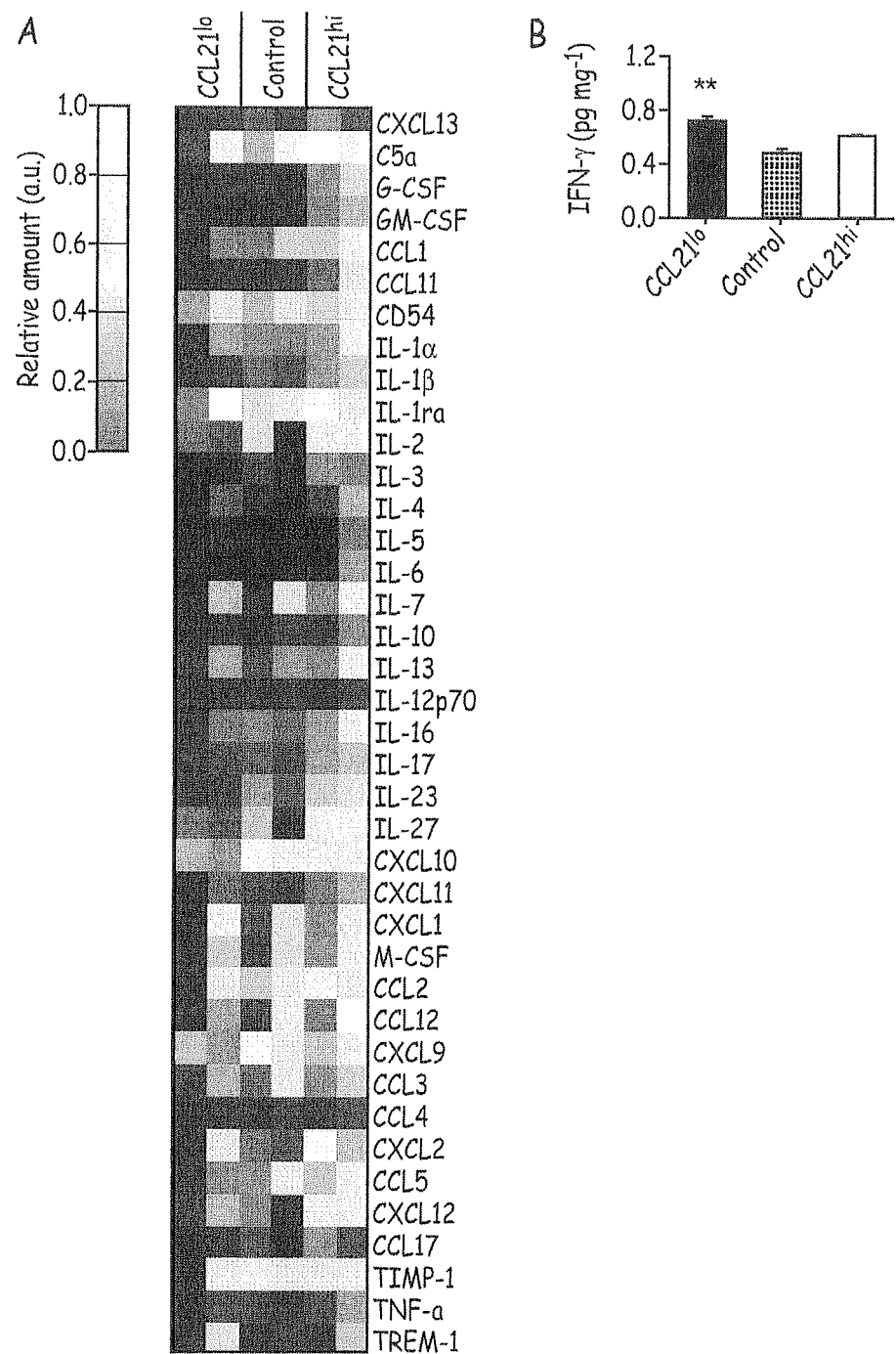
FIG. 6: CCL21 drives modulation of the tumor cytokine milieu. (A) Cytokine array results from day 9 tumor lysates (n=2). (B) Quantification of IFN-γ secretion by CCL21$^{lo}$, control, and CCL21$^{hi}$ tumors.

Tumor CCL21 Leads to Shifts in T Cell Populations from Immunogenic to Tolerogenic To more accurately define the roles of tumor-derived CCL21 in modulating tumor immune responses, T cell populations were examined within the different tumors. While control and $CCL21^{hi}$ tumors attracted more CD45+ leukocytes overall, $CCL21^{lo}$ tumors contained a higher fraction of T cells (FIG. 5 Panel A) and tyrosinase related protein 2 (Trp-2) antigen-specific T cells (FIG. 5 Panel B). In contrast, control and $CCL21^{hi}$ tumors contained larger fractions (and total numbers) of CD4+CD25+FoxP3+ regulatory T cells (FIG. 5 Panels C-D). When tumors were digested and analyzed for chemokine expression, a drastic elevation of TGF-$\beta_1$ in control and $CCL21^{hi}$ tumors (FIG. 5 Panel E) were found, which is central to both the initiation of T cell senescence within a tumor (Montes et al.) and the induction of functional regulatory T cells subsets (Montes et al). Protein cytokine arrays (FIG. 6 Panel A) further supported the notion of a functional immune switch, illustrating a coincident shift in the chemokine environment of control and $CCL21^{hi}$ tumors. Salient differences between $CCL21^{lo}$ and $CCL21^{hi}$ tumors included CXCL9 and CXCL10 (both CXCR3 ligands implicated in monocyte, DC, and T cell recruitment), IL-1ra (an endogenous IL-1 inhibitor), CCL2 (which is strongly associated with melanoma progression and immune escape) (Ilkovitch et al.), C5a (associated with enhanced tumor growth) (Markiewski et al.) and IL-27 (which inhibits $T_H17$ and promotes $T_H2$ responses); in contrast, IFN-γ, which is often associated with a cytotoxic T cell response (Dunn et al.), was higher in $CCL21^{lo}$ tumors (FIG. 6 Panel B).

The central role of the adaptive immune response in CCL21-mediated tumor development was confirmed using athymic $Foxn1^{nu/nu}$ mice, which lack the adaptive immune compartment. In these mice, all tumor types, irrespective of CCL21 levels, grew large (FIG. 5 Panel F). The differential recruitment of CD11b+F4/80−GR1+ immature myeloid cells (which display features of undifferentiated myeloid cells and myeloid subset precursors and which are implicated in tumor progression (Kusmartsev et al.) to control and $CCL21^{hi}$ tumors, was conserved in both athymic and wildtype mice (FIG. 5 Panel G). This further demonstrated that tumor development or rejection relies on adaptive rather than innate immune functions.

Together, these data indicated that CCL21 secretion by tumors promotes a tolerogenic cytokine milieu and recruitment of suppressor myeloid cells, helping to drive a T cell repertoire with regulatory rather than effector functions and with the capacity to dampen anti-tumor immune activity. In contrast, the suppression of CCL21 permits an antigen-specific anti-tumor T cell response.

CCL21 Secreting Tumors Develop some Features of the Lymphoid T-Cell Zone

Figure 7:
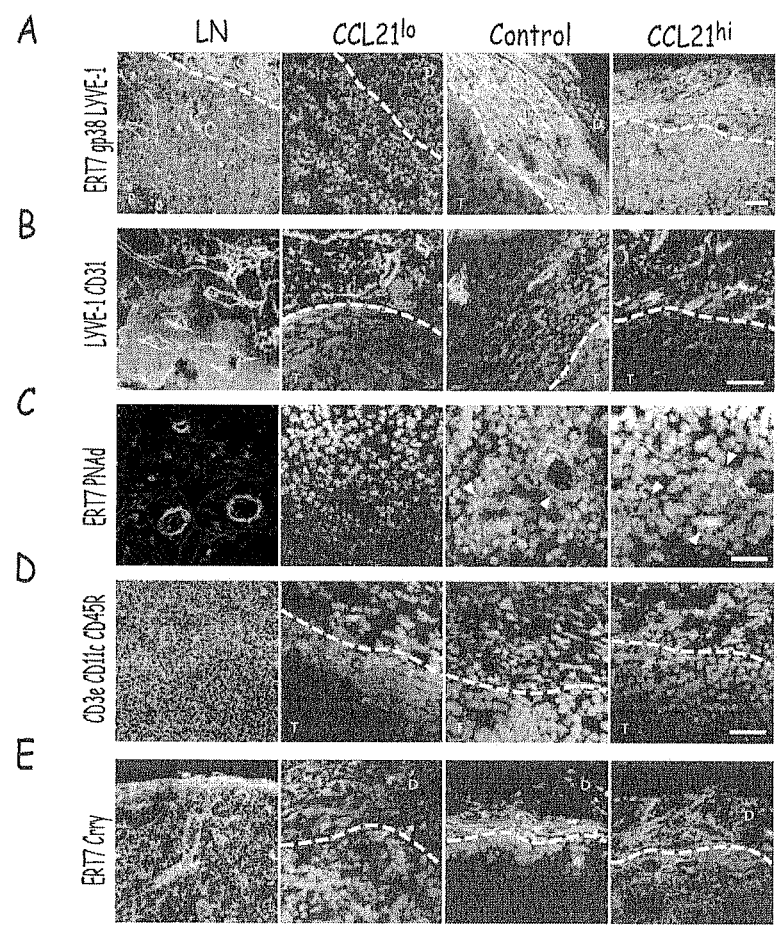
FIG. 7: Stroma of CCL21-expressing tumors share features of the lymph node T cell zone. (A) In CCL21-secreting (control and CCL21$^{hi}$) tumors, but not CCL21$^{lo}$ tumors, fibroblasts expressed markers of the reticular fibroblastic cells (gp38$^+$ERTR7$^+$LYVE-1$^-$) that are normally found in the paracortical sector of the LN. (B) Blood (CD31$^+$LYVE-1$^-$) and lymphatic (LYVE-1$^+$) vessels were found in all tumors. (C) Intratumoral vessels expressed PNAd (arrowheads) within control and CCL21$^{hi}$ but not CCL21$^{lo}$ tumors. (D) Immune cell infiltrates were located primarily at the tumor periphery. Unlike in the lymph node, no B cell zones were observed in any tumors. (E) Complement regulating protein Crry colocalized with ER-TR7 within the lymph node and in the borders of control and CCL21$^{hi}$ tumors. (F) Representative flow cytometry plots illustrating Crry expression within the CD45$^-$ stromal cell compartment of the tumor. (G) Representative flow cytometry plots illustrating CD3e$^-$CD4+ RORγt-GFP$^+$ lymphoid tissue inducer (LTi) cells in lymph nodes and tumors from Rorc(γt)-GFP$^{TG}$ mice; more were found in CCL21-secreting control tumors than in CCL21$^{lo}$ tumors implanted into Rorc(γt)-GFP$^{TG}$ mice. (H) In wildtype mice, control and CCL21$^{hi}$ contained significantly higher numbers of CD3e$^-$CD4$^+$RORγt$^+$ LTi cells than CCL21$^{lo}$ and control tumors treated with anti-CCR7 neutralizing antibody. (I) Representative flow cytometry plots showing the dominance of the non-stromal (gp38$^-$) fraction of CD3e$^-$CD4$^+$RORγt$^+$ cells within a tumor. (J) RORγt$^{hi}$ cells were largely negative for gp38 in the lymph node and in CCL21$^{hi}$ tumors, indicating their non-stromal association. Data in (A)-(F) were taken at day 21; others at day 9. LN: lymph node, D: dermis; T: tumor; C: capsule. Scale bars, in A, B and E, 200 μm; in C and D, 50 μm.
Figure 8:
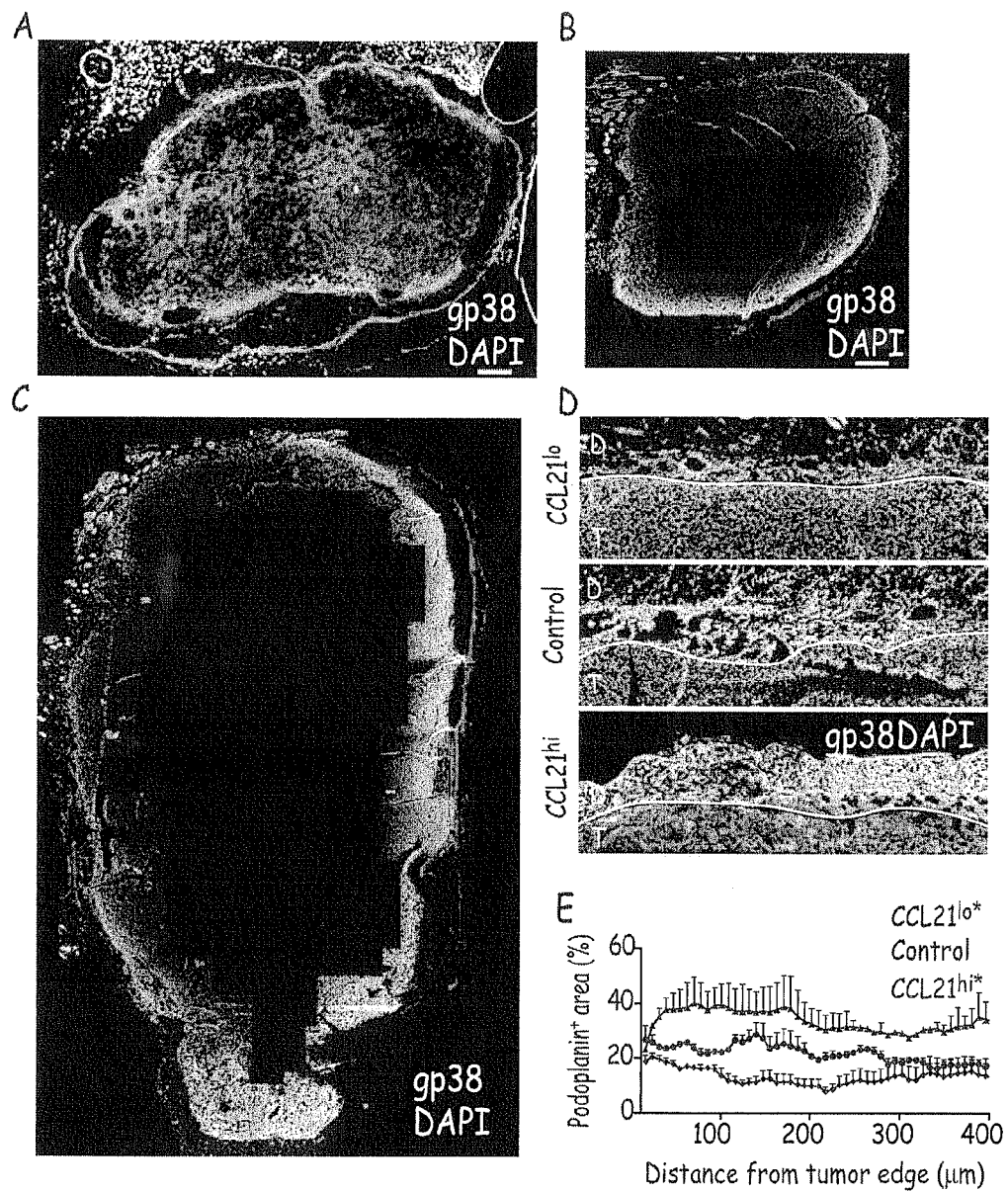
FIG. 8: Lymph node-like stromal networks surround CCL21-secreting tumors. Composite images showing gp38$^+$ (red) stromal structures within and around (A) lymph nodes, (B) CCL21-secreting control tumors, and (C) CCL21$^{lo}$ tumors; nuclei counterstained with DAPI, blue. (D) gp38$^+$ stromal cells (green), indicative of fibroblastic reticular cell networks, surrounds the control and CCL21$^{hi}$ tumors extensively but not the CCL21$^{lo}$ tumors; dotted line denotes the tumor edge (D: dermis, T: tumor). (E) Quantification of gp38 distribution as a function of distance from the tumor edge; **$P<0.01$. Bars, 500 μm.

CCL21-secreting tumors were examined to determine if similar features were present. It was recalled that CCL21 secretion by FRCs and high endothelial venules (HEVs) in the lymph node paracortex orchestrates T cell homing and education and subsequent immunological fate (Luther et al.). Previously, fibroblasts in the tumor vicinity (Peduto et al.) have been associated with poor prognosis (Kawase et al). FRC (gp38$^+$ER-TR7$^+$) networks were observed at the tumor edge of control and CCL21$^{hi}$ tumors that were reminiscent of those in the LN T cell zones (FIG. 7 Panel A and FIG. 8). Furthermore, although blood vessel density appeared similar in all tumors (FIG. 7 Panel B), the vessels in control and CCL21$^{hi}$ tumors were surrounded by ER-TR7$^+$ structures that also expressed peripheral node addressin (PNAd), which is normally associated with HEVs (FIG. 7 Panel C). Furthermore, T cells and dendritic cells could be seen throughout the tumor but were primarily located at the tumor-dermis interface (FIG. 7 Panel D). No significant B cell infiltrates were detected (FIG. 7 Panel D), and expression of the B-cell chemoattractant CXCL13 was low in all tumors (FIG. 6). The ER-TR7$^+$ stromal matrix, CCL21 secretion, and intratumoral vessel PNAd expression was reminiscent of the LN T cell zone.

Complement receptor 1-related gene/protein y (Crry) was also examined. Crry is a membrane-bound, complement-regulating protein that is critical for maintaining self-tolerance by causing the decay of C3 convertases to inactivate complement and through recruitment and activation of Tregs (Xu et al., Kemper et al.). High levels of Crry were observed on non-hematopoietic (CD45$^-$) cells in the margins of control and CCL21$^{hi}$ tumors but not in CCL21$^{lo}$ tumors (FIG. 7 Panels E-F), consistent with another study showing that Crry downregulation in aggressive tumors cells caused complement-mediated cell lysis and tumor regression (Varela et al.).

To understand how these lymphoid features arose, the process of lymphoid tissue ontogeny was used as a potential source of insight; this process is driven by recruitment of circulating precursor CD3e$^-$RORγ(t)$^+$ lymphoid tissue inducer (LTi) cells (Eberl et al, Randall et al.). These cells are also CCR7$^+$ and thus should be preferentially recruited to control and CCL21$^{hi}$ tumors as compared to CCL21$^{lo}$ tumors. Using Rorc(γt)-GFP$^{TG}$ mice, which generate GFP-expressing LTi cells (Eberl et al.), it was possible to detect more CD45$^+$CD3e$^-$CD4$^+$IL-7Ra$^+$RORγt-GFP$^+$ cells within lymph nodes and control tumors than in CCL21$^{lo}$ tumors (FIG. 7 Panel G), demonstrating preferential LTi cell accumulation in CCL21-secreting tumors. These patterns of LTi infiltration were repeated in C57/B16 mice and could be significantly attenuated when CCR7 blocking antibodies were administered (FIG. 7 Panel G). It was noted that the CD3e$^-$RORγt-high population in the tumors were largely gp38$^-$ (FIG. 7 Panels I-J), indicating that they were not associated with stromal cells.

Taken together, the data presented indicated that CCL21 secretion by tumors caused recruitment of LTi cells and development of lymphoid features, which in turn promoted interactions between T cells and APCs within the immunosuppressive cytokine environment of the tumor. This in turn would lead to a shift towards Tregs, promoting immune tolerance and providing an advantage for survival and invasion.

CCL21-Mediated Immune Tolerance is Systemic and General

Figure 9:
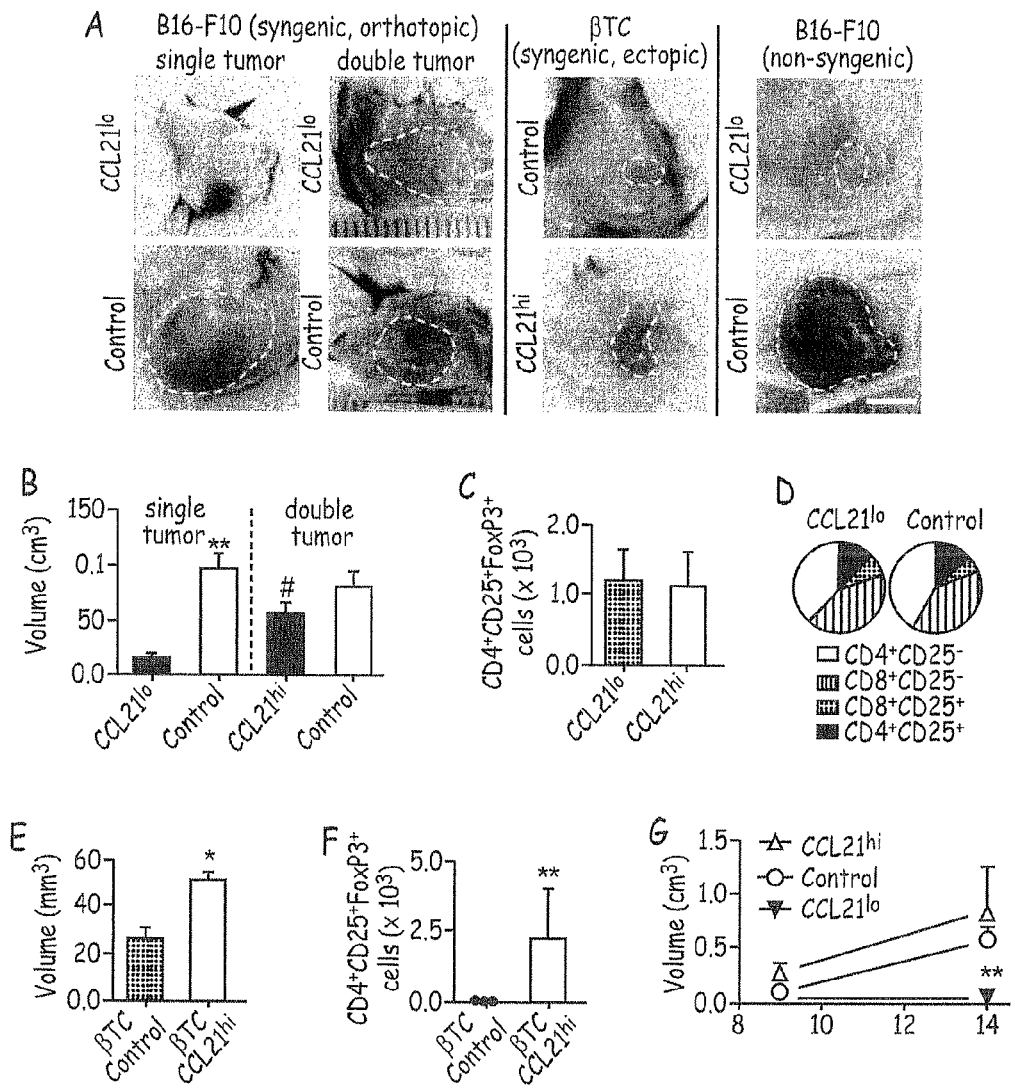
FIG. 9: CCL21-mediated immune tolerance is systemic and general. (A) Representative day 9 tumors from three alternative models. (B) CCL21$^{lo}$ tumor size significantly increases when implanted into control tumor-bearing C57BL/6 mice ('double tumor'), compared to when implanted alone ('single tumor'). (C) CD25$^+$FoxP3$^+$ Treg populations and (D) T cell population distributions are similar in CCL21$^{lo}$ and CCL21 $^{hi}$ or control tumors when grown together in the same mouse, in contrast to those in single tumors (FIG. 2D). (E,F) β tumor cells (βTCs) transfected to overexpress CCL21 (βTC-CCL21$^{hi}$) (E) grow significantly larger over 14 days in C57BL/6 than control-transfected β tumors, and (F) contain high numbers of Tregs, whereas no Tregs can be found in control β tumors. (G) Growth of CCL21$^{lo}$, control and CCL21$^{hi}$ B16-F10 tumors allografted into immune-competent, non-syngenic BALB/c mice. #$P<0.05$ compared with CCL21$^{lo}$ from single tumors; *$P<0.05$, **$P<0.01$ compared with relevant control. Bar, 5 mm.

It was not known whether the host tolerogenic response to CCL21-secreting tumors was local or systemic, and also whether this phenomenon was limited to B16-F10 melanoma in syngenic animals. It was discovered that CCL21-expressing tumors could rescue CCL21$^{lo}$ tumors when implanted on the opposite side of the same mouse. CCL21$^{lo}$ tumors, which are normally small, formed well-established lesions of a similar size to control tumors while the control tumors grew similarly to single-site tumors (FIG. 9 Panels A,B). These tumors, when grown in the same mouse, contained similar numbers of Tregs (FIG. 9 Panel C) and almost identical T cell type distributions (FIG. 9 Panel D). This indicated that the host tolerogenic response to the control and CCL21$^{hi}$ tumors was systemic.

To explore the tolerogenic influence of CCL21 overexpression another cell line, islet beta tumor cells (βTCs, background of C57BL/6) (Joyce et al.) transduced to overexpress CCL21 and grew significantly larger than control-transduced counterparts in C57BL/6 mice (FIG. 9 Panels A, E). These CCL21$^{hi}$ βTC tumors contained high numbers of Tregs while control-transfected counterparts contained virtually none (FIG. 9 Panel F), showing the same tolerogenic responses as observed with the B16-F10 melanomas.

As a more profound challenge, the CCL21 effect was tested in nonsyngenic hosts, using the three B16-F10 tumor cell lines implanted into BALB/c mice. Again, it was found that control and CCL21$^{hi}$ tumors grew robustly, while CCL21$^{lo}$ tumors completely failed to grow (FIG. 9 Panels A,G). Like the control and CCL21$^{hi}$ tumors in C57BL/6 mice, enhanced leukocyte attraction was observed, combined with a reduced T cell compartment and large numbers of Tregs in the CCL21-expressing tumors grown in BALB/c mice (data not shown).

Since CCL21-secreting tumors could rescue CCL21$^{lo}$ tumors grown on the opposite side of the same mouse as well as support the growth of alternative (orthotopic B16-F10, ectopic βTCs, and even non-syngenic B16-F10 allograft) tumor models, it was concluded that the CCL21-induced immune regulation is systemic and general.

Lymph Node Mimicry

These results provided new insights into the role of CCR7 ligand signaling. Tumors, and tolerization, were observed to progress through a mechanism of "lymph node mimicry". It was demonstrated that CCL21-secreting tumors recruit myeloid suppressor cells and LTi cells and become structurally similar to the lymph node paracortex; they also become rich in regulatory cytokines and Tregs, and they lacked antigen-specific CD8$^+$ T cells. With these changes, the host immune response shifted from immunogenic, as seen in CCL21$^{lo}$ tumors, to tolerogenic, as seen in control and CCL21$^{hi}$ tumors.

While naïve T cells are normally excluded from nonlymphoid tissues, CCL21 is sufficient for recruiting naïve T cells to peripheral sites (Weninger et al.) and can drive lymphoid tissue neogenesis. For example, transgenic mice overexpressing CCL21 in the thyroid showed significant lymphocytic infiltrates that were segregated into B and T cell areas, including PNAd$^+$ HEV-like vessels (Joyce et al.). This has typically been studied in the context of autoimmunity. However, CCL21 is not required for normal cytotoxic T cell responses, but is necessary for the maintenance of tolerance to self-antigens. For example, mice lacking CCL21 (plt/plt) demonstrate normal B and T cell immunity (Mori et al.) and slightly delayed but enhanced antigen-specific CD8$^+$ T cell responses (Junt et al), while mice lacking CCR7 develop generalized multi-organ autoimmunity (Davalos-Misslitz et al, Schneider, et al.). This suggests a critical role of CCL21 in mediating tolerance to self-antigens but not in antigen-specific immunity (Förster and Davalos-Misslitz). One difference in the tumor-induced lymph node mimicry observed here and the lymphoid structures associated with autoimmune diseases was the lack of B cell centers, normally driven by CXCL13. In the control and CCL21$^{hi}$ tumors, there was no evidence of CXCL13 induction (FIG. 6), and very few B cells within the tumor (FIG. 7 Panel C).

In addition, CCL21 can also influence naïve T cells, which express CCR7 and are thus recruited to CCL21$^+$ tumors. In the study described herein, control and CCL21$^{hi}$ tumors significantly displayed a larger leukocyte infiltrate than CCL21$^{lo}$ tumors, but while the CCL21$^{lo}$ tumors contained a larger T cell fraction, the control and CCL21$^{hi}$ tumors contained more Tregs. This is supported by several studies showing that CCR7 ligands promote Tregs—for example, by inducing T cell senescence through interference of IL-2 secretion (Ziegler et al), by promoting activation-induced cell death of antigen-responding T cells (Yasuda et al), and by activating the function of CD4$^+$CD25$^+$ Tregs (Schneider, et al.). Therefore, while CCL21-secreting tumors would attract more CCR7$^+$ naïve and regulatory T cells, they also further inhibit effector T cells while promoting Tregs.

This shift in the T cell population distribution, in turn, would shift the overall cytokine environment to be less immunogenic. This was evidenced by much higher levels of total TGF-$\beta_1$ (FIG. 7 Panel F) and indoleamine 2,3-dioxygenase (IDO, data not shown), which interferes with T cell expansion (Katz, et al.) and promotes Treg development (Chen, et al.). Furthermore, the high TGF-$\beta_1$ seen in CCL21-expressing tumors inhibits classically activated pro-inflammatory (M1) macrophages while recruiting and inducing macrophage transition to the alternatively activated pro-tumor (M2) phenotype, which are poorly cytotoxic, angiogenic, and immune-suppressive and which help drive tumor progression (Sica et al, Mantovani, et al.). TGF-$\beta_1$ also causes Treg induction and conversion through a $T_H3$ response to promote tolerance (Moo-Young et al, Biollaz et al.) and can induce Treg differentiation from proliferating memory T cells in the periphery (Akbar, et al.). In contrast, high IFN-$\gamma$ found in CCL21$^{lo}$ tumors supports M1 macrophage polarization and $T_H1$ mediated anti-tumor responses (Shankaran et al) while inhibiting Foxp3$^+$ Treg function (Fragale et al). Therefore, the functional differences seen in the Treg vs. Trp2$^+$-specific effector T cell compartments between tumor types (FIG. 7 Panels B-E) are evidence of this immunomodulatory shift.

The immunomodulatory effects of CCR7 ligands on tumors are controversial in the scientific literature. Previous reports, for instance, have described enhanced anti-tumor immune responses after CCL21 addition or transfection (Ashour et al., Nomura, et al., Turnquist et al., Wu et al.) presumably due to increased DC and T cell attraction to the tumor that would then lead to increased immunogenicity. And CCL19 has been reported to elicit an anti-tumor response (Gao et al., 2005). Conversely, ectopic CCL19 administration or overexpression was shown to prevent tumor allograft rejection (Ziegler et al. 2006, Krautwald et al.), possibly by inhibiting T cell proliferation (Ziegler et al 2007) and/or entrapment of the DCs inside the tumor, preventing them from migrating out and mounting an immune response (Ziegler et al 2006.). However, it was recently shown that fluid flow created by lymphatic drainage can generate CCL21 gradients in the direction of flow (Shields et al.), even at high tumor CCL21 concentrations (data not shown). To rule out the mechanism of DC entrapment, it was demonstrated that fluorescent microsphere-loaded DCs could traffic to draining lymph nodes from both CCL21-expressing tumors as well as from CCL21$^{lo}$ tumors (FIG. 4), suggesting that there was no impairment in DC trafficking from CCL21-expressing tumors. Instead, the finding herein of LTi cells and structural similarities with lymph nodes in CCL21-expressing tumors helps to explain how those tumors could shift the T cell repertoire towards a tolerogenic phenotype. FRCs found in CCL21-expressing tumors could equip the tumor with a substrate, structurally similar to those in the LN T cell zone, to further guide naïve T cell interactions with DCs, homing of Tregs (Forster et al., 1999), and Treg induction (Ochando et al.), all under a regulatory cytokine milieu.

Figure 10:
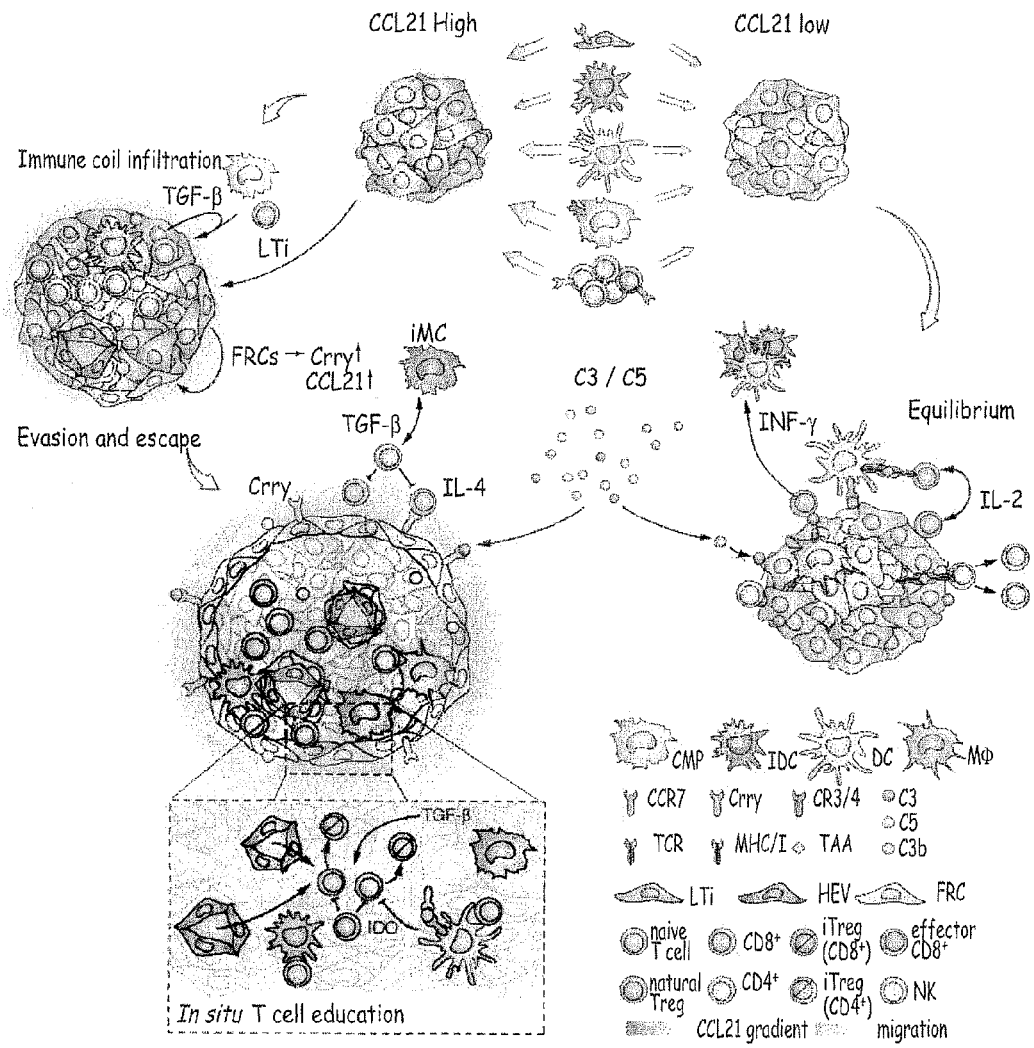
FIG. 10: Hypothesized mechanism of how tumors use CCL21 for immune regulation. In the early phase of tumor development, CCL21-secreting tumors attract more CCR7$^+$ cells (naïve T cells, iTregs and APCs) and recruit lymphoid tissue inducer (LTi) cells that invoke the formation of lymph node-like structures such as high endothelial cell-like PNAd$^+$ vessels and gp38$^+$ reticular stromal cells that form a stromal network. This network in the tumor periphery supports its development in several ways. For example, stromal Crry helps modulate and protect the tumor from complement-mediated attack through inactivation of C3. Furthermore, gp38$^+$ reticular stromal cells also secrete CCL21, which together with the structural architecture and cytokine milieu encourages naïve T cells and DCs to co-localize, promoting a regulatory T cell phenotype (inset). Increased recruitment of immature myeloid cells (iMCs), likely through C5a, may inhibit T cell effector function, while higher TGF-$\beta_1$ can interfere with DC and T cell interactions and stimulate even more Tregs. Without this cascade of events (stroma formation, complement regulation and Treg induction within a protumor milieu), CCL21$^{lo}$ tumors evoke an anti-tumor immune response, where recruited iMCs may differentiate into effective antigen-presenting cells that, in combination with IL-2 (which is not attenuated in the absence of CCR7 ligands), are permissive for effector T cell proliferation. iDC: immature dendritic cell; CMP: common myeloid precursor; iMC: immature myeloid cell; MΦ: macrophage; TGF-$\beta_1$: Transforming growth factor beta; IDO: indoleamine 2,3-dioxygenase; IFN-γ: interferon gamma; IL-2: Interleukin-2; IL-4: Interleukin-4; Clay: Complement receptor 1—related gene/protein y. Rodent membrane-bound inhibitor of complement activation; CR3/4: complement receptor 3 and 4; TCR: T cell receptor; MHC/I: major histocompatibility complex molecule Class I; TAA: tumor associated antigen; C3: complement component 3; C3b: fragment of C3; C5: complement component 5; LTi: lymphoid tissue inducer cell; HEV: high endothelial venule; FRC: fibroblastic reticular cell; Treg: regulatory T cell; iTreg: inducible regulatory T cell; NK: natural killer cell.

Finally, the data point to a theory, which is not be taken as limiting the scope of the invention, that the complement cascade in the CCL21-mediated tolerance was involved; this cascade has previously been shown to play a role in tumor-induced tolerance (Markiewski et al.). The complement regulating receptor Crry was only found in CCL21-secreting tumors, and complement inactivation through Crry-dependent inactivation can protect tumor cells from deposition of active complement components and subsequent cell lysis (Varela et al.) while initiating M2 macrophages and prompting IL-4 production from recruited T cells (Fernandez-Centeno, et al.). Second, inhibitory complement fragments can bind DCs to down-regulate co-stimulatory molecules and prevent DC maturation, leading to the inability to activate cytotoxic T cells (Verbovetski et al.). To summarize, a hypothesized mechanism for CCL21-enhanced tumor tolerance is illustrated in FIG. 10. These findings of lymph node mimicry as a mechanism for immune regulation by tumors hold therapeutic significance to tumor vaccine strategies (William, Jr., et al.) and to emerging anti-tumor immunotherapies utilizing chemokines (including CCL21 and CCL19) (Ziegler et al 2006, Ashour et al, Nomura et al., Turnquist, Wu et al, Krautwald et al.) to functionally bias the recruited immune cell infiltrates within the tumor.

EXAMPLES

The following examples provide detail with respect to results already described above and present further new information.

Example 1

Materials and Methods

A. Tumor Cell Lines

B16-F10 melanoma cells (ATCC) derived from C57BL/6 mice were maintained in DMEM supplemented with 10% FBS and penicillin-streptomycin-amphotericin B. shRNA knockdown melanoma cells were created using lentiviral transduction of shRNA for CCL21, or scrambled shRNA (Mission shRNA, Sigma-Aldrich). Briefly, lentivectors carrying the shRNA for mCCL21, scrambled shRNA or mCCL21ser cDNA (Mission shRNA, Sigma-Aldrich) were sub-cloned from pORF-mExodus2 v2.1 (hwivogen) into the PRRLSIN.CPPT.PGK.WPRE lentivector and were then transfected into 293T cells together with the pCMVR8.74 packaging plasmid and pMD2.G envelope plasmid in a ratio of 3:2:1. Medium was collected after 48 hours and the virus was concentrated by ultracentrifugation. B16-F10 cells were transduced with either the lentivirus carrying CCL21 shRNA (CCL21$^{lo}$) or scrambled shRNA (control), or mCCL21ser cDNA (CCL21$^{hi}$) at a multiplicity of infection of 10$^4$. Stably shRNA-transduced cells were selected by antibiotic resistance to puromycin. Clones were generated by serial dilutions and expanded; clones were chosen following ELISA and PCR for CCL21. Human MDA-MB-435 and Beta tumor cells ($\beta$TC) were transduced in the same way to overexpress CCL21.

B. Animals 6-8 week old female C57BL/6 mice (Charles River) were used for syngenic allograft models. CCR7−/− mice on a C57CL/6 background (Britschgi et al.), and the C57BL/6 Rorc(γt)-GFPTG (Eberl et al.). For all in vivo experiments, 500,000 tumor cells were suspended in 50 μl sterile saline and inoculated subcutaneously dorso-ventrally in the anesthetized mouse. All procedures were carried out in accordance with Swiss law. For blocking studies, mice received either neutralizing anti-CCR7 (25 μg per mouse per treatment) or matched IgG control (both from eBioscience) I.P. every 2 days.

C. Cell Isolation

Mice were anesthetized and sacrificed by cervical dislocation. Tumors, LNs (brachial, axillary, and inguinal), and (except for spleens) incubated in collagenase D (1 mg/ml in HBSS with 2% FBS) for 3 h (tumors) or 30 min (lymph nodes) at 37° C. The reaction was quenched with 100 mM EDTA; cell suspensions were passed through a 70 μm cell strainer and washed with HBSS. Splenocytes were isolated via mechanical disruption of spleens.

D. Peritoneal Macrophage Isolation

Murine macrophages were isolated by injecting Brewers Thioglycollate medium intraperitoneally into C57BL/6 mice. After 4 days mice were sacrificed and the peritoneal cavity wall was exposed. 10 ml sterile saline was injected into the peritoneal cavity and mixed, and the macrophage-rich fluid was withdrawn. Cell suspensions were passed through 40 μm cell strainers and characterized phenotypically by FACS analysis before being assayed in vitro.

E. Antibodies and Flow Cytometry

The following anti-mouse antibodies were used for flow cytometry: CD45-APC or CD45-Pac blue, or biotinylated CD45, CD3e-pacific blue or CD3e-PerCPCy5.5, CD4-PECy7 or CD4-PE, CD8α-APC-Cy7, B220-PECy5, F4/80-PE, CD25-FITC, FoxP3-PerCPCy5.5, CD11c-APC, MHCII-FITC, biotinylated GR1, biotinylated Crry, GP38 FITC, IL-7Rα-APC, ROR-γt-PE, and CD11b-PECy7 (all from eBioscience). Tetramer staining for Trp2 H-2kb-PE (ProImmune) was performed according to manufacturers guidelines. Antibodies were prepared in 24G2 hybridoma medium and HBSS/0.2% BSA and added to samples prior to incubation at 4° C. for 30 min in the dark. Samples were washed and those requiring secondary antibody were incubated for an additional 15 min with Streptavidin-conjugated pacific orange. Propidium iodide was used to sort out dead cells. Analysis was performed on a CyAn ADP Flow Cytometer (DAKO).

F. Dendritic Cell Trafficking In Vivo

B16-F10 CCL21$^{lo}$, control or CCL21$^{hi}$ tumor cells were implanted as described. After 4 days, tumors were inoculated with 20 μl of 0.5 μm FITC-conjugated latex microspheres (Polysciences, diluted 1:25 in sterile saline). 24 h later, tumors and lymph nodes (axillary and brachial) were harvested and single cell suspensions were generated as described above. Cells were stained and analyzed by flow cytometry.

G. ELISA

Tumor samples, snap frozen at the time of extraction, were homogenized in the presence of lysis buffer of Tissue Protein Extraction Reagent (TPER, Pierce) and a protease inhibitor cocktail. Tumor homogenates were then assessed for CCL21, TFG-β1, and IFN-γ using ELISA kits (R&D Systems) according to manufacturer's instructions.

H. Immunofluorescence

Frozen samples of tumors, lymph nodes, and normal skin were cryosectioned (10 μm) and subjected to standard immunofluorescence protocols using the following anti-mouse antibodies: FITC-conjugated rat anti-CD31 (1:100, BD Pharmingen), rabbit anti-LYVE-1 (1:500, RELIATech), goat anti-gp38 (1:75, R&D Systems), rat anti-ER-TR7 (1:50, Hycult Biotech), rat anti-Crry (1:100, BD Pharmingen), rat anti-PNAd (1:100, Biolegend), hamster anti-CD3e (1:100 BD Pharmingen), rat anti-CD45r (1:100, BD Pharmingen) and APC conjugated CD11c (1:40, Ebioscience); fluorescently conjugated secondary antibodies were from Invitrogen, and samples were counterstained with DAPI (Vector Laboratories).

I. Cytokine Arrays

Tumor samples, snap frozen at the time of extraction, were homogenized in the presence of lysis buffer supplemented with a protease inhibitor cocktail and passed through a syringe to aid lysis. Tumor homogenates were run on a cytokine array according to manufacturers guidelines (R&D Systems).

J. In Vitro Characterization

Proliferation and spheroid-forming potential of tumor cell sub-lines were assessed in vitro. Cells were seeded within 3D MATRIGEL matrices (BD Biosciences) in DMEM with 10% FBS, and proliferation was measured by digesting the gel using BD Cell Recovery Solution (BD Biosciences) at various time points and counting the cells. For spheroid formation studies, cultures were maintained in 3D matrices for 6 days. In some experiments, CCL21$^{lo}$ cells were supplemented with 500 ng/ml rmCCL21 and control cells were treated with neutralizing antibodies against CCR7 (20 μg/ml, Ebioscience clone 4B12). Gels were imaged and average spheroid volume was calculated.

K. In Vitro Migration

A modified Boyden chamber assay was used to assess functionality of CCR7 and responsiveness to CCL21 using 10 mm diameter, 8 μm pore transwell inserts (Millipore). 100 μl 1.8 mg/ml collagen (BD Biosciences) containing $10^6$ tumor cells/ml were seeded, and after polymerization, 500 ng/ml rmCCL21 (R&D Systems) was added to the lower chamber. In some chambers, neutralizing antibodies against CCR7 (clone 4B12, R&D Systems) were added at 10 μg/ml to both the medium chambers as well as in the gel compartment. Chambers were incubated for 24 h, after which gels containing non-migrated cells were removed; chambers were fixed and membranes stained with DAPI. Migration was determined by counting 6 random fields of view.

To determine the responsiveness of immune cells to the different tumor cell sublines, tumor cells were seeded in 24-well plates, allowed to adhere overnight, and the medium switched to basal medium. Peritoneal macrophages or splenocytes were seeded into 24-well transwell inserts, which were then incubated in the tumor cell-containing wells for 24 h. Transmigrated cells were stained for appropriate markers and evaluated by flow cytometry.

L. Statistics

Unless otherwise noted, data in bar graph form are presented as mean±s.e.m, while data shown as individual points include the median. Statistical significance was defined as $p<0.05$ following one-way ANOVA and Bonferroni post-hoc analysis. Box plots are presented as Tukey box plots.

Example 2

Cloning of Murine CCL21 Serine in Lentiviral Vectors and Lentivirus Production

CCL21ser was used for experimentation in mice. In order to make the PGK-CCL21ser lentivector, cDNA of murine CCL21ser from pORF5-mExodus2 v.21 (Invivogen, San Diego, Calif.) was subcloned into the pRRLSIN.cPPT.PGKGFP.WPRE lentivector in place of green fluorescent protein (GFP). Briefly, pORF5-mExodus2 v.21 was digested with ECORV (BioLabs, Ipswich, Mass.) for 2 hours at 37° C. The DNA was then purified from the buffer and then digested with NheI (BioLabs) for 2 hours at 37° C., blunt ended by treatment with DNA polymerase I (BioLabs) at 37° C. for 1 hour, and dephosphorylated with ANTARCTIC PHOSPHATASE (BioLabs) for 1 hour at 37° C. The cDNA fragment of the plasmid encoding mCCL21ser was recovered by gel electrophoresis and purified with a gel extraction kit (Qiagen). The lentivector plasmid pRRLSIN.cPPT.PGKGFP.WPRE was digested with SAL I (BioLabs) for 2 hours at 37° C. The DNA was then purified from the buffer and then digested with AgeI (BioLabs) for 2 hours at 37° C., and then blunt ended by treatment with DNA polymerase I (BioLabs) at 37° C. for 1 hour. The vector fragment of the plasmid was separated from the GFP gene by gel electrophoresis, and purified with a gel extraction kit (Qiagen). cDNA of mCCL21ser and lentivector (without the GFP cDNA) were ligated with the quick ligation kit (BioLabs) for 10 minutes at room temperature. Ligated vector plasmid containing the mCCL21ser cDNA driven by the PGK promoter was expanded in competent $E.\ coli$ and plasmid DNA from antibiotic-resistant colonies was purified and analyzed for the correct recombination event by digestion with different restriction enzymes targeting the mCCL21ser cDNA insert and gel electrophoresis.

Control lentivectors for the CCL21 vectors were the original pRRLSIN.cPPT.PGKGFP.WPRE lentivector: GFP control, and the pRRLSIN.cPPT.PGK.WPRE lentivector without the GFP insert: CONTROL.

Lentiviral vectors were produced via transfection of HEK293T cells with the CCL21ser lentivector (21+) or pRRLSIN.cPPT.PGKGFP.WPRE lentivector (GFP control), or the pRRLSIN.cPPT.PGK.WPRE lentivector (CONTROL) transfer plasmid, and the pCMVR8.74 packaging plasmid, and pMD2.G envelope plasmid in the ratio 3:2:1. Media was changed after 12 hours and supernatants containing the virus were collected after 24 and 36 hours and virus concentrated by ultracentrifugation at 19 k g for 2 h at 16° C.

Example 3

Construction of an Invasive Tumor Cell Line, B16F10 Melanoma Cells, Overexpressing CCL21

B16F10 (CRL6475, ATCC, Manassas, Va.) cells are an invasive mouse melanoma cell line derived from C57B1/6 mice. F10 cells were routinely cultured in 5% $CO_2$ at 37° C. in Dulbecco's modified Eagle's medium (DMEM; Gibco Invitrogen, Grand Island, N.Y.) supplemented with 10% (v/v) heat-inactivated fetal bovine serum (FBS; Gibco Invitrogen), and a 1% (v/v) lyophilized mixture of penicillin and streptomycin (Gibco Invitrogen). Subpassage was performed every fifth day and the medium was changed every second day during subculture.

In order to generate F10 cells stably overexpressing CCL21 (F10 21+), 10000 cells were transduced with 50 µl of the concentrated lentivirus containing the mCCL21ser insert. Controls for these cells were generated by transducing 10000 cells either with 50 µl of the GFP vector (pRRLSIN.cPPT.PGKGFP.WPRE, F10 GFP) or 50 µl of the empty vector (pRRLSIN.cPPT.PGK.WPRE, F10 control). The levels of over-expression of CCL21 were determined by ELISA assay (DUOSET, R&D Systems, Minneapolis, Minn.) of the supernatant of F10 21+ (3.470 pg CCL21/1000 cells/24 h), F10 GFP (0 pg CCL21/1000 cells/24 h), and F10 control (0.003 pg CCL21/1000 cells/24 h) in culture. Lentivector integration in the cell genomic DNA was quantified by TAQMAN qRT-PCR for Gag and WPRE viral gene targets with Titine as a house keeping gene, which correlates with the number of copies of either mCCL21ser or GFP integrated in the genome of the F10 21+(0.57 copies), and F10 GFP (12.99 copies) respectively. Primers sequences were the following:

| | Primer Sequences | | | |
|---|---|---|---|---|
| Gag | Gag_Forward | GGAGCTAGAACGATT CGCAGTTA | SEQ ID NO: 1 | FAM-BHQ |
| | Gag_Reverse | GGTGTAGCTGTCCCA GTATTTGTC | SEQ ID NO: 2 | |
| | Gag_probe | ACAGCCTTCTGATGT TTCTAACAGGCCAGG | SEQ ID NO: 3 | |
| WPRE | WPRE_forward | GGCACTGACAATTCC GTGGT | SEQ ID NO: 4 | FAM-BHQ |
| | WPRE_reverse | AGGGACGTAGCAGAA GGACG | SEQ ID NO: 5 | |
| | WPRE_probe | ACGTCCTTTCCATGG CTGCTCGC | SEQ ID NO: 6 | |
| Titine | Titin_forward | AAAACGAGCAGTGAC GTGAGC | SEQ ID NO: 7 | FAM-BHQ |
| | Titin_reverse | TTCAGTCATGCTGCT AGCGC | SEQ ID NO: 8 | |
| | Titin_probe | TGCACGGAAGCGTCT CGTCTCAGTC | SEQ ID NO: 9 | |

Example 4

Construction of a Low-Invasive Tumor Cell Line, B16F1 Melanoma Cells, Expressing CCL21

B16F1 cells (CRL6323, ATCC, Manassas, Va.) are a moderately invasive mouse melanoma cell line derived from C57B1/6 mice. F1 cells were routinely cultured in 5% $CO_2$ at 37° C. in Dulbecco's modified Eagle's medium (DMEM; Gibco Invitrogen, Grand Island, N.Y.) supplemented with 10% (v/v) heat-inactivated fetal bovine serum (FBS; Gibco Invitrogen), and a 1% (v/v) lyophilized mixture of penicillin and streptomycin (Gibco Invitrogen). Subpassage was performed every fifth day and the medium was changed every second day during subculture.

In order to generate F1 cells stably overexpressing CCL21 and GFP (F1 21+ GFP), 10000 cells were transduced with 50 µl of the concentrated lentivirus containing the mCCL21ser insert and 50 µl of the GFP vector (pRRLSIN.cPPT.PGKGFP.WPRE). Controls for these cells were generated by transducing 10000 cells with 50 µl of the GFP vector (pRRLSIN.cPPT.PGKGFP.WPRE, F1 wt GFP). The levels of over-expression of CCL21 were determined by ELISA assay of the supernatant of F1 21+ GFP (52.30 µg CCL21/1000 cells/24 h), and F1 wt GFP (0 pg CCL21/1000 cells/24 h), cultured in 2D. Lentivector integration in the cell genomic DNA was quantified by TAQMAN qRT-PCR for Gag and WPRE viral gene targets with Titine as house keeping gene, which correlates with the number of copies of mCCL21ser and GFP, and the number of copies of GFP integrated in the genome of the F1 21+ GFP (26.95 copies), and F1 wt GFP (6.24 copies) respectively.

Example 5

Construction of a Cell Line, MDA Melanoma Cells, Expressing CCL21ser

MDA cells are a human melanoma cell line (HTB-129, ATCC, Manassas, Va.). MDA cells were routinely cultured in 5% $CO_2$ at 37° C. in Dulbecco's modified Eagle's medium (DMEM; Gibco Invitrogen, Grand Island, N.Y.) supplemented with 10% (v/v) heat-inactivated fetal bovine serum (FBS; Gibco Invitrogen), and a 1% (v/v) lyophilized mixture of penicillin and streptomycin (Gibco Invitrogen). Subpassage was performed every fifth day and the medium was changed every second day during subculture.

In order to generate MDA cells stably overexpressing CCL21 (MDA 21+), 10000 cells were transduced with 50 µl of the concentrated lentivirus containing the mCCL21ser insert. Controls for these cells were generated by transducing 10000 cells with 50 µl of the empty vector (pRRLSIN.cPPT.PGK.WPRE, MDA control). The levels of over-expression of CCL21 were determined by ELISA assay (DUOSET, R&D Systems, Minneapolis, Minn.), of the supernatant of MDA 21+(46.28 pg CCL21/1000 cells/24 h), and MDA control (0 pg CCL21/1000 cells/24 h), in cell culture.

Example 6

Construction of a Mouse Embryonic Stem Cell (mES) Cell Line, Expressing CCL21ser mES cells R1 (SCRC-1011, ATCC, Manassas, Va.) are a mES cell line derived from 129X1×129S1 mice. The mES cells were routinely cultured on a feeder layer of MEFs treated with 10 µg/ml mitomycin C (Sigma-Aldrich, St. Louis, Mo.) in 5% $CO_2$ at 37° C. in Dulbecco's modified Eagle's medium (DMEM; Gibco Invitrogen, Grand Island, N.Y.) supplemented with 15% (v/v) heat-inactivated fetal bovine serum (FBS; HyClone, Logan, Utah), 0.1 mM β-mercaptoethanol (Gibco Invitrogen), 1% (v/v) nonessential amino acids (NEAA; Gibco Invitrogen), 1 mM sodium pyruvate (Sigma-Aldrich), 2 mM L-glutamine (Gibco Invitrogen), a 1% (v/v) lyophilized mixture of penicillin and streptomycin (Gibco Invitrogen) and 1,000 units/ml mouse leukemia inhibitory factor (LIF) (Chemicon International, Temecula, Calif.) (ESC culture medium). Subpassage was performed every third day and the medium was changed daily during subculture.

In order to generate ES cells stably overexpressing CCL21 (ES 21₊), 10000 cells were transduced with 50 µl of the concentrated lentivirus containing the mCCL21ser insert. Controls for these cells were generated by transducing 10000 cells with 50 µl of the empty vector (pRRLSIN.cPPT.PGK.WPRE, ES control). The levels of over-expression of CCL21 were determined by ELISA assay (DUOSET, R&D Systems, Minneapolis, Minn.), of the supernatant of ES 21+(5.75 pg CCL21/1000 cells/24 h), and ES control (0.002 pg CCL21/1000 cells/24 h), cultured in 2D. Lentivector integration in the cell genomic DNA was quantified by TAQMAN qRT-PCR for Gag and WPRE viral gene targets with Titine as house keeping gene, which correlates with the number of copies of either mCCL21ser or empty insert integrated in the genome of the ES 21+(20.96 copies), and ES control (8.96 copies) respectively.

Example 7

Measurement of B16F10 Tumor Growth, With and Without CCL21 Expression, in Balb/c Mouse Recipients As an indication of tolerization, a non-syngeneic allograft of B16F10 (from C57B1/6 mice) into Balb/c recipient mice was performed. F10 wt GFP, F10 21+ and a mix of both F10 wt GFP and F10 21+ (1:1) were harvested from 2D cultures and resuspended in sterile saline solution. A total of 500,000 cells in 50 µl saline were injected subdermally in the back of Balb/c mice after removal of fur. Tumor volumes were measured daily and tumors were excised at 11 days after grafting.

Figure 11:
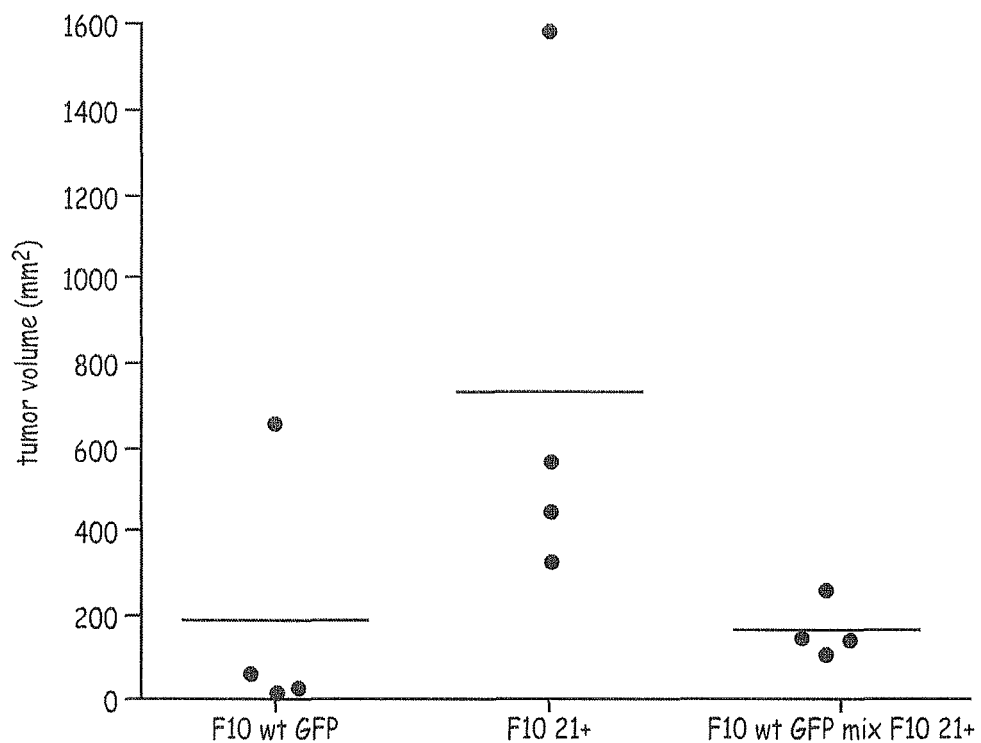
FIG. 11: B16F10 tumor cells expressing a control protein (F10wtGFP), over-expressing CCL21 (F10 21+), or the two cell types mixed together (F10wtGFP mix F10 21+), were implanted subcutaneously in mice in the non-syngeneic host Balb/c mouse. Tumor volume was determined after explantation at 11 days post-grafting. Rejection of the tumor ensued in the absence of CCL21 overexpression, whereas tolerization ensued in the presence of CCL21 overexpression.

Measurement of tumor size was performed with a digital caliber after tumor excision and tumor volume was calculated with the ellipsoid formula. Tumors overexpressing CCL21 (F10 21+) were significantly bigger (729 mm$^2$±576) than tumors expressing low levels of CCL21 (F10 wt GFP, 189 mm$^2$±311) and tumors generated by a mixed population of the two cell types (F10 wt GFP and F10 21+, 1:1, 164 mm$^2$±65) (FIG. 11). Thus, the B16F10 tumor cells in a non-syngeneic-host were protected from rejection by tolerization due to CCL21 expression.

After tumors were surgically removed together with the skin, they were sectioned in half (part 1 and 2) and processed for (1) immunohistochemistry on thin sections for structural phenotyping and immune cell localization and (2) flow cytometry for immune cell panels to probe immune repertoires within the tumor. For (1) the antibodies for the following targets have been used: ERTR7, gp38, CCL21, CD45, CD3e, F480, CD11c, B220, LYVE-1, CD31. For (2) the antibodies for the following targets have been used: CD45, CD3ε, IL7Rα, γδ-TCR, CD25, CD4, CD8α, FoxP3, panNK, Tet-Trp2, CD19, MHCII, F4/80, CCR7/CD40/CD86/CD11b/CD11c/RORγt, Gr1.

Flow cytometry results showed that the total number of activated CD4 T regulatory cells (CD25+FoxP3+), gamma-delta T cells, CD45+CCR7+ cells, mature and immature myeloid DCs (CD11b+CD11c+F480-MHCII+ and MHC- respectively), myeloid suppressor cells (CD11b+MHCII-GR1+), granulocytes (CD11b+MHCII-GR1int) and lymphoid immature DCs (CD11b-MHCII-CD11c+), were increased in tumors overexpressing CCL21 (F10 21+) compared to tumors expressing low levels of CCL21 (F10 wt GFP) (Table 1).

TABLE 1

|  | Total Number of Cells | | | |
|---|---|---|---|---|
|  | F10 wt GFP | | F10 21+ | |
|  | average | st dev | average | st dev |
| CD4+ CD25+ FoxP3+ | 78 | 33 | 193 | 163 |
| TCRγδ | 1678 | 1692 | 2704 | 1911 |
| CD45+ CCR7+ | 4744 | 3619 | 9714 | 5521 |
| CD11b+ CD11c+ MHCII+ F480− | 118 | 133 | 897 | 997 |
| CD11b+ CD11c+ MHCII− | 216 | 223 | 505 | 628 |
| CD11b+ MHCII− GR1+ | 2467 | 2217 | 5874 | 4769 |
| CD11b+ MHCII− GR1int | 8841 | 7555 | 29830 | 23119 |
| CD11b− MHCII− CD11c+ | 1844 | 1533 | 3246 | 1852 |

Example 8

Measurement of B16F1 Tumor Growth With and Without CCL21 Expression in Balb/c Mouse Recipients As an indication of tolerization, a non-syngeneic allograft of B16F1 (from C57B1/6 mice) into Balb/c recipient mice was performed. F1 wt GFP and F1 21+GFP were harvested from cell cultures and resuspended in sterile saline solution. A total of 500,000 cells in 50 μl saline were injected subdermally in the back of Balb/c mice after removal of fur. Tumors were measured daily and excised at 15 days after grafting.

Figure 12:
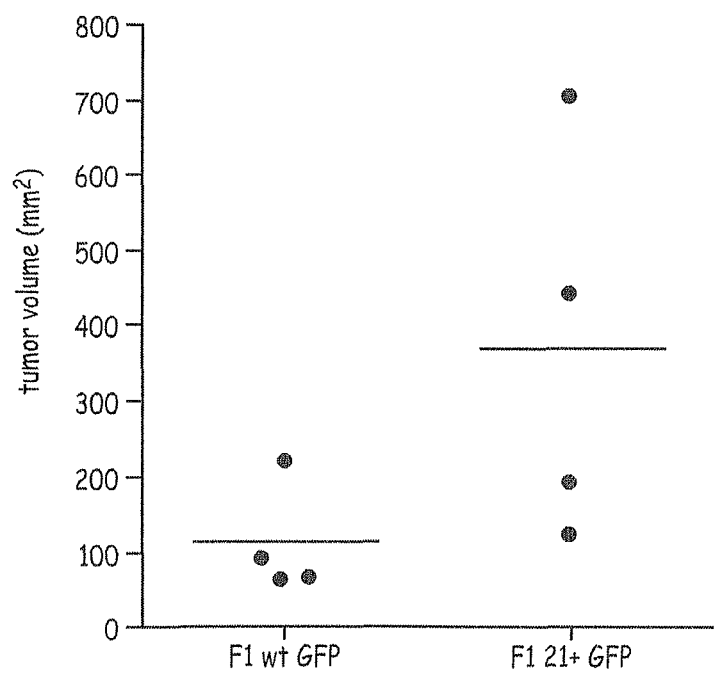
FIG. 12: B16F1 melanoma cells, either overexpressing CCL21 (F1 21+ GFP) or not (F1 wt GFP) were implanted subcutaneously in mice in the non-syngeneic host Balb/c mouse. Tumor volume was determined after explantation at 15 days post-grafting. Rejection of the tumor ensued in the absence of CCL21 overexpression, whereas tolerization ensued in the presence of CCL21 overexpression.

Measurement of tumor size was performed with a digital caliber after tumor excision and tumor volume was calculated with the ellipsoid formula. Tumors overexpressing CCL21 (F1 21+GFP) were significantly bigger (366 mm$^2$±265) than tumors expressing low levels of CCL21 (F1 wt GFP, 111 mm$^2$±76) (FIG. 12). Thus, the B16F1 tumor cells in a non-syngeneic-host were protected from rejection by tolerization due to CCL21 expression.

After tumors were surgically removed together with the skin, they were sectioned in half (part 1 and 2) and processed for (1) immunohistochemistry on thin sections for structural phenotyping and immune cell localization and (2) flow cytometry for immune cell panels to probe immune repertoires within the tumor. For (1) the antibodies for the following targets have been used: ERTR7, gp38, CCL21, CD45, CD3e, F480, CD11c, B220, LYVE-1, CD31. For (2) the antibodies for the following targets have been used: CD45, CD3ε, IL7Rα, γδ-TCR, CD25, CD4, CD8α, FoxP3, panNK, Tet-Trp2, CD19, MHCII, F4/80, CCR7/CD40/CD86/CD11b/CD11c/RORγt, Gr1.

Flow cytometry results showed that the total number of activated CD4 T regulatory cells (CD25+FoxP3+), gamma-delta T cells, CD45+CCR7+ cells, mature and immature myeloid DCs (CD11b+CD11c+F480-MHCII+ and MHC− respectively), myeloid suppressor cells (CD11b+MHCII-GR1+), granulocytes (CD11b+MHCII-GR1int) and lymphoid immature DCs (CD11b-MHCII-CD11c+), were increased in tumors overexpressing CCL21 (F1 21+GFP) compared to tumors expressing low levels of CCL21 (F1 wt GFP) (Table 2) while the percentage of CD45+CD8 T cells was decreased.

TABLE 2

|  | Total Number of Cells | | | |
|---|---|---|---|---|
|  | F1 wt GFP | | F1 21+ GFP | |
|  | average | st dev | average | st dev |
| CD4+ CD25+ FoxP3+ | 263 | 180 | 411 | 80 |
| TCRγδ | 2003 | 1206 | 3891 | 2354 |
| CD8+ % CD45+ | 6 | 1 | 2 | 2 |
| CD45+ CCR7+ | 20053 | 11119 | 89834 | 26777 |
| CD11b+ CD11c+ MHCII+ F480− | 307 | 239 | 1423 | 708 |
| CD11b+ CD11c+ MHCII− | 302 | 142 | 861 | 427 |
| CD11b+ MHCII− GR1+ | 1560 | 1205 | 3598 | 3512 |
| CD11b+ MHCII− GR1int | 6840 | 4069 | 32090 | 13349 |
| CD11b− MHCII− CD11c+ | 1564 | 1073 | 1823 | 862 |

Example 9

Measurement of R1 mES Cell Growth, With and Without CCL21 Expression, in Balb/c Mouse Recipients As an indication of tolerization, a non-syngeneic allograft of R1 mES cells (from 129 mice) into Balb/c recipient mice was performed. ES control and ES 21+ were harvested from cell cultures and resuspended in sterile saline solution. A total of 10,000,000 cells in 100 μl saline were injected subdermally in the back of Balb/c mice after removal of fur. Teratoma volumes were measured daily and excised at 15 days after grafting.

Figure 13:
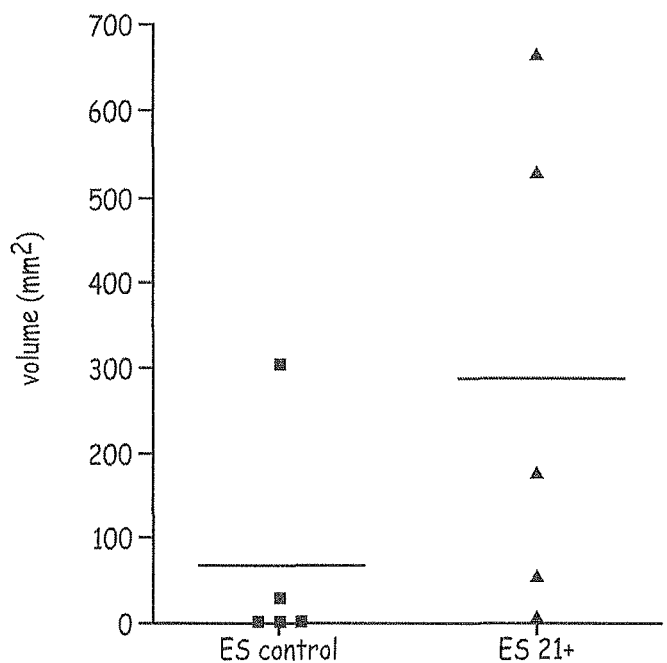
FIG. 13: R1 embryonic stem cells, either overexpressing CCL21 (ES 21+) or not (ES control) were implanted subcutaneously in mice in the non-syngeneic host Balb/c mouse. Teratoma volume was determined after explantation at 15 days post-grafting. Rejection of the embryonic stem cell transplant ensued in the absence of CCL21 overexpression, whereas tolerization ensued in the presence of CCL21 overexpression.

Measurement of teratoma size was performed with a digital caliber after excision and tumor volume was calculated with the ellipsoid formula. ES cells overexpressing CCL21 (ES 21+) formed significantly bigger teratomas (287 mm$^2$+ 294) than cells expressing low levels of CCL21 (ES control, 66 mm$^2$±133) (FIG. 13).

In addition to volume of the transplant being indicative of mES tolerization in the non-syngeneic allograft, differentiation of mES cells into teratomas was examined histologically.

Hematoxylin & eosin, van Giessen's trichrome and Miller's staining and alpha-SMA, CD31 and Lyve-1 immunostaining revealed the presence of well differentiated and functional arteries and veins, smooth muscle structures and adipose tissues throughout the teratomas. Histological analysis of the teratomas demonstrated clear presence of endoderm, mesoderm, and ectoderm, just supporting the tolerogenic potential of CCL21 when provided from the cellular transplant. Although ES cells do not display substantial amounts of MHC I, the differentiated cells coming from those cells do display normal amounts of MHC I; thus, these surprising results demonstrate that all cell types deriving from the ES cell transplants after they differentiate into teratomas can be induced to survive without chemotherapeutic immunosuppression in the host.

Thus, the R1 mES cells in a non-syngeneic-host were protected from rejection by tolerization due to CCL21 expression.

After the teratomas were surgically removed together with the skin, they were sectioned in half (part 1 and 2) and processed for (1) immunohistochemistry on thin sections for structural phenotyping and immune cell localization and (2) flow cytometry for immune cell panels to probe immune repertoires within the tumor. For (1) the Antibodies for the following targets have been used: ERTR7, gp38, CCL21, CD45, CD3e, F480, CD11c, B220, LYVE-1, CD31. For (2) the Antibodies for the following targets have been used: CD45, CD3ε, IL7Rα, γδ-TCR, CD25, CD4, CD8α, FoxP3, panNK, Tet-Trp2, CD19, MHCII, F4/80, CCR7/CD40/CD86/CD11b/CD11c/RORγt, Gr1.

Flow cytometry results showed that the percentage of CD45+ activated CD4 T regulatory cells (CD25+FoxP3+), and the total number of CD45+CCR7+cells, myeloid suppressor cells (CD11b+MHCII-GR1+), granulocytes (CD11b+MHCII-GR1int) and lymphoid immature DCs (CD11b-MHCII-CD11c+), were increased in ES masses overexpressing CCL21 (ES 21+) compared to the ones expressing low levels of CCL21 (ES control) while the percentage of CD45+CD8 T cells was decreased (Table 3).

TABLE 3

|  | Total Number of Cells | | | |
|---|---|---|---|---|
|  | ES control | | ES 21+ | |
|  | average | st dev | average | st dev |
| CD4+ CD25+ FoxP3+ | 0.50 | 0.5 | 1.78 | 0.67 |
| CD8+ % CD45+ | 1.46 | 1.09 | 0.70 | 0.45 |
| CD45+ CCR7+ | 7169 | 13390 | 13477 | 20255 |
| CD11b+ MHCII− GR1+ | 6633 | 10098 | 20610 | 35340 |

TABLE 3-continued

|  | Total Number of Cells | | | |
|---|---|---|---|---|
|  | ES control | | ES 21+ | |
|  | average | st dev | average | st dev |
| CD11b+ MHCII–GR1int | 25084 | 25241 | 69068 | 106542 |
| CD11b– MHCII–CD11c+ | 1560 | 3359 | 3088 | 3474 |

Example 10

Measurement of MDA Tumor Growth, With and Without CCL21 Expression, in Balb/c Mouse Recipients As an indication of tolerization, a xenograft of MDA tumor cells (from human) into Balb/c recipient mice was performed. Xenotolerization is a challenging goal in transplantation.

MDA control and MDA 21+ were harvested from cell cultures and resuspended in sterile saline solution. A total of 500,000 cells in 50 µl saline were injected subdermally in the back of Balb/c mice after removal of fur. Tumors were measured daily and excised at 16 days after grafting.

Figure 14:
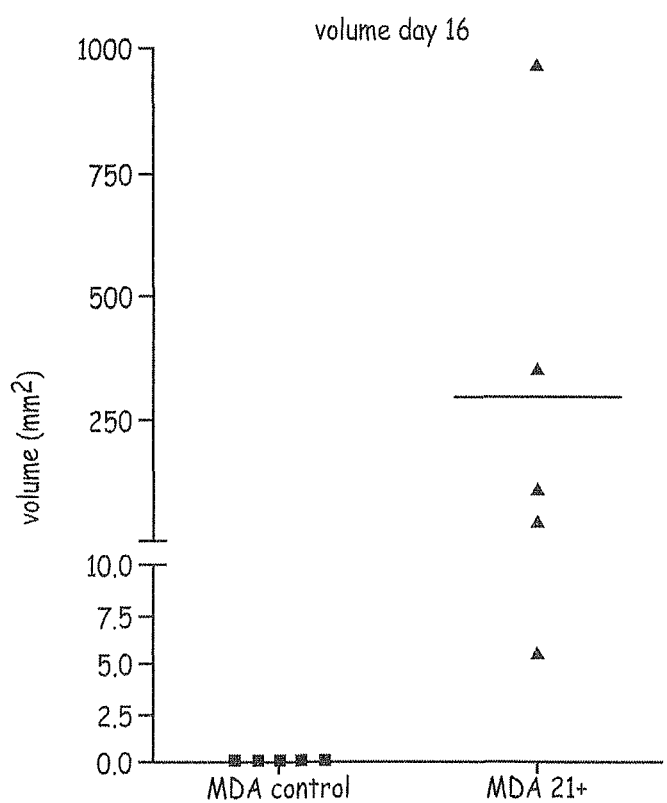
FIG. 14: MDA tumor cells (from human), either overexpressing CCL21 (MDA 21+) or not (MDA control) were implanted subcutaneously in mice in the non-syngeneic host Balb/c mouse. Teratoma volume was determined after explantation at 16 days post-grafting. Rejection of the MDA tumor cells transplant ensued in the absence of CCL21 overexpression, whereas tolerization ensued in the presence of CCL21 overexpression.

Measurement of tumor size was performed with a digital caliber after excision and tumor volume was calculated with the ellipsoid formula. MDA cells overexpressing CCL21 (MDA 21+) formed large tumors (314 mm$^2$±398) while tumors expressing low levels of CCL21 (MDA control) were not formed (FIG. 14).

After tumors were surgically removed together with the skin, they were sectioned in half (part 1 and 2) and processed for (1) immunohistochemistry on thin sections for structural phenotyping and immune cell localization and (2) flow cytometry for immune cell panels to probe immune repertoires within the tumor. For (1) the Antibodies for the following targets have been used: ERTR7, gp38, CCL21, CD45, CD3e, F480, CD11c, B220, LYVE-1, CD31. For (2) the Antibodies for the following targets have been used: CD45, CD3ε, IL7Rα, γδ-TCR, CD25, CD4, CD8α, FoxP3, panNK, Tet-Trp2, CD19, MHCII, F4/80, CCR7/CD40/CD86/CD11b/CD11c/RORγt, Gr1.

Flow cytometry results showed that the percentage of activated CD4 T regulatory cells (CD25+FoxP3+), and the total number of activated CD4 and CD8 T regulatory cells (CD25+FoxP3+), gamma delta T cells, CD45+CCR7+ cells, mature and immature myeloid DCs (CD11b+CD11c+F480-MHCII+ and MHC– respectively), myeloid suppressor cells (CD11b+MHCII-GR1+), granulocytes (CD11b+MHCII-GR1int) and lymphoid immature DCs (CD11b-MHCII-CD11c+), were increased in MDA tumors overexpressing CCL21 (MDA 21+) compared to the ones expressing low levels of CCL21 (MDA control) while both the percentage of CD45+CD8 T cells and the total number of CD8 T cells was decreased (Table 4). Thus, the MDA tumors in a xeno-host were protected from rejection by tolerization due to CCL21 expression.

TABLE 4

|  | Total Number of Cells | | | |
|---|---|---|---|---|
|  | MDA control | | MDA 21+ | |
|  | average | st dev | average | st dev |
| CD4+ CD25+ FoxP3+ | 39 | 68 | 868 | 927 |
| CD8+ | 20754 | 40298 | 8066 | 8770 |
| CD8+ CD25+ FoxP3+ | 11 | 15 | 50 | 41 |
| TCRγδ | 347 | 546 | 2239 | 2920 |
| CD4+ CD25+ FoxP3+ % CD45+ | 0.03 | 0.03 | 0.32 | 0.13 |
| CD8+ % CD45 | 7.52 | 5.53 | 3.53 | 1.38 |
| CD45+ CCR7+ | 206 | 240 | 2474 | 1665 |
| CD11b+ CD11c+ MHCII+ F480– | 61 | 63 | 777 | 1048 |
| CD11b+ CD11c+ MHCII– | 35 | 47 | 439 | 404 |
| CD11b+ MHCII– GR1+ | 277 | 252 | 1676 | 1042 |
| CD11b+ MHCII– GR1int | 597 | 459 | 6696 | 3014 |
| CD11b– MHCII– CD11c+ | 1030 | 1133 | 2895 | 2814 |

Example 11

Use of CCL19 in Tolerization

In this Example, CCL19 is to be used for tolerization. CCL19, like CCL21, is a ligand with CCR7 and has similar characteristics and activities. CCL21 possesses binding activity for proteoglycans, by virtue of a 32 amino acid long C-terminal tail comprising 12 basic amino acids (Yoshida, Nagira et al. 1998). The non-syngeneic allografts and xenografts expressing CCL19, analogously to treatment with CCL21 in the above examples, will be protected from immune rejected when CCL19 is delivered in a manner to provide sustained presence of the protein, for example by local expression as illustrated above or by local sustained administration. The proteoglycan-binding character of CCL19 is expected to influence mostly its local presence in tissue, which can be independently influenced by use of local expression or by sustained administration.

Example 12

Use of CCR7 Ligands in Combination with Other Immune-Regulatory Molecules

In this Example, one or more of these factors will be introduced, or expressed, with the CCL 19 and/or CCL21. The cytokine TGF-β and the interleukins IL10 and IL35 may be used beneficially with CCR7 ligands such as CCL21 to affect tolerization. In autoimmunity, it is known that regulatory T cells may be upregulated by the presence of TGF-β, IL10 and IL35 (Bettini and Vignali 2009). This biology may be usefully exploited in establishing allo- and even xenotolerance by co-delivery. Cellular transplants may be effectively treated with TGF-β, IL10 and/or IL35 (i.e., the three factors alone or in pairwise or triple combination), combined with CCR7 ligands to induce tolerance. This may be accomplished by co-expression of TGF-β, IL10 and/or IL35, with CCL21 from the cellular transplant, or by local sustained co-expression of TGF-β, IL10 and/or IL35 with CCL21 locally expressed or locally sustained. Although TGF-β, IL10 or IL35 alone is not expected to be sufficient to induce allotolerance or xenotolerance, TGF-β, IL10 and/or IL35 in combination with CCR7 ligands is expected to be beneficial.

The factors may be introduced systemically to a patient, in a culture medium during a cell-culture stage, by way of control release at or near materials placed into a patient, or by way of incorporation of nucleic acids that causes expression of the same. For instance, a cell may be engineered with a vector to express one or more of these factors. In some embodiments, a tissue or organ or a plurality of cells are treated, with some or all of the cells expressing CCL19 and/or CCL21, and some or all of the cells further expressing TGF-β, IL10 and/or IL35. Accordingly, a first set of cells may be treated to express a CCR7 ligand and a second set of cells treated to express TGF-β, IL10 and/or IL35, and the cells then combined (or the cells may already be part of the same tissue or organ).

Example 13

Controlled Release of CCL21 and CCL19 in the Graft Site

In this Example, CCL19 and/or CCL21 will be released over time ("controllably released") in association with a cell or a tissue or an organ. A large number of methods for controlled release of proteins exist, by which a prolonged presence of CCR7 ligands may be delivered, with or without other immune-regulatory cytokines such as TGF-β. In this way, the protein ligand for CCR7 may be provided, without the complexity of genetic modification (using stable expression systems as with lentiviral methods (Examples above) or plasmid transfection using nonviral methods. Proteins may be incorporated into drug pumps, into degradable polymers (e.g., using degradable polyesters or degradable hydrogels), or into biopolymer matrices (e.g., using fibrin), for example (Hubbell 2008).

A powerful approach is to express CCL21 as a fusion protein with a transglutaminase substrate sequence with or without an intervening protease substrates sequence, for example for plasmin or a matrix metalloproteinase, consistent with other examples present in the prior art (Schmoekel, Weber et al. 2005). The dosage and duration of dosing required to induce tolerance may be determined experimentally, using methods as described in the examples as read-outs in animal models. For example, measurement of cell viability and the cellular immune response in an allograft or a xenograft provides useful feedback in selecting an appropriate dose and dose duration.

Incorporated herein by reference for all purposes are U.S. Pat. Nos. 6,331,422, 6,607,740, 6,960,452, 7,241,730, and 7,247,609. CCL19 and/or CCL21 may be used for fusion polypeptides or nucleic acids encoding the same. Further components of such fusion molecules may be, e.g., transglutaminase substrates, heparin-binding domains, fibrin-binding domains, and/or protease substrates. Moreover, such fusion molecules may comprise, or encode, TGF-β and/or IL10 and/or IL35. Some embodiments provide for a set of fusion molecules, with each fusion molecule being provided with a motif for binding to fibrin and one or more of CCL19 and/or CCL21 and/or TGF-β and/or IL10 and/or IL35. Various combinations of the binding motifs and factors may be provided, i.e., not every fusion molecule necessarily has to be identical to the other. Some embodiments provide for a fibrin matrix to be formed at or near a cell, tissue, or organ that expresses CCL19 and/or CCL21. The matrix may include one or more of these various fusion polypeptides. Alternatively, cells associated with the matrix may include DNA that encodes one or more of the CCL19 and/or CCL21 and/or a fusion molecule. In one embodiment, the fibrin matrix is placed with such cells, e.g., the matrix coats the cells (or organ or tissue) or the cells are dispersed therein. Or the matrix may be placed nearby.

Example 14

Production of CCL21 Fusion Protein with Transglutaminase Substrate Domain

The two recombinant proteins CCL21-(P1 C1)-TG and TG-(P1 C1)-CCL21 for a controlled release of CCL21 from fibrin gels have been produced as indicated below. The nomenclature "TG" indicates a fusion protein with a transglutaminase substrate, NQEQVSPL (SEQ ID NO:10), derived from the N-terminal eight amino acids of the transglutaminase factor XIIIa substrate alpha(2) plasmin inhibitor. This substrate domain becomes covalently coupled into fibrin matrices under the enzymatic action of factor XIIIa during fibrin polymerization and coagulation. A protease cleavage domain, for example sensitive to plasmin (P1 C1) may or may not be added between the CCL21 domain and the transglutaminase immobilization site, to provide for a cellular means of release of the CCL21.

The two recombinant proteins: CCL21-(P1 C1)-TG and TG-(P1 C1)-CCL21 for a controlled release of CCL21 from fibrin gels have been produced as indicated below. The genes coding for CCL21-(P1 C1)-TG and TG-(P1 C1)-CCL21 were constructed by PCR amplification of the cDNA of CCL21 and cloned into pORFS-mExodus2 v.21 plasmid (Invivogen, San Diego, Calif.) with primers targeting CCL21 serine (ATG-GCTCAGATGATGACTCTGAGCCTCCT-TAGCCTGGTCCTGGCTCTCTGCATCCCC TGGAC-CCAAGGCAGTGATGGAGGGGGTCAGGACTGCTGCC TTAAGTACAGCCAGAA GAAAATTCCCTACAGTAT-TGTCCGAGGCTATAGGAAGCAAGAAC-CAAGTTTAGGCT GTCCCATCCCGGCAATCCTGT-TCTCACCCCGGAAGCACTCTAAGCCTGAGCTATGTG CAAACCCTGAGGAAGGCTGGGTGCA-GAACCTGATGCGCCGCCTGGACCAGCCTCCA GCCCCAGGGAAACAAAGCCCCGGCTG-CAGGAAGAACCGGGGAACCTCTAAGTCTGG AAA-GAAAGGAAAGGGCTCCAAGGGCTGCAA-GAGAACTGAACAGACACAGCCCTCA AGAGGATAG) (SEQ ID NO:11). Codons for the TG sequence (AACCAG-GAGCAGGTGAGCCCCCTG) (SEQ ID NO:12) and the plasmin cleavable site (CCCGTGGAGCTGCCCCTGAT-CAAGATGAAGCCC) (SEQ ID NO:13) were added to the C-terminus of CCL21ser, creating CCL21-(P1 C1)-TG, and at the N-terminus of CCL21ser sequence, creating TG-(P1 C1)-CCL21 (inserted after the signal sequence ahead (ATG-GCTCAGATGATGACTCTGAGCCTCCT-TAGCCTGGTCCTGGCTCTCTGCATCCCC TGGAC-CCAAGGC) (SEQ ID NO:14). Restriction sites have been added at the beginning and end of the two genes: NcoI and NheI respectively. PCR products were digested with the selected restrictions enzymes (NcoI and NheI) for 4 hours at 37° C. and subcloned into the pORF5-mExodus2 v.21 plasmid in place of CCL21ser by quick ligation with the quick ligation kit (BioLabs) for 10 minutes at room temperature. Competent *E. coli* were transformed with the ligated vectors containing the CCL21-(P1 C1)-TG (plasmid 1) or the TG-(P1 C1)-CCL21 (plasmid 2). Plasmid DNA was purified from antibiotic-resistant colonies and the gene sequence was confirmed by DNA sequencing (Fasteris).

Plasmid 1 and plasmid 2 will be amplified and purified by MAXIPREP (Nucleobond ax) and transfected separately in mammalian cells. Supernatants containing the CCL21-(P1

C1)-TG (plasmid 1) or the TG-(P1 C1)-CCL21 (plasmid 2) recombinant proteins will be collected after 3, 5 and 7 days, pooled together and run through an heparin column. CCL21 affinity for heparin allows purification of the two recombinant proteins from the supernatants. The proteins are to be further purified by size exclusion chromatography. SDS-PAGE followed by silver staining and western blotting for CCL21 confirms the purity of the two recombinant proteins.

Function of CCL21-(P1 C1)-TG and TG-(P1 C1)-CCL21 as chemoattractant for CCR7+ cells is to be confirmed by placing whole spleen lysates atop of 8 µm pore transwells (Millipore) with either CCL21-(P1 C1)-TG crosslinked fibrin gels or TG-(P1 C1)-CCL21 crosslinked fibrin gels both with and without plasmin (to degrade the fibrin gel and speed-up CCL21 release) and CCR7 blocking antibodies. Fibrin gels are to be produced by mixing 8 mg/ml fibrinogen with a crosslinking solution of factorXIII (8 U/ml), thrombin (2 U/ml) and CaCl2 (2.5 M) and with different amounts of either TG-(P1 C1)-CCL21 or CCL21-(P1 C1)-TG.

CCL19 may be treated in the same manner as described for CCL21.

Example 15

Tolerization to Cellular Allografts or Xenografts

In this Example, cellular transplantation is to be used for treatment of a number of diseases and other maladies. For example, stem cells are used in a number of applications in regenerative medicine. The ability to use a tolerogenic protocol to tolerize the recipient against the transplanted cells would reduce or eliminate the requirement to immune HLA restriction type matching of the donor cells to the recipient. Delivery of CCR7 ligands, by either genetic or pharmacological means as described in the Examples above, alone or with other immune-regulatory cytokines such as TGF-β, is expected to achieve this. Examples of use are transplantation of stem cells for restoration of muscle in Duchene's muscular dystrophy, transplantation of islets of Langerhans for restoration of glucose sensitivity in type-I diabetes mellitus, transplantation of stem cell-derived pancreatic beta cell-like cells for restoration of glucose sensitivity in type-I diabetes mellitus, transplantation of cardiomyocytes or stem cell-derived cardiomyocyte precursors to restore cardiac function, endothelial cells or endothelial progenitor cells to correct angiogenic deficits in tissues for example in therapeutic revascularization of the heart after myocardial infarction, and cells such as C2C12 cells for local expression and secretion of exogenous therapeutic proteins being produced by the transplanted cells. Importantly, an initial treatment of the patient for tolerization with a small and localized transplant of a cellular or cell cluster graft can be carried out, followed by a broader and less localized treatment with the cellular transplant after tolerization has been achieved. This is to say, localized initial tolerization of the cell transplant with the CCR7 ligand is expected to provide protection of a subsequent cellular transplant carried out in the absence of the CCR7 ligand being co-expressed or locally delivered. An additional benefit that can be expected is reduction of the burden that is placed on any pharmacological immunosuppressive regimen that is used to product the cellular transplant.

Example 16

Tolerization to Encapsulated Cellular or Cell Cluster Allografts or Xenografts

In this Example, encapsulation of cellular and cell cluster allografts and xenografts within membrane devices will be utilized to provide partial immune protection from rejection by a non-syngeneic recipient or non-HLA restriction matched recipient. The ability to use a tolerogenic protocol to tolerize the recipient against the transplanted cells is expected to reduce or eliminate the burden placed on the membrane device or the burden on any pharmacological immunosuppressive regimen that is used to product the encapsulated cellular transplant. Co-delivery of CCR7 ligands, by either genetic or pharmacological means as described herein or in the Examples, alone or with other immune-regulatory cytokines such as TGF-β, is expected to achieve this. One mode that can be valuable is tolerization with a non-encapsulated transplant with co-delivery of CCR7 ligands as described herein, affecting tolerization, followed by use of the encapsulated cells. Another mode that can be valuable is encapsulation of CCR7 ligand expressing cells, or co-encapsulation of CCR7 ligands within the membrane device free or within a controlled release material as described above. Examples of use include transplantation of encapsulated islets of Langerhans, transplantation of stem cell-derived pancreatic beta cell-like cells, and transplantation of encapsulated cells expressing a transgene for the purpose of producing a therapeutic protein.

Example 17

Tolerization to Tissue Allografts or Xenografts

Tolerization of tissue grafts is an important challenge with all tissue, including organ, transplantation. The ability to use a tolerogenic protocol to tolerize the recipient against the transplanted tissues, including organs, reduces or eliminate the burden placed on pharmacological immunosuppression.

An example is provided here, in the context of skin transplantation, in which skin is to be transplanted using a biomaterial matrix, e.g., fibrin, between the transplanted skin and the recipient tissue bed, the biomaterial matrix containing a CCR7 ligand admixed or bound to the matrix or within a controlled release material (see Examples herein). The dosage and duration of dosing required to induce tolerance may be determined experimentally, using methods as described herein. For example, following cell viability and the immune response in an allograft or a xenograft provides useful feedback in selecting an appropriate dose and dose duration.

Vectors

Certain embodiments of the invention are directed to a vector that encodes CCL19 and/or CCL21 and/or a fragment of the same that binds to CCR7. Nucleic acids can be incorporated into vectors. A vector is a broad term that includes any specific DNA segment that is designed to move from a carrier into a target DNA. A vector may be referred to as an "expression vector", or a vector system, which is a set of components needed to bring about DNA insertion into a genome or other targeted DNA sequence such as an episome, plasmid, or even virus/phage DNA segment. Vector systems such as viral vectors (e.g., retroviruses, adeno-associated virus and integrating phage viruses), and non-viral vectors (e.g., transposons) used for gene delivery in animals have two basic components: 1) a vector comprised of DNA (or RNA that is reverse transcribed into a cDNA) and 2) a transposase, recombinase, or other integrase enzyme that recognizes both the vector and a DNA target sequence and inserts the vector into the target DNA sequence.

Vectors most often contain one or more expression cassettes that comprise one or more expression control sequences, wherein an expression control sequence is a DNA sequence that controls and regulates the transcription and/or translation of another DNA sequence or mRNA, respectively. Expression control sequences include, for example, promoter sequences, transcriptional enhancer elements, start codons, stop codons, and any other nucleic acid elements required for RNA polymerase binding, initiation, or termination of transcription. A wide range of expression control sequences is well known in the art and is commercially available. With respect to expression control sequences, the term 'operably linked' means that the expression control sequence and the inserted nucleic acid sequence of interest (also referred to herein as the exogenous nucleic acid sequence that is intended to be expressed, also referred to as the exogenous nucleic acid sequence) are positioned such that the inserted sequence is transcribed (e.g., when the vector is introduced into a host cell). A transcriptional unit in a vector may thus comprise an expression control sequence operably linked to an exogenous nucleic acid sequence. For example, a DNA sequence is operably linked to an expression-control sequence, such as a promoter when the expression control sequence controls and regulates the transcription and translation of that DNA sequence. The term "operably linked" includes having an appropriate start signal (e.g., ATG) in front of the DNA sequence to be expressed for translation and maintaining the correct reading frame to permit expression of the DNA sequence under the control of the expression control sequence to yield production of the desired protein product.

There are a variety of promoters that could be used including, e.g., constitutive promoters, tissue-specific promoters, and inducible promoters. Promoters are regulatory signals that bind RNA polymerase in a cell to initiate transcription of a downstream (3'-direction) coding sequence.

Many different types of vectors are known. For example, plasmids and viral vectors, e.g., retroviral vectors, are known. Mammalian expression plasmids typically have an origin of replication, a suitable promoter and optional enhancer, and also any necessary ribosome binding sites, a polyadenylation site, splice donor and acceptor sites, transcriptional termination sequences, and 5' flanking non-transcribed sequences. In addition, the expression vectors preferably contain a gene to provide a phenotypic trait for selection of transformed host cells such as neomycin resistance for eukaryotic cell culture, or tetracycline or ampicillin resistance in E. coli. Retroviral vectors, which typically transduce only dividing cells, can be used. Adenoviral vectors, capable of delivering DNA to quiescent cells can be used. Another viral vector system with potential advantages is an adeno-associated viral vector. Examples of vectors include: plasmids (which may also be a carrier of another type of vector), adenovirus, adeno-associated virus (AAV), lentivirus (e.g., modified HIV-1, SIV or FIV), retrovirus (e.g., ASV, ALV or MoMLV), and transposons (e.g., Sleeping Beauty, P-elements, Tol-2, Frog Prince, piggyBac).

Transposons or transposable elements comprise a section of nucleic acid sequence bounded by repeat sequences. Active transposons encode, along with other proteins, transposase enzymes that facilitate the insertion of the nucleic acid into DNA sequences. These transposable elements transpose through a cut-and-paste mechanism; the element-encoded transposase catalyzes the excision of the transposon from its original location and promotes its reintegration elsewhere in the genome. A transposase protein is capable of binding to DNA at sequences termed inverted terminal repeats. Transposons typically contain at least one, and sometimes two, sets of inverted repeats that respectively flank an intervening nucleic acid sequence. The transposase binds to recognition sites in the inverted repeats and catalyzes the incorporation of the transposon into genomic DNA, generally at repeat sequences representing transposon insertion sites. Various transposases are known, e.g., Sleeping Beauty, or Tol2.

As used herein, the term nucleic acid refers to both RNA and DNA, including, for example, cDNA, genomic DNA, synthetic (e.g., chemically synthesized) DNA, as well as naturally occurring and chemically modified nucleic acids, e.g., synthetic bases or alternative backbones. A nucleic acid molecule can be double-stranded or single-stranded (i.e., a sense or an antisense single strand).

Markers may be introduced. Marker molecules include, for example, those molecules that are detectable upon expression. Many experimental regimens benefit from marker molecules used in vivo in experimental animals or in vitro cell cultures for identification of transfected cells. Examples of marker molecules are fluorescent proteins, Green Fluorescent Protein, b-galactosidase, secreted alkaline phosphatase, luciferase and chloramphenicol acetyltransferase.

A small gene delivery system has advantages with respect to penetrating tissue. In some embodiments, therefore, the delivery system uses significantly condensed DNA to transfect cells. In some embodiments, therefore, ligands are attached to polymers which contain a nuclear localisation sequence to form a conjugate and are used to condense DNA to overcome challenges to gene transfection in chondrocytes embedded in the cartilage matrix. Some aspects of these techniques have been described in Trentin et al. PNAS 2006; 103:2506-11 and J Control Release 2005; 102:263-75 (hereby incorporated herein by reference for methods and compositions). This in certain embodiments the conjugate associated with nucleic acids encoding a polypeptide is prepared and introduced into the body as a purified composition in a pharmaceutically acceptable condition, or with a pharmaceutical excipient. In certain embodiments, such a conjugate is produced using a cell, either a procaryotic or a eucaryotic cell. In other embodiments, transfected cells are introduced into a patient.

Polypeptide Delivery and Release

Polypeptides as described herein can be attached to other polymers through bioconjugation. The formation of such conjugates is within the skill of ordinary artisans and various techniques are known for accomplishing the conjugation, with the choice of the particular technique being guided by the materials to be conjugated. The addition of amino acids to the polypeptide (C- or N-terminal) which contain ionizable side chains, i.e. aspartic acid, glutamic acid, lysine, arginine, cysteine, histidine, or tyrosine, and are not contained in the active portion of the polypeptide sequence, serve in their unprotonated state as a potent nucleophile to engage in various bioconjugation reactions with reactive groups attached to polymers, i.e. homo- or hetero-bi-functional PEG (e.g., Lutolf and Hubbell, Biomacromolecules 2003; 4:713-22, Henuanson. Bioconjugate Techniques. London. Academic Press Ltd; 1996). In some embodiments, the agent is attached to a soluble polymer, and may be adminsited to a patient in a pharmaceutically acceptable form. Or a drug may be encapsulated in polymerosomes or vesicles or covalently attached to polymers. In the latter case, drugs are attached to the polymer backbone with a degradable site-specific spacer or linker (Lu et al. J Control Release 2002; 78:165-73).

In general, soluble hydrophilic biocompatbile polymers may be used to ensure that the conjugate is soluble and will be bioavailable after introduction into the patient. Examples of soluble polymers are polyvinyl alcohols, polyethylene imines, and polyethylene glycols (a term including polyethylene oxides) having a molecular weight of at least 100, 400, or between 100 and 400,000 (with all ranges and values between these explicit values being contemplated). Solubility refers to a solubility in water or physiological saline of at least 1 gram per liter. Domains of biodegradable polymers may also be used, e.g., polylactic acid, polyglycolic acid, copolymers of polylactic and polyglycolic acid, polycaprolactones, polyhydroxy butyric acid, polyorthoesters, polyacetals, polydihydropyrans, and polycyanoacylates.

In some embodiments, a polypeptide-polymer association, e.g., a conjugate, is prepared and introduced into the body as a purified composition in a pharmaceutically acceptable condition, or with a pharmaceutical excipient. The site of introduction may be, e.g., systemic, or at a tissue or a transplantation site.

A variety of chemical schemes can be used to incorporate a polypeptide as disclsoed herein into a biomaterial, e.g., for delivery or controlled release. For example, using a material as described by Sawhney et al., a chemical approach for incorporation as described by Hern et al. can be employed (Sawhney et al. Macromolecules 1993; 26:581-587 and Hern et al. J. Biomed. Mater. Res. 1998; 39:266-276). As another example, using a material as described by Lutolf et al., a chemical approach for incorporation as described therein can be employed (Lutolf et al. Nature Biotechnol. 2003; 21:513-518). In general, the modification of such biomaterials is within the skill of ordinary artisans and various techniques are known for accomplishing the modification, with the choice of a particular technique being guided by the biomaterial and peptides to be conjugated.

Accordingly, embodiments include biomaterials comprising at least one of the ligands disclosed herein that specifically bind a CCR7 receptor. In some embodiments, the biomaterial is a solid prior to placement in a patient, while in other embodiments the material is made is situ, meaning it is formed from precursors at the site of the defect. This biomaterials may be supplemented with a ligand or other embodiment set forth herein. Examples of such biomaterials include U.S. Pat. Nos. 5,874,500, and 5,410,016, and which include materials formed by in-situ polymerization. Further examples of materials and drug delivery processes are found in U.S. Pat. Nos. 4,687,481, 5,279,544, 5,330,768, 5,468,505, 5,558,642, 5,648,506, 6,322,804, 6,629,949, 6,828,401, 7,186,413, 7,250,037, 7,291,673, 7,332,586, 7,432,239, 7,803,748, and U.S. Pub. Nos. US 2006/0193787, 2009/0202640, US 2009/0232899, US 2009/0297613, all of which are hereby incorproated by reference herein for all purposes and including for delivery of one or more chemokines and/or agents; in case of conflict, the instant specification controls.

Specific binding, as that term is commonly used in the biological arts, generally refers to a molecule that binds to a target with a relatively high affinity compared to non-target tissues, and generally involves a plurality of non-covalent interactions, such as electrostatic interactions, van der Waals interactions, hydrogen bonding, and the like. Specific binding interactions characterize antibody-antigen binding, enzyme-substrate binding, and specifically binding protein-receptor interactions; while such molecules may bind tissues besides their targets from time to time, such binding is said to lack specificity and is not specific binding. Embodiments include CCL19 and CCL21 chemokines that specifically bind CCR7.

The terms CCL19 chemokine and CCL21 chemokine refer to the whole chemokine and also to fragments thereof that specifically bind to CCR7, as well as conservative substitutions of the whole chemokine or a fragment thereof that exhibit such binding. Once an artisan has read this specification, the preparation of such fragments and substitutions can be readily performed using techniques known to those practicing in these fields. Moreover, sequences and subsequences that exhibit binding and bioactivity may reasonably be expected to be prepared with 90%, 95% or 99% homology to CCL19 and/or CCL21.

Nucleic Acids

Certain embodiments are directed to nucleic acids. As used herein, the term nucleic acid refers to both RNA and DNA, including siRNA, shRNA, miRNA, cDNA, genomic DNA, synthetic (e.g., chemically synthesized) DNA, as well as naturally occurring and chemically modified nucleic acids, e.g., synthetic bases or alternative backbones. A nucleic acid molecule can be double-stranded or single-stranded (i.e., a sense or an antisense single strand). A conservatively substituted nucleic acid refers to the substitution of a nucleic acid codon with another codon that encodes the same amino acid and also refers to nucleic acids that encode conservatively substituted amino acids, as described herein with respect to polypeptides.

The nucleic acid sequences set forth herein are intended to represent both DNA and RNA sequences, according to the conventional practice of allowing the abbreviation "T" stand for "T" or for "U", as the case may be, for DNA or RNA. Polynucleotides are nucleic acid molecules of at least three nucleotide subunits. Polynucleotide analogues or polynucleic acids are chemically modified polynucleotides or polynucleic acids. In some embodiments, polynucleotide analogues can be generated by replacing portions of the sugar-phosphate backbone of a polynucleotide with alternative functional groups. Morpholino-modified polynucleotides, referred to herein as "morpholinos," are polynucleotide analogues in which the bases are linked by a morpholino-phosphorodiamidate backbone (see, e.g., U.S. Pat. Nos. 5,142,047 and 5,185,444). In addition to morpholinos, other examples of polynucleotide analogues include analogues in which the bases are linked by a polyvinyl backbone, peptide nucleic acids (PNAs) in which the bases are linked by amide bonds formed by pseudopeptide 2-aminoethyl-glycine groups, analogues in which the nucleoside subunits are linked by methylphosphonate groups, analogues in which the phosphate residues linking nucleoside subunits are replaced by phosphoroamidate groups, and phosphorothioated DNAs, analogues containing sugar moieties that have 2' O-methyl group). Polynucleotides of the invention can be produced through the well-known and routinely used technique of solid phase synthesis. Alternatively, other suitable methods for such synthesis can be used (e.g., common molecular cloning and chemical nucleic acid synthesis techniques). Similar techniques also can be used to prepare polynucleotide analogues such as morpholinos or phosphorothioate derivatives. In addition, polynucleotides and polynucleotide analogues can be obtained commercially. For oligonucleotides, examples of pharmaceutically acceptable compositions are salts that include, e.g., (a) salts formed with cations such as sodium, potassium, ammonium, etc.; (b) acid addition salts formed with inorganic acids, for example, hydrochloric acid, hydrobromic acid (c) salts formed with organic acids e.g., for example, acetic acid, oxalic acid, tartaric acid; and (d) salts formed from elemental anions e.g., chlorine, bromine, and iodine.

Polypeptides

There are a variety of conservative changes that can generally be made to an amino acid sequence without altering activity. These changes are termed conservative substitutions or mutations; that is, an amino acid belonging to a grouping of amino acids having a particular size or characteristic can be substituted for another amino acid. Substitutes for an amino acid sequence may be selected from other members of the class to which the amino acid belongs. For example, the nonpolar (hydrophobic) amino acids include alanine, leucine, isoleucine, valine, proline, phenylalanine, tryptophan, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such alterations are not expected to substantially affect apparent molecular weight as determined by polyacrylamide gel electrophoresis or isoelectric point. Exemplary conservative substitutions include, but are not limited to, Lys for Arg and vice versa to maintain a positive charge; Glu for Asp and vice versa to maintain a negative charge; Ser for Thr so that a free —OH is maintained; and Gln for Asn to maintain a free $NH_2$. Moreover, point mutations, deletions, and insertions of the polypeptide sequences or corresponding nucleic acid sequences may in some cases be made without a loss of function of the polypeptide or nucleic acid fragment. Substitutions may include, e.g., 1, 2, 3, or more residues. The amino acid residues described herein employ either the single letter amino acid designator or the three-letter abbreviation. Abbreviations used herein are in keeping with the standard polypeptide nomenclature, J. Biol. Chem., (1969), 243, 3552-3559. All amino acid residue sequences are represented herein by formulae with left and right orientation in the conventional direction of amino-terminus to carboxy-terminus.

In some cases a determination of the percent identity of a peptide to a sequence set forth herein may be required. In such cases, the percent identity is measured in terms of the number of residues of the peptide, or a portion of the peptide. A polypeptide of, e.g., 90% identity, may also be a portion of a larger peptide. Embodiments include such polypeptides that have the indicated identity and/or conservative substitution of a CCL19 and/or CCL21 sequence set forth herein, with said polypeptides exhibiting specific binding to CCR7 receptors.

The term purified as used herein with reference to a polypeptide refers to a polypeptide that either has no naturally occurring counterpart (e.g., a peptidomimetic), or has been chemically synthesized and is thus substantially uncontaminated by other polypeptides, or has been separated or purified from other most cellular components by which it is naturally accompanied (e.g., other cellular proteins, polynucleotides, or cellular components). An example of a purified polypeptide is one that is at least 70%, by dry weight, free from the proteins and naturally occurring organic molecules with which it naturally associates. A preparation of a purified polypeptide therefore can be, for example, at least 80%, at least 90%, or at least 99%, by dry weight, the polypeptide. Polypeptides also can be engineered to contain a tag sequence (e.g., a polyhistidine tag, a myc tag, or a FLAG® tag) that facilitates the polypeptide to be purified or marked (e.g., captured onto an affinity matrix, visualized under a microscope). Thus a purified composition that comprises a polypeptide refers to a purified polypeptide unless otherwise indicated.

Polypeptides may include a chemical modification; a term that, in this context, refers to a change in the naturally-occurring chemical structure of amino acids. Such modifications may be made to a side chain or a terminus, e.g., changing the amino-terminus or carboxyl terminus. In some embodiments, the modifications are useful for creating chemical groups that may conveniently be used to link the polypeptides to other materials, or to attach a therapeutic agent.

Some embodiments of the invention are fusion polypeptides that include CCL19 and/or CCL21 and/or fragments thereof that bind to the CCR7 receptor, as well as variations of the same. Embodiments include a fusion protein comprising a member of the group consisting of CC-chemokine ligand-19 (CCL19), CC-chemokine ligand-19 (CCL21), and fragments thereof that specifically bind CC-chemokine receptor 7 (CCR7). The fusion protein may comprise a conservative substitution of CCL19, CCL21, or the fragments thereof. The fusion protein may comprise a protein chosen from the group consisting of a transglutaminase substrate, a heparin-binding domain, a fibrin-binding domain, a protease substrate, Transforming Growth Factor beta (TGF-β), Interleukin-10 (IL-10), and Interleukin-35 (IL-35). The fusion protein may comprise a motif for binding to fibrin and a member of the group consisting of Transforming Growth Factor beta (TGF-β), Interleukin-10 (IL-10), Interleukin-35 (IL-35). The fusion protein may comprise a transglutaminase substrate and a plasmin substrate.

Artisans may prepare fusion proteins using techniques known in these arts. Embodiments include preparing fusion proteins, isolating them, and administering them in a pharmaceutically acceptable form with or without other agents, e.g., in combination with an interleukin of TGF-beta. Embodiments include a vector for, and methods of, transfecting a cell to thereby engineer the cell to make the fusion protein in vivo, with the cell being transfected in vitro, ex vivo, or in vivo, and with the cell being a member of a tissue implant or distinct therefrom. The following U.S. patent applications are hereby incorporated by reference herein for all purposes, including the purposes of making fusion proteins, with the instant specification controlling in case of conflict: U.S. Pat. Nos. 5,227,293, 5,358,857, 5,885,808, 5,948,639, 5,994,104, 6,512,103, 6,562,347, 6,905,688, 7,175,988, 7,704,943, US 2002/0004037, US 2005/0053579, US 2005/0203022, US 2005/0250936, US 2009/0324538.

Pharmaceutical Carriers, Administration

Pharmaceutically acceptable carriers or excipient may be used to deliver embodiments as described herein. Excipient refers to an inert substance used as a diluent or vehicle for a therapeutic agent. Pharmaceutically acceptable carriers are used, in general, with a compound so as to make the compound useful for a therapy or as a product. In general, for any substance, a pharmaceutically acceptable carrier is a material that is combined with the substance for delivery to an animal. Conventional pharmaceutical carriers, aqueous, powder or oily bases, thickeners and the like may be necessary or desirable. In some cases the carrier is essential for delivery, e.g., to solubilize an insoluble compound for liquid delivery; a buffer for control of the pH of the substance to preserve its activity; or a diluent to prevent loss of the substance in the storage vessel. In other cases, however, the carrier is for convenience, e.g., a liquid for more convenient administration. Pharmaceutically acceptable salts of the compounds described herein may be synthesized according to methods known to those skilled in this arts. Thus a pharmaceutically acceptable composition has a carrier, salt, or excipient suited to administration to a patient. Moreover, inert components of such compositions are biocompatible and not toxic.

The compounds described herein may be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. Thus the deliverable compound may be made in a form suitable for oral, rectal, topical, intravenous injection, or parenteral administration. Carriers include solids or liquids, and the type of carrier is chosen based on the type of administration being used. Suitable binders, lubricants, disintegrating agents, coloring agents, flavoring agents, flow-inducing agents, and melting agents may be included as carriers, e.g., for pills. For instance, an active component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. The compounds can be administered orally in solid dosage forms, such as capsules, tablets, and powders, or in liquid dosage forms, such as elixirs, syrups, and suspensions. The active compounds can also be administered parentally, in sterile liquid dosage forms. Buffers for achieving a physiological pH or osmolarity may also be used.

The ligands and other agents (for example T-cell up-regulators, interleukins, and/or growth factor(s)) may be administered before, during, or after a tissue implant is performed. Systemic and/or local administration may be used.

Immunosuppressant drugs may further be used in combination with the ligands. Once tolerization is achieved, immunosuppressant drugs may be withdrawn and not further administered as part of the treatment process involving implantation of the tissue. Immunosuppressive drugs include, for example, glucocorticoids, cytostatics, antimetabolites, azathioprine, mercaptopurine, cytotoxic antibiotics, tacrolimus, rapamycin, ciclosrporin, certain antibodies, e.g., against T-cells, T-cell receptors, IL-2 receptors. Embodiments include administering a ligand or ligands until such time as tolerization is achieved and then ending the administration. Administration refers to an ongoing process of supplying a dose to a patient; e.g., daily or weekly over a period of time. Embodiments include, for example, a maximum time duration of administration, with the maximum time being between one week and 52 weeks; artisans will immediately appreciate that all the ranges and values within the explicitly stated ranges are contemplated, e.g., one month, two months, or six months.

CCL19 and/or CCL21 are not, at this time, conventional immunosuppressants. If these were to be used as immunosuppressants, the ligands need to be present at a high enough level systemically to interact with a meaningful quantity of CCR7 receptors. Achieving such quantities would require a concentration that exceeds the concentrations that are to be expected for tolerization. Embodiments include administering amounts of CCR7 ligands that are effective to achieve tolerization but are not effective to achieve immunosuppression.

Additional Disclosure

Certain embodiments are directed to a vector comprising a nucleic acid encoding at least a portion of CCL19 and/or CCL21 that specifically binds to CCR7. Embodiments also include a cell (in vitro, ex vivo, or in vivo) comprising such a vector, or a cell overexpressing at least a portion of CCL19 and/or CCL21 that specifically binds to CCR7. Embodiments include human and non-human cells. The cell may be isolated, or part of a tissue. The term tissue herein is used broadly and includes individual cells, cell clusters, and organs. Embodiments also include a method of inducing tolerization in a patient, the method comprising placing a cell expressing one or more of the chemokines into the patient, or one of the vectors into the patient. Embodiments include a composition or method of inducing tolerization in a patient, comprising obtaining a cell from a donor that is allogeneic (or non-syngeneic) or xenogeneic relative to the patients, and engineering the cell to express CCL19 and/or CCL21 and placing the cell into the patient. The cells or tissues may be encapsulated and placed into the patient. In any of these approaches, one or more factors may be introduced in association with the chemokines. Factors include TGF-β and/or the interleukins IL10 and/or IL35. The factors may be introduced systemically to a patient, in a culture medium during a cell-culture stage, by way of control release at or near materials placed into a patient, or by way of incorporation of nucleic acids that causes expression of the same.

Further embodiments include a fusion polypeptide that comprises one or both of CCL19 and CCL21, or a fragment thereof. The polypeptide may be comprising one or more of TGF-β and/or the interleukins IL10 and/or IL35. It may be further comprising a transglutaminase substrate sequence. The fusion polypeptide may further comprise a protease substrate. The protease that is specific to the substrate may cleave fibrin moieties, e.g., a substrate specifically cleaved by a plasmin or a matrix metalloproteinase. A vector may be created to express one or more of the fusion polypeptides.

A cell may be engineered to incorporate one or more of these vectors. Cells may be, e.g., in vitro, ex vivo, in vivo, human, or non-human. The cells may be part of the tissue that is desired to be implanted into a patient, and for which tolerization is desired, or the cells may be from other sources and administered to the patient in conjunction with such an implant. For instance some cells of an implant may be thusly modified, or modified cells mixed into the implant. The mixing may be accomplished by co-introduction or the cells may be co-cultured with the implant material in vitro. Moreover, the co-culture may be done with a matrix, either two-dimensionally (on the matrix) or in 3D (inside the matrix). For instance a fibrin matrix (or other matrix) may be formed around tissue that is to be implanted, along with cells engineered to express one or more of the ligands or factors. Instead of cells, organs or other tissues may be mixed with a matrix and introduced accordingly. Examples of matrices are hydrogels made of natural or synthetic polymers, e.g., biodegradable, hydrophilic polymers.

Some embodiments are a composition for enhancing a transplant of a cell, the composition comprising CCL19 and/or CCL21, or at least a portion of CCL19 and/or CCL21 that specifically binds to CCR7. Some embodiments are a method of enhancing a transplant of a cell, the method comprising introducing CCL19 and/or CCL21 at least a portion of CCL19 and/or CCL21 that specifically binds to CCR7, in association with the cell. The cell may be a member of a tissue. The cell may be human or non-human. The CCL19 and/or CCL21 or portion thereof may be locally administered, meaning it is applied at or near a to a site intended to receive the transplant, and meaning not-systematically administered. At a site means touching the implant tissue at the time of implantation. Nearby means that the area of effect is local and not throughout the body. Alternatively, the area administration may be specified in distance, with an example being within about 10 cm; artisans will immediately appreciate that all the ranges and values within the explicitly stated ranges are contemplated, e.g., 0 to about 5 cm or less than about 2 cm.

The CCL19 and/or CCL21 or portion thereof may part of a composition for release of the same to the transplant. Release vehicles include, for example, a matrix for controlled release of the CCR7 ligand(s), or a particle that comprises the CCR7 ligand(s), or a combination thereof. Examples of particles are liposomes, nanoparticles, and micelles. Examples of matrices are fibrin, alginates, fibrin sealants, and medical sealants that comprise polyethylene glycol (e.g., COSEAL or DURASEAL).

The methods or compositions may be comprising injecting or otherwise introducing CCR7 ligand(s) at or near the transplant. The introduction may be performed periodically, e.g., daily, weekly. The methods or compositions may comprise a topical delivery device for delivering the CCR7 ligand(s): for example, a patch or gel applied to the skin that releases the ligands over time. The methods or compositions with the CCL19 and/or CCL21 peptide or portion(s) thereof may be delivered in an amount effective to induce tolerization of a transplant in an animal (human or non-human). The methods or compositions may be provided wherein the CCL19 and/or CCL21 peptide or portion thereof is delivered in an amount effective to induce tolerization in an animal to an antigen, wherein said animal (human or non-human) did not previously display tolerance of the antigen. The antigen may introduced in association with the CCR7 ligand(s). The antigen may be, for instance, an antigen of an implanted cell or tissue or organ, e.g., allogeneic, xenogeneic, non-syngeneic.

An embodiment is a chemokine used for treatment of immunorejection of a tissue by induction of tolerance to the tissue, the chemokine being chosen from the group consisting of CC-chemokine ligand-19 (CCL19) and CC-chemokine ligand-19 (CCL21). The chemokine may be a member of a fusion protein. The chemokine may be admixed with an upregulator of T-cells. The chemokine may be chosen from the group consisting of TGF-β, IL-10, and IL-35.

An embodiment is a composition or a method of treating a patient receiving a tissue implant comprising administering a chemokine chosen from the group consisting of CC-chemokine ligand-19 (CCL19), CC-chemokine ligand-19 (CCL21), and combinations thereof. The following options may be exercised additionally or in combination with each other. The administration may be made locally at the implant. The chemokine may be delivered transdermally or in a microparticle, liposome, or micelle. The method or composition may involve establishing a concentration gradient of the chemokine that is maximal at the tissue implant. An implantable pump may be used to release the chemokine or other agents administered with the same. The method may further comprise releasing the chemokine from a matrix implanted in the patient. The matrix may comprises fibrin. The tissue implant may comprises a skin graft placed over a fibrin matrix; the matrix may hold the chemokine(s) and/or other agents administered therewith. The matrix may comprise a covalently crosslinked biodegradable hydrogel. The composition or method may further comprise administering an upregulator of T-cells. The upregulator may comprise a member of the group consisting of Transforming Growth Factor beta (TGF-β), Interleukin-10 (IL-10), Interleukin-35 (IL-35), and combinations thereof. The upregulator may be administered locally and the chemokine may be administered systematically. Or the upregulator administered systematically and the chemokine locally; or both locally; or both systematically. The chemokine may be part of a fusion protein. The composition or method may involve administration of a plurality of fusion proteins, with the proteins each comprising at least one member of the group consisting of CCL19 and CCL21.

The composition or method may further comprise a second implantation of more of the same tissue, with the second implantation being made without administration of the chemokine. The composition or method may comprise administration of the chemokine release of the chemokine from an implanted cell genetically modified to overexpress the chemokine. The tissue may be chosen from the group consisting of stem cells, islets of Langerhans, stem cell-derived pancreatic beta cell-like cells, cardiomyocytes, stem cell-derived cardiomyocyte precursors to restore cardiac function, endothelial cells, and endothelial progenitor cells. The tissue may be fully or partially encapsulated. The encapsulating material may substantially limits contact of the tissue with immune cells in the patient and allow at least some of the immune cells to contact the tissue. This may be achieved by limiting the molecular weight cut off of the material and adjusting diffusion rates through the material. Examples include alginates, coacervates, and polymeric coatings.

Embodiments include a method of inducing immunotolerization for a tissue implanted in a patient comprising administering a chemokine to the patient in combination with the tissue, with the chemokine being administered in an amount effective to achieve immunotolerization to the tissue chosen from the group consisting of CC-chemokine ligand-19 (CCL19), CC-chemokine ligand-19 (CCL21), and combinations thereof. The method may further comprise withdrawal of immunosuppressant treatment after tolerization is achieved. The chemokine may be administered over a period of time and then no longer administered to the patient, the time being in a range between one month and twelve months. The method may further comprise administering, in combination with the chemokine, an upregulator of T-cells, wherein the upregulator is chosen from the group consisting of TGF-β, IL-10, and IL-35. The chemokine may be administered in an amount that is not effective for systemic immune suppression.

Embodiments include a vector comprising a nucleic acid encoding at least a portion of a chemokine that specifically binds to CCR7, the chemokine being chosen from the group consisting of CCL19, CCL21, and combinations thereof The vector may encode a fusion protein that comprises the chemokine, with the fusion protein further comprising a protein chosen from the group consisting of a transglutaminase substrate, a heparin-binding domain, a fibrin-binding domain, a protease substrate, Transforming Growth Factor beta (TGF-β), Interleukin-10 (IL-10), and Interleukin-35 (IL-35). A cell may be made that includes a vector as set forth herein, or overexpress a chemokine that specifically binds to CCR7, the chemokine being at least a portion of: CCL19 and/or CCL21. An advantage of engineering such a cell is that its expression may be stable in vivo in contrast with unmodified cells that may be regulated by the in vivo environment.

All patent applications, patents, and publications mentioned herein are hereby incorporated by reference herein for all purposes to the extent they do not directly contradict the explicit disclosures set forth herein; in the case of conflict, the specification controls.

REFFERENCES

Hereby incorporated by reference herein in their entirety for all purposes are the following publications: in case of conflict, the instant specification controls.

Akbar et al. (2007), "The dynamic co-evolution of memory and regulatory CD4+ T cells in the periphery", *Nat Rev Immunol.,* 7(3):231-7.

Ashour et al. (2007). "CCL21 is an effective surgical neoadjuvant for treatment of mammary tumors." *Cancer Biol Ther,* 6(8): 1206-10.

Bettini et al. (2009). "Regulatory T cells and inhibitory cytokines in autoimmunity." *Current Opinion in Immunology,* 21(6): 612-618.

Biollaz et al. (2009), "Site-specific anti-tumor immunity: differences in DC function, TGF-beta production and numbers of intratumoral Foxp3+ Treg", *Eur J Immunol.,* 39(5): 1323-33.

Braun et al. (2000), "The CC chemokine CK beta-11/MIP-3 beta/ELC/exodus 3 mediates tumor rejection of murine breast cancer cells through NK cells", *Journal of Immunology,* 164(8): 4025-4031.

Britschgi et al. (2008), "Dynamic modulation of CCR7 expression and function on naive T lymphocytes in vivo", *J Immunol.*, 181(11):7681-8.

Cabioglu et al. (2005), "CCR7 and CXCR4 as novel biomarkers predicting axillary lymph node metastasis in T1 breast cancer", *Clin Cancer Res*, 11: 5686.

Chen et al. (2008), "The indoleamine 2,3-dioxygenase pathway is essential for human plasmacytoid dendritic cell-induced adaptive T regulatory cell generation", *J Immunol.*, 181(8):5396-404.

Davalos-Misslitz et al. (2007) "Generalized multi-organ autoimmunity in CCR7-deficient mice." *Eur J Immunol* 37(3): 613-622.

Ding et al. (2003), "Association of CC chemokine receptor 7 with lymph node metastasis of esophageal squamous cell carcinoma", *Clin Cancer Res.*, 9(9):3406-12.

Dunn, et al. (2006), "Interferons, immunity and cancer immunoediting", *Nat Rev Immunol.*, 6(11):836-48.

Eberl et al. (2004), "An essential function for the nuclear receptor RORgamma(t) in the generation of fetal lymphoid tissue inducer cells", *Nat Immunol.*, 5(1):64-73.

Ebert et al. (2005), "Chemokine-mediated control of T cell traffic in lymphoid and peripheral tissues", *Mol Immunol.*, 42:799.

Fernandez-Centeno et al. (2000), "Crry/p65, a membrane complement regulatory protein, has costimulatory properties on mouse T cells", *J Immunol.*, 164(9):4533-42.

Forster et al. (1999), "CCR7 coordinates the primary immune response by establishing functional microenvironments in secondary lymphoid organs", *Cell*, 99(1):23-33.

Förster et al. (2008), "CCR7 and its ligands: balancing immunity and tolerance." *Nat Rev Immunol.*, 8(5): 362-371.

Fragale et al., (2008) "IFN regulatory factor-1 negatively regulates CD4+CD25+ regulatory T cell differentiation by repressing Foxp3 expression", *J Immunol.*, 181(3):1673-82.

Gao et al. (2005), "Anti-tumor Responses Induced by Chemokine CCL19 Transfected into an Ovarian Carcinoma Model via Fiber-Mutant Adenovirus Vector", *Biol. Pharm. Bull.*, 28(6):1066-1070.

Hubbell (2008), "Controlled Release Strategies in Tissue Engineering" *Tissue Engineering*, C. van Blitterswijk, P. Thompsen, J. Hubbell and R. Cancedda, Academic Press: 455-482.

Ilkovitch et al. (2008), "Immune modulation by melanoma-derived factors", *Exp Dermatol.*, 17(12): 977-85.

Johnson et al. (2008), "Cell traffic and the lymphatic endothelium", *Ann NY Acad Sci*, 1131:119-33.

Joyce et al. (2003), "Stage-specific vascular markers revealed by phage display in a mouse model of pancreatic islet tumorigenesis", *Cancer Cell*, 4(5): 393-403.

Junt et al. (2002), "Antiviral immune responses in the absence of organized lymphoid T cell zones in plt/plt mice", *J Immunol.*, 168(2):6032-40.

Katz et al. (2008), "Indoleamine 2,3-dioxygenase in T-cell tolerance and tumoral immune escape", *Immunol Rev.*, 222:206-21.

Kawase et al. (2008), "Podoplanin expression by cancer associated fibroblasts predicts poor prognosis of lung adenocarcinoma", *Int. J. Cancer,* 123(5):1053-9.

Kemper et al. (2003), "Activation of human CD4+cells with CD3 and CD46 induces a T-regulatory cell 1 phenotype", *Nature*, 421(6921):388-92.

Kirk et al. (2001), "T cell-dependent antitumor immunity mediated by secondary lymphoid tissue chemokine: Augmentation of dendritic cell-based immunotherapy." *Cancer Research*, 61(5): 2062-2070.

Krautwald et al. (2004), "Ectopic expression of CCL19 impairs alloimmune response in mice." *Immunology,* 112 (2): 301-9.

Kusmartsev et al. (2006),"Role of immature myeloid cells in mechanisms of immune evasion in cancer", *Cancer Immunol Immunother.,* 55(3):237-45.

Luther et al., (2002), "Differing activities of homeostatic chemokines CCL19, CCL21, and CXCL12 in lymphocyte and dendritic cell recruitment and lymphoid neogenesis", *J Immunol,* 169: 424-33.

Mantovani, et al. (2008), "Cancer-related inflammation", *Nature,* 454(7203):436-44.

Markiewski et al., (2008) "Modulation of the antitumor immune response by complement", *Nat Immunol.,* 9(11): 1225-35.

Martin et al. (2004), "A novel model for lymphocytic infiltration of the thyroid gland generated by transgenic expression of the CC chemokine CCL21." *J Immunol.,* 173(8): 4791-4798.

Meaning et al., (2007) "Distinctive role of CCR7 in migration and functional activity of naive- and effector/memory-like Treg subsets", *Eur J Immunol.,* 37(6):1575-1583.

Montes et al., (2008) "Tumor-induced senescent T cells with suppressor function: a potential form of tumor immune evasion", *Cancer Research,* 68(3) 870-9.

Moo-Young et al., "Tumor-derived TGF-beta mediates conversion of CD4+Foxp3+regulatory T cells in a murine model of pancreas cancer", *J Immunother.,* 32(1):12-21.

Mori et al. (2001), "Mice lacking expression of the chemokines CCL21-Ser and CCL19 (plt mice) demonstrate delayed but enhanced T cell immune responses." *J Exp Med.,* 193(2): 207-217.

Nomura et al. (2001). "Enhancement of anti-tumor immunity by tumor cells transfected with the secondary lymphoid tissue chemokine EBI-1-ligand chemokine and stromal cell-derived factor-1alpha chemokine genes." *Int J Cancer,* 91(5): 597-606.

Ochando et al. (2005), "Lymph node occupancy is required for the peripheral development of alloantigen-specific Foxp3+ regulatory T cells", *J Immunol.,* 174(11):6993-7005.

Ohl et al. (2004). "CCR7 governs skin dendritic cell migration under inflammatory and steady-state conditions." *Immunity,* 21(2): 279-88.

Peduto et al., "Inflammation recapitulates the ontogeny of lymphoid stromal cells", *J Immunol.,* 182(9):5789-99.

Randall et al. (2008), "Development of secondary lymphoid organs", *Annu Rev Immunol.,* 26:627-50.

Schmoekel et al. (2005), "Bone repair with a form of BMP-2 engineered for incorporation into fibrin cell ingrowth matrices", *Biotechnology and Bioengineering,* 89(3): 253-262.

Schneider et al. (2007), "CCR7 is required for the in vivo function of CD4+CD25+ regulatory T cells", *J Exp Med.,* 204(4):735-45.

Shankaran et al. (2001), "IFNgamma and lymphocytes prevent primary tumour development and shape tumour immunogenicity", *Nature,* 410(6832): 1107-11.

Sharma et al. (2000), "Secondary lymphoid tissue chemokine mediates T cell-dependent antitumor responses in vivo", *J Immunol.,* 164(9): 4558-4563.

Shields et al., (2007), "Autologous chemotaxis as a mechanism of tumor cell homing to lymphatics via interstitial flow and autocrine CCR7 signaling," *Cancer Cell,* 11(6): 526-38.

Sica et al. (2008), "Macrophage and Disease—The Macrophage Community Website", *Semin Cancer Biol.*, 18(5):349-55.

Turnquist et al. (2007), "CCL21 induces extensive intratumoral immune cell infiltration and specific anti-tumor cellular immunity." *Int J Oncol.*, 30(3): 631-639.

Varela et al. (2008), "Modulation of protective T cell immunity by complement inhibitor expression on tumor cells", *Cancer Res*, 68(16):6734-42.

Verbovetski et al. (2002), "Opsonization of apoptotic cells by autologous iC3b facilitates clearance by immature dendritic cells, down-regulates DR and CD86, and up-regulates CC chemokine receptor 7", *J Exp Med.*, 196(12): 1553-61.

Vicari et al. (2000), "Antitumor effects of the mouse chemokine 6Ckine/SLC through angiostatic and immunological mechanisms." *Journal of Immunol.*, 165(4): 1992-2000.

Weninger et al. (2003), "Naive T cell recruitment to nonlymphoid tissues: a role for endothelium-expressed CC chemokine ligand 21 in autoimmune disease and lymphoid neogenesis", *J Immunol.*, 170(9):4638-48.

Wiley et al. (2001), "Expression of CC chemokine receptor-7 and regional lymph node metastasis of B16 murine melanoma", *J Natl Cancer Inst.*, 93(21):1638-43.

William Jr. et al. (2009), "Molecular targets for cancer chemoprevention", *Nat Rev Drug Discov.*, 8(3):213-25.

Wu et al. (2008), "Tumor transfected with CCL21 enhanced reactivity and apoptosis resistance of human monocyte-derived dendritic cells", *Immunobiol.*, 213(5):417-26.

Xu et al. (2000), "A critical role for murine complement regulator crry in fetomaternal tolerance", *Science*, 287(5452):498-501.

Yasuda et al. (2007), "Chemokines CCL19 and CCL21 promote activation-induced cell death of antigen-responding T cells", *Blood*, 109(2):449-56.

Yoshida et al. (1998), "Secondary lymphoid-tissue chemokine is a functional ligand for the CC chemokine receptor CCR7." *Journal of Biological Chemistry*, 273(12): 7118-7122.

Ziegler et al. (2006), "CCL19-IgG prevents allograft rejection by impairment of immune cell trafficking", *Journal of the American Society of Nephrology* 17(9): 2521-32.

Ziegler et al. (2007). "CCR7 signaling inhibits T cell proliferation." *J Immunol* 179(10): 6485-6493.

---

The invention claimed is:

1. A method of treating a human patient receiving a tissue implant to achieve immunotolerance to the implant, the implant having exogenous antigens, the method comprising: administering a chemokine to the human patient to establish adaptive immune system treatment of the exogenous antigens as self-antigens to thereby achieve immunotolerance to the implant, the chemokine being chosen from the group consisting of CC-chemokine ligand-19 (CCL19), CC-chemokine ligand-21 (CCL21), and combinations thereof.

2. The method of claim 1 wherein the administration is made locally at the implant.

3. The method of claim 2 wherein the chemokine is delivered transdermally or in a microparticle, liposome, or micelle.

4. The method of claim 2 further comprising establishing a concentration gradient of the chemokine that is maximal at the tissue implant.

5. The method of claim 4 wherein an implantable pump releases the chemokine.

6. The method of claim 2 further comprising releasing the chemokine from a matrix implanted in the patient.

7. The method of claim 6 wherein the matrix comprises fibrin.

8. The method of claim 7 wherein the tissue implant comprises a skin graft placed over the fibrin.

9. The method of claim 6 wherein the matrix comprises a covalently crosslinked biodegradable hydrogel.

10. The method of claim 1 further comprising administering an upregulator of T-cells.

11. The method of claim 10 wherein the upregulator comprises a member of the group consisting of Transforming Growth Factor beta (TGF-β), Interleukin-10 (IL-10), Interleukin-35 (IL-35), and combinations thereof.

12. The method of claim 10 wherein the upregulator is administered locally and the chemokine is administered systematically.

13. The method of claim 1 wherein the chemokine is a portion of a fusion protein.

14. The method of claim 13 comprising the administration of a plurality of fusion proteins that are different from each other, with the proteins each comprising at least one member of the group consisting of CCL19 and CCL21.

15. The method of claim 1 further comprising a second implantation of more of the same tissue, with the second implantation being made without administration of the chemokine.

16. The method of claim 1 wherein administration of the chemokine comprises release of the chemokine from an implanted cell genetically modified to overexpress the chemokine.

17. The method of claim 1 wherein the tissue is chosen from the group consisting of stem cells, islets of Langerhans, stem cell-derived pancreatic beta cell-like cells, cardiomyocytes, stem cell-derived cardiomyocyte precursors to restore cardiac function, endothelial cells, and endothelial progenitor cells.

18. The method of claim 1 further comprising encapsulating the tissue.

19. The method of claim 1 wherein the encapsulating material substantially limits contact of the tissue with immune cells in the patient and allows at least some of the immune cells to contact the tissue.

20. The method of claim 13, wherein the fusion protein comprises a protein chosen from the group consisting of a transglutaminase substrate, a heparin-binding domain, a fibrin-binding domain, a protease substrate, Transforming Growth Factor beta (TGF-β), Interleukin-10 (IL-10), and Interleukin-35 (IL-35).

21. The method of claim 13, wherein the fusion protein comprises a motif for binding to fibrin and a member of the group consisting of Transforming Growth Factor beta (TGF-β), Interleukin-10 (IL-10), Interleukin-35 (IL-35).

22. The method of claim 13, wherein the fusion protein comprises a transglutaminase substrate and a plasmin substrate.

23. A method of inducing immunotolerization for a tissue implanted in a human patient, said tissue having exogenous antigens, the method comprising administering a chemokine to the human patient in combination with the tissue, with the chemokine being administered in an amount effective to establish adaptive immune system treatment of the exogenous antigens as self-antigens to thereby achieve immunotolerization to the tissue chosen from the group consisting of CC-chemokine ligand-19 (CCL19), CC-chemokine ligand-21 (CCL21), and combinations thereof.

24. The method of claim 23 further comprising withdrawal of immunosuppressant treatment after tolerization is achieved.

25. The method of claim 23 wherein the chemokine is administered over a period of time and then no longer administered to the patient, the time being in a range between one month and twelve months.

26. The method of claim 23 further comprising administering, in combination with the chemokine, an upregulator of T-cells, wherein the upregulator is chosen from the group consisting of TGF-β, IL-10, and IL-35.

* * * * *

SEQUENCE LISTING

```
<160> NUMBER OF SEQ ID NOS: 29

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
ggagctagaa cgattcgcag tta                                           23

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
ggtgtagctg tcccagtatt tgtc                                          24

<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3
acagccttct gatgtttcta acaggccagg                                    30

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ggcactgaca attccgtggt                                               20
```

```
<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
agggacgtag cagaaggacg                                                    20

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
acgtcctttc catggctgct cgc                                                23

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
aaaacgagca gtgacgtgag c                                                  21

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ttcagtcatg ctgctagcgc                                                    20

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
tgcacggaag cgtctcgtct cagtc                                              25

<210> SEQ ID NO 10
<211> LENGTH: 8
<212> TYPE: PRT
<213> ORGANISM: Homo sapiens

<400> SEQUENCE: 10

Asn Gln Glu Gln Val Ser Pro Leu
1               5

<210> SEQ ID NO 11
<211> LENGTH: 402
<212> TYPE: DNA
<213> ORGANISM: artificial sequence
<220> FEATURE:
<223> OTHER INFORMATION: primer
```

```
<400> SEQUENCE: 11
atggctcaga tgatgactct gagcctcctt agcctggtcc tggctctctg catcccctgg      60
acccaaggca gtgatggagg gggtcaggac tgctgcctta agtacagcca agagaaaatt     120
ccctacagta ttgtccgagg ctataggaag caagaaccaa gtttaggctg tcccatcccg     180
gcaatcctgt tctcaccccg gaagcactct aagcctgagc tatgtgcaaa ccctgaggaa     240
ggctgggtgc agaacctgat gcgccgcctg gaccagcctc cagccccagg aaacaaagc      300 cccggctgca ggaagaaccg ggaacctct aagtctggaa agaaaggaaa gggctccaag      360
ggctgcaaga gaactgaaca gacacagccc tcaagaggat ag                        402

<210> SEQ ID NO 12
<211> LENGTH: 24
<212> TYPE: DNA
<213> ORGANISM: homo sapiens

<400> SEQUENCE: 12
aaccaggagc aggtgagccc cctg                                             24

<210> SEQ ID NO 13
<211> LENGTH: 33
<212> TYPE: DNA
<213> ORGANISM: homo sapiens

<400> SEQUENCE: 13
cccgtggagc tgcccctgat caagatgaag ccc                                   33

<210> SEQ ID NO 14
<211> LENGTH: 69
<212> TYPE: DNA
<213> ORGANISM: artificial sequence
<220> FEATURE:
<223> OTHER INFORMATION: fusion protein

<400> SEQUENCE: 14
atggctcaga tgatgactct gagcctcctt agcctggtcc tggctctctg catcccctgg      60
acccaaggc                                                              69

<210> SEQ ID NO 15
<211> LENGTH: 1134
<212> TYPE: DNA
<213> ORGANISM: Mus musculus

<400> SEQUENCE: 15
cacacacaca gaccccaact tgcagctgtc catctcacct acagctctgg tctcatcctc      60
aactcaacca caatcatggc tcagatgatg actctgagcc tccttagcct ggtcctggct     120
ctctgcatcc cctggaccca agtaccaag agggagagg ctttggctgg ggaaggggc        180 catagagaca ccttataagc cgcagctggg tctgtgcacc taccttgcag gcagtgatgg     240
agggggacag gactgctgcc ttaagtacag ccagaagaaa attccctaca gtattgtccg     300
aggctatagg aagcaagaac caagtttagg ctgtcccatc ccggcaatcc tgtgagtgcg     360
ctgatcgggt gggtacaggc tggtggttgg gttggggagg tgtgatgggc cagactaaga     420
aagcttgctg ccctccaacc ctcaggttct taccccggaa gcactctaag cctgagctat     480
gtgcaaaccc tgaggaaggc tgggtgcaga acctgatgcg ccgcctggac cagcctccag     540
ccccagggaa acaaagcccc ggctgcagga agaaccgggg aacctctaag tctggaaaga     600
aaggaaaggg ctccaagggc tgcaagaggt gaggctgctg aagggatgga agggaacaa      660
```

```
agaggagcct ccctccacct gcctctcaca cttcttttct gccctgccag aactgaacag    720
acacagccct caagaggata gcccagtagc ccgcctggag cccaggagat cccccacgaa    780
cttcaagctg gtggttcac ggtccaactc acaggcaaag agggagctag aaaacagact     840
caggagccca aagcagccac ctcatgctgg cctccgtcca cacccttgcc ctgcttcaac    900
cattacatct gcacggccat ccctttctta cctggcggag ctgccttccc tggggtagac    960
ctagagagtc agaagaaaga gtgtctccca gggaatgagg aaggagacag caggactgtc    1020
ccctctagga ggtcactcag gtcccaagac ctgaacctgc tctccatggc ccctcccct    1080 tgtccttgca cctatgattt atacctaact gaataaaaaa gtgatccagc ctca          1134
```

<210> SEQ ID NO 16
<211> LENGTH: 402
<212> TYPE: DNA
<213> ORGANISM: mus musculus

<400> SEQUENCE: 16

```
atggctcaga tgatgactct gagcctcctt agcctggtcc tggctctctg catcccctgg    60
acccaaggca gtgatggagg gggacaggac tgctgcctta agtacagcca agagaaaatt   120
ccctacagta ttgtccgagg ctataggaag caagaaccaa gtttaggctg tcccatcccg   180
gcaatcctgt tcttaccccg gaagcactct aagcctgagc tatgtgcaaa ccctgaggaa   240
ggctgggtgc agaacctgat gcgccgcctg gaccagcctc cagccccagg gaaacaaagc   300
cccggctgca ggaagaaccg ggaacctct aagtctggaa agaaggaaa gggctccaag    360 ggctgcaaga gaactgaaca gacacagccc tcaagaggat ag                      402
```

<210> SEQ ID NO 17
<211> LENGTH: 133
<212> TYPE: PRT
<213> ORGANISM: mus musculus

<400> SEQUENCE: 17

```
Met Ala Gln Met Met Thr Leu Ser Leu Leu Ser Leu Val Leu Ala Leu
1               5                   10                  15

Cys Ile Pro Trp Thr Gln Gly Ser Asp Gly Gly Gly Gln Asp Cys Cys
                20                  25                  30

Leu Lys Tyr Ser Gln Lys Lys Ile Pro Tyr Ser Ile Val Arg Gly Tyr
        35                  40                  45

Arg Lys Gln Glu Pro Ser Leu Gly Cys Pro Ile Pro Ala Ile Leu Phe
    50                  55                  60

Leu Pro Arg Lys His Ser Lys Pro Glu Leu Cys Ala Asn Pro Glu Glu
65                  70                  75                  80

Gly Trp Val Gln Asn Leu Met Arg Arg Leu Asp Gln Pro Pro Ala Pro
                85                  90                  95

Gly Lys Gln Ser Pro Gly Cys Arg Lys Asn Arg Gly Thr Ser Lys Ser
            100                 105                 110

Gly Lys Lys Gly Lys Gly Ser Lys Gly Cys Lys Arg Thr Glu Gln Thr
        115                 120                 125

Gln Pro Ser Arg Gly
    130
```

<210> SEQ ID NO 18
<211> LENGTH: 426
<212> TYPE: DNA
<213> ORGANISM: artificial sequence
<220> FEATURE:
<223> OTHER INFORMATION: encodes fusion protein

<400> SEQUENCE: 18

| | |
|---|---|
| atggctcaga tgatgactct gagcctcctt agcctggtcc tggctctctg catcccctgg | 60 |
| acccaaggca gtgatggagg gggtcaggac tgctgcctta agtacagcca agaagaaatt | 120 |
| ccctacagta ttgtccgagg ctataggaag caagaaccaa gtttaggctg tcccatcccg | 180 |
| gcaatcctgt tctcaccccg gaagcactct aagcctgagc tatgtgcaaa ccctgaggaa | 240 |
| ggctgggtgc agaacctgat gcgccgcctg accagcctc cagccccagg gaaacaaagc | 300 |
| cccggctgca ggaagaaccg ggaacctct aagtctggaa agaaaggaaa gggctccaag | 360 |
| ggctgcaaga gaactgaaca gacacagccc tcaagaggaa accaggagca ggtgagcccc | 420 |
| ctgtag | 426 |

<210> SEQ ID NO 19
<211> LENGTH: 141
<212> TYPE: PRT
<213> ORGANISM: artificial sequence
<220> FEATURE:
<223> OTHER INFORMATION: fusion protein

<400> SEQUENCE: 19

```
Met Ala Gln Met Met Thr Leu Ser Leu Leu Ser Leu Val Leu Ala Leu
1               5                   10                  15

Cys Ile Pro Trp Thr Gln Gly Ser Asp Gly Gly Gly Gln Asp Cys Cys
            20                  25                  30

Leu Lys Tyr Ser Gln Lys Lys Ile Pro Tyr Ser Ile Val Arg Gly Tyr
        35                  40                  45

Arg Lys Gln Glu Pro Ser Leu Gly Cys Pro Ile Pro Ala Ile Leu Phe
    50                  55                  60

Ser Pro Arg Lys His Ser Lys Pro Glu Leu Cys Ala Asn Pro Glu Glu
65                  70                  75                  80

Gly Trp Val Gln Asn Leu Met Arg Arg Leu Asp Gln Pro Pro Ala Pro
                85                  90                  95

Gly Lys Gln Ser Pro Gly Cys Arg Lys Asn Arg Gly Thr Ser Lys Ser
            100                 105                 110

Gly Lys Lys Gly Lys Gly Ser Lys Gly Cys Lys Arg Thr Glu Gln Thr
        115                 120                 125

Gln Pro Ser Arg Gly Asn Gln Glu Gln Val Ser Pro Leu
    130                 135                 140
```

<210> SEQ ID NO 20
<211> LENGTH: 459
<212> TYPE: DNA
<213> ORGANISM: artificial sequence
<220> FEATURE:
<223> OTHER INFORMATION: encodes fusion protein

<400> SEQUENCE: 20

| | |
|---|---|
| atggctcaga tgatgactct gagcctcctt agcctggtcc tggctctctg catcccctgg | 60 |
| acccaaggca gtgatggagg gggtcaggac tgctgcctta agtacagcca agaagaaatt | 120 |
| ccctacagta ttgtccgagg ctataggaag caagaaccaa gtttaggctg tcccatcccg | 180 |
| gcaatcctgt tctcaccccg gaagcactct aagcctgagc tatgtgcaaa ccctgaggaa | 240 |
| ggctgggtgc agaacctgat gcgccgcctg accagcctc cagccccagg gaaacaaagc | 300 |
| cccggctgca ggaagaaccg ggaacctct aagtctggaa agaaaggaaa gggctccaag | 360 |
| ggctgcaaga gaactgaaca gacacagccc tcaagaggac ccgtggagct gccccctgatc | 420 | aagatgaagc ccaaccagga gcaggtgagc ccctgtag          459

<210> SEQ ID NO 21
<211> LENGTH: 152
<212> TYPE: PRT
<213> ORGANISM: artificial sequence
<220> FEATURE:
<223> OTHER INFORMATION: fusion protein

<400> SEQUENCE: 21

```
Met Ala Gln Met Met Thr Leu Ser Leu Leu Ser Leu Val Leu Ala Leu
1               5                   10                  15

Cys Ile Pro Trp Thr Gln Gly Ser Asp Gly Gly Gln Asp Cys Cys
            20                  25                  30

Leu Lys Tyr Ser Gln Lys Lys Ile Pro Tyr Ser Ile Val Arg Gly Tyr
        35                  40                  45

Arg Lys Gln Glu Pro Ser Leu Gly Cys Pro Ile Pro Ala Ile Leu Phe
    50                  55                  60

Ser Pro Arg Lys His Ser Lys Pro Glu Leu Cys Ala Asn Pro Glu Glu
65                  70                  75                  80

Gly Trp Val Gln Asn Leu Met Arg Arg Leu Asp Gln Pro Pro Ala Pro
                85                  90                  95

Gly Lys Gln Ser Pro Gly Cys Arg Lys Asn Arg Gly Thr Ser Lys Ser
            100                 105                 110

Gly Lys Lys Gly Lys Gly Ser Lys Gly Cys Lys Arg Thr Glu Gln Thr
        115                 120                 125

Gln Pro Ser Arg Gly Pro Val Glu Leu Pro Leu Ile Lys Met Lys Pro
    130                 135                 140

Asn Gln Glu Gln Val Ser Pro Leu
145                 150
```

<210> SEQ ID NO 22
<211> LENGTH: 429
<212> TYPE: DNA
<213> ORGANISM: artificial sequence
<220> FEATURE:
<223> OTHER INFORMATION: encodes fusion protein

<400> SEQUENCE: 22

```
atggctcagt cactggctct gagcctcctt atcctggttc tggcctttgg catccccagg     60
acccaaggca gtgatggagg ggctcaggac tgttgcctca gtacagccaa aggaagatt    120 cccgccaagg ttgtccgcag ctaccggaag caggaaccaa gcttaggctg ctccatccca   180
gctatcctgt tcttgccccg caagcgctct caggcagagc tatgtgcaga cccaaaggag   240
ctctgggtgc agcagctgat gcagcatctg acaagacac catccccaca gaaaccagcc   300
cagggctgca ggaaggacag ggggcctcc aagactggca agaaaggaaa gggctccaaa   360
ggctgcaaga ggactgagcg gtcacagacc cctaaagggc caaaccagga gcaggtgagc   420
ccctgtag                                                             429
```

<210> SEQ ID NO 23
<211> LENGTH: 142
<212> TYPE: PRT
<213> ORGANISM: artificial sequence
<220> FEATURE:
<223> OTHER INFORMATION: fusion protein

<400> SEQUENCE: 23

```
Met Ala Gln Ser Leu Ala Leu Ser Leu Leu Ile Leu Val Leu Ala Phe
1               5                   10                  15
```

```
Gly Ile Pro Arg Thr Gln Gly Ser Asp Gly Gly Ala Gln Asp Cys Cys
        20                  25                  30

Leu Lys Tyr Ser Gln Arg Lys Ile Pro Ala Lys Val Val Arg Ser Tyr
        35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro Asn Gln Glu Gln Val Ser Pro Leu
    130                 135                 140
```

<210> SEQ ID NO 24
<211> LENGTH: 462
<212> TYPE: DNA
<213> ORGANISM: artificial sequence
<220> FEATURE:
<223> OTHER INFORMATION: fusion protein

<400> SEQUENCE: 24

```
atggctcagt cactggctct gagcctcctt atcctggttc tggcctttgg catccccagg      60
acccaaggca gtgatggagg ggctcaggac tgttgcctca gtacagccaa aggaagatt     120 cccgccaagg ttgtccgcag ctaccggaag caggaaccaa gcttaggctg ctccatccca    180
gctatcctgt tcttgccccg caagcgctct caggcagagc tatgtgcaga cccaaaggag    240
ctctgggtgc agcagctgat gcagcatctg gacaagacac catccccaca gaaaccagcc    300
cagggctgca ggaaggacag gggggcctcc aagactggca gaaaggaaa gggctccaaa    360 ggctgcaaga ggactgagcg gtcacagacc cctaaagggc cacccgtgga gctgcccctg    420
atcaagatga gcccaaccag gagcaggtga gccccctgt ag                        462
```

<210> SEQ ID NO 25
<211> LENGTH: 153
<212> TYPE: PRT
<213> ORGANISM: artificial sequence
<220> FEATURE:
<223> OTHER INFORMATION: fusion protein

<400> SEQUENCE: 25

```
Met Ala Gln Ser Leu Ala Leu Ser Leu Leu Ile Leu Val Leu Ala Phe
1               5                   10                  15

Gly Ile Pro Arg Thr Gln Gly Ser Asp Gly Gly Ala Gln Asp Cys Cys
        20                  25                  30

Leu Lys Tyr Ser Gln Arg Lys Ile Pro Ala Lys Val Val Arg Ser Tyr
        35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110
```

```
                100               105               110
Gly Lys Lys Gly Lys Gly Ser Lys Gly Cys Lys Arg Thr Glu Arg Ser
        115                 120                 125

Gln Thr Pro Lys Gly Pro Val Glu Leu Pro Leu Ile Lys Met Lys
        130                 135                 140

Pro Asn Gln Glu Gln Val Ser Pro Leu
145                 150

<210> SEQ ID NO 26
<211> LENGTH: 1146
<212> TYPE: DNA
<213> ORGANISM: homo sapiens

<400> SEQUENCE: 26
atcccagccc acgcacagac ccccaacttg cagctgccca cctcaccctc agctctggcc      60
tcttactcac cctctaccac agacatggct cagtcactgg ctctgagcct ccttatcctg     120
gttctggcct ttggcatccc caggacccaa ggtaccaagg cagggagggg ccttgcatgg     180
ggctaagggg atcaagaggc ctggatagga gcttgccagc agcccctggc tccctgtgaa     240
tcccaccctg caggcagtga tggaggggct caggactgtt gcctcaagta cagccaaagg     300
aagattcccg ccaaggttgt ccgcagctac cggaagcagg aaccaagctt aggctgctcc     360
atcccagcta tcctgtgagt ggacacaaag gggtgggtac tggctggtga cggggtgggg     420
agggcatggt gggcaagact aagaaggctt actagccccc acccgcaggt tcttgccccg     480
caagcgctct caggcagagc tatgtgcaga cccaaaggag ctctgggtgc agcagctgat     540
gcagcatctg gacaagacac catccccaca gaaaccagcc cagggctgca ggaaggacag     600
gggggcctcc aagactggca agaaggaaa gggctccaaa ggctgcaaga ggtgaggaat     660
ctgagggatg tgggtaaagg ggagcctcag tcagcccctc acacccctct tctgccctca     720
caggactgag cggtcacaga cccctaaagg gccatagccc agtgagcagc tggagccct     780 ggagacccca ccagcctcac cagcgcttga agcctgaacc caagatgcaa gaggaggct     840 atgctcaggg gccctggagc agccacccca tgctggcctt gccacactct ttctcctgct     900
ttaaccaccc catctgcatt cccagctcta ccctgcatgg ctgagctgcc acagcaggc     960 caggtccaga gagaccgagg agggagagtc tcccagggag catgagagga ggcagcagga    1020
ctgtcccctt gaaggagaat catcaggacc ctggacctga tacggctccc cagtacaccc    1080
cacctcttcc ttgtaaatat gatttatacc taactgaata aaaagctgtt ctgtcttccc    1140
acccaa                                                              1146

<210> SEQ ID NO 27
<211> LENGTH: 405
<212> TYPE: DNA
<213> ORGANISM: homo sapiens

<400> SEQUENCE: 27
atggctcagt cactggctct gagcctcctt atcctggttc tggcctttgg catccccagg      60
acccaaggca gtgatggagg ggctcaggac tgttgcctca gtacagccaa aggaagatt     120 cccgccaagg ttgtccgcag ctaccggaag caggaaccaa gcttaggctg ctccatccca     180
gctatcctgt tcttgccccg caagcgctct caggcagagc tatgtgcaga cccaaaggag     240
ctctgggtgc agcagctgat gcagcatctg gacaagacac catccccaca gaaaccagcc     300
cagggctgca ggaaggacag gggggcctcc aagactggca agaaggaaa gggctccaaa     360 ggctgcaaga ggactgagcg gtcacagacc cctaaagggc catag                    405
```

```
<210> SEQ ID NO 28
<211> LENGTH: 134
<212> TYPE: PRT
<213> ORGANISM: homo sapiens

<400> SEQUENCE: 28

Met Ala Gln Ser Leu Ala Leu Ser Leu Leu Ile Leu Val Leu Ala Phe
1               5                   10                  15

Gly Ile Pro Arg Thr Gln Gly Ser Asp Gly Gly Ala Gln Asp Cys Cys
            20                  25                  30

Leu Lys Tyr Ser Gln Arg Lys Ile Pro Ala Lys Val Val Arg Ser Tyr
        35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro
    130

<210> SEQ ID NO 29
<211> LENGTH: 9
<212> TYPE: PRT
<213> ORGANISM: mus musculus

<400> SEQUENCE: 29

Ser Val Tyr Asp Phe Phe Val Trp Leu
1               5
```